(12) United States Patent
Piechotta et al.

(10) Patent No.: US 11,703,511 B2
(45) Date of Patent: Jul. 18, 2023

(54) ANTI-ISOASP7 AMYLOID β (Aβ) ANTIBODIES AND USES THEREOF

(71) Applicant: FRAUNHOFER-GESELLSCHAFT ZUR FÖRDERUNG DER ANGEWANDTEN FORSCHUNG E.V., Munich (DE)

(72) Inventors: Anke Piechotta, Halle (DE); Kathrin Gnoth, Halle (DE); Holger Cynis, Halle (DE); Jens-Ulrich Rahfeld, Seegebiet Mansfelder Land (DE); Stephan Schilling, Halle (DE); Hans-Ulrich Demuth, Halle (DE)

(73) Assignee: FRAUNHOFER-GESELLSCHAFT ZUR FÖRDERUNG DER ANGEWANDTEN FORSCHUNG E.V., Munich (DE)

( * ) Notice: Subject to any disclaimer, the term of this patent is extended or adjusted under 35 U.S.C. 154(b) by 588 days.

(21) Appl. No.: 16/632,289

(22) PCT Filed: Jul. 17, 2018

(86) PCT No.: PCT/EP2018/069404
§ 371 (c)(1),
(2) Date: Jan. 17, 2020

(87) PCT Pub. No.: WO2019/016213
PCT Pub. Date: Jan. 24, 2019

(65) Prior Publication Data
US 2020/0264197 A1 Aug. 20, 2020

(30) Foreign Application Priority Data
Jul. 19, 2017 (EP) .................................. 17182167

(51) Int. Cl.
*C07K 16/18* (2006.01)
*C07K 16/44* (2006.01)
(Continued)

(52) U.S. Cl.
CPC ... *G01N 33/6896* (2013.01); *A61K 39/39583* (2013.01); *C07K 16/18* (2013.01);
(Continued)

(58) Field of Classification Search
None
See application file for complete search history.

(56) References Cited

U.S. PATENT DOCUMENTS 4,816,567 A   3/1989 Cabilly et al.
5,223,409 A   6/1993 Ladner et al.
(Continued)

FOREIGN PATENT DOCUMENTS

EP   0 125 023 A1   11/1984
EP   0 171 496 A2   2/1986
(Continued)

OTHER PUBLICATIONS

Kussie et al., A single engineered amino acid substitution changes antibody fine specificity. J Immunol. Jan. 1, 1994;152(1):146-52. (Year: 1994).*
(Continued)

*Primary Examiner* — Aurora M Fontainhas
(74) *Attorney, Agent, or Firm* — Seed IP Law Group LLP

(57) ABSTRACT

The present invention can be included in the field of medicine. Specifically, the present invention provides antibodies and antigen-binding fragments thereof which can bind isoAsp7 amyloid β (Aβ) and a pharmaceutical composition comprising the antibodies or antigen-binding fragments thereof. IsoAsp7 Aβ can be found in plaques of Alzheimer's patients and is thus a suitable target for the treatment and/or (Continued)

Figure 1:
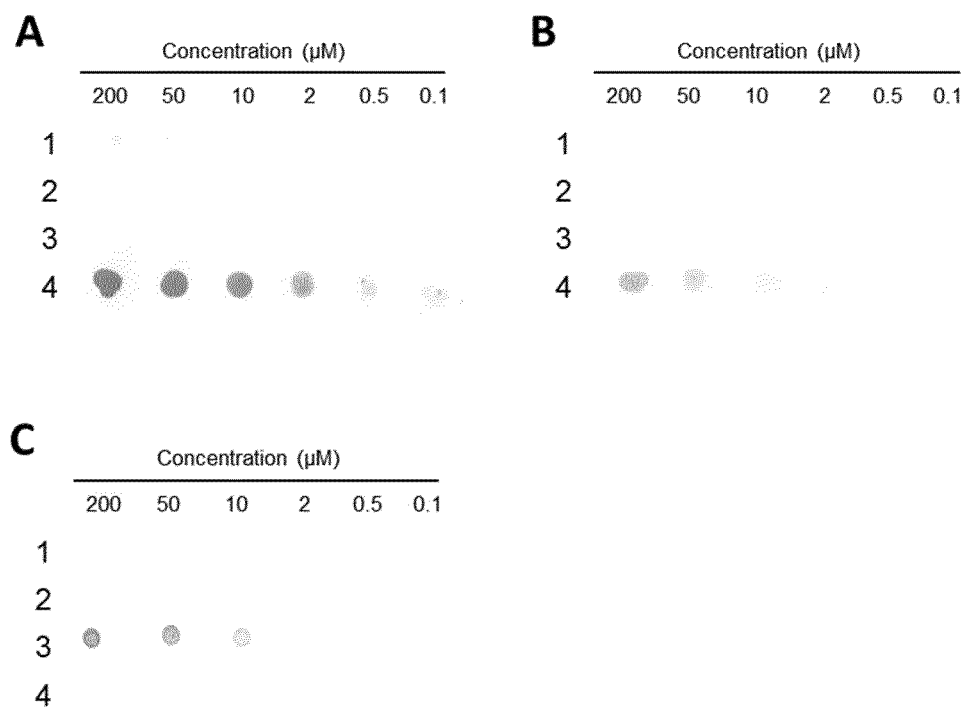

prevention of Aβ-related diseases such as Alzheimer's disease. Thus, the antibodies, antigen-binding fragments thereof and the pharmaceutical composition comprising either can be used to treat and/or prevent neurodegenerative diseases. Further, the present invention provides hybridoma cell lines, the use of the antibodies or antigen-binding fragments thereof for the diagnosis and/or prognosis of a neurodegenerative disease and a method for detecting isoAsp7 Aβ in an isolated sample.

16 Claims, 12 Drawing Sheets

Specification includes a Sequence Listing.

(51) Int. Cl.
    *A61K 39/395*     (2006.01)
    *G01N 33/68*      (2006.01)
    *G01N 33/543*     (2006.01)
(52) U.S. Cl.
    CPC ........... *C07K 16/44* (2013.01); *G01N 33/543* (2013.01); *C07K 2317/24* (2013.01); *C07K 2317/565* (2013.01); *C07K 2317/92* (2013.01)

(56) References Cited

U.S. PATENT DOCUMENTS

| | | |
|---|---|---|
| 5,225,539 A | 7/1993 | Winter |
| 5,585,089 A | 12/1996 | Queen et al. |
| 5,624,821 A | 4/1997 | Winter et al. |
| 5,648,260 A | 7/1997 | Winter et al. |
| 5,693,761 A | 12/1997 | Queen et al. |
| 5,693,762 A | 12/1997 | Queen et al. |
| 2017/0355756 A1* | 12/2017 | Julien ............... A61P 25/00 |

FOREIGN PATENT DOCUMENTS

| | | | |
|---|---|---|---|
| EP | 0 173 494 A2 | 3/1986 | |
| EP | 0 184 187 A2 | 6/1986 | |
| EP | 0 388 151 A1 | 9/1990 | |
| EP | 0 519 596 A1 | 12/1992 | |
| GB | 2 188 638 A | 10/1987 | |
| JP | 2008-538925 A | 11/2008 | |
| WO | 86/01533 A1 | 3/1986 | |
| WO | 87/02671 A1 | 5/1987 | |
| WO | 90/02809 A1 | 3/1990 | |
| WO | 91/00906 A1 | 1/1991 | |
| WO | 91/10741 A1 | 7/1991 | |
| WO | 91/17271 A1 | 11/1991 | |
| WO | 92/01047 A1 | 1/1992 | |
| WO | 92/03917 A1 | 3/1992 | |
| WO | 92/03918 A1 | 3/1992 | |
| WO | 92/09690 A2 | 6/1992 | |
| WO | 92/15679 A1 | 9/1992 | |
| WO | 92/18619 A1 | 10/1992 | |
| WO | 92/20791 A1 | 11/1992 | |
| WO | 93/01288 A1 | 1/1993 | |
| WO | 94/04678 A1 | 3/1994 | |
| WO | 2006/036291 A2 | 4/2006 | |
| WO | WO-2008068048 A2 * | 6/2008 | ............... A61P 31/10 |

OTHER PUBLICATIONS

Edwards et al., The remarkable flexibility of the human antibody repertoire; isolation of over one thousand different antibodies to a single protein, BLyS. J Mol Biol. Nov. 14, 2003;334(1):103-18. (Year: 2003).*
Chen et al., Enhancement and destruction of antibody function by somatic mutation: unequal occurrence is controlled by V gene combinatorial associations. EMBO J. Jun. 15, 1995;14(12):2784-94. (Year: 1995).*
Koenig et al., Mutational landscape of antibody variable domains reveals a switch modulating the interdomain conformational dynamics and antigen binding. PNAS Jan. 24, 2017 114(4) E486-E495; first published Jan. 5, 2017; (Year: 2017).*
Aswad et al., "Isoaspartate in peptides and proteins: formation, significance, and analysis," *J. Pharm. Biomed. Anal.* 27:1129-1136, 1999.
Bancher et al., "Accumulation of abnormally phosphorylated τ precedes the formation of neurofibrillary tangles in Alzheimer's disease," *Brain Research* 477:90-99, 1989.
Bard et al., "Epitope and isotype specificities of antibodies to β-amyloid peptide for protection against Alzheimer's disease-like neuropathology," *PNAS* 100(4):2023-2028, Feb. 2003.
Bard et al., "Peripherally administered antibodies against amyloid B-peptide enter the central nervous system and reduce pathology in a mouse model of Alzheimer disease," *Nature Medicine* 6(8):916-919, Aug. 2000.
Biedenkapp et al., "Hippocampal and extrahippocampal systems compete for control of contextual fear: Role of ventral subiculum and amygdala," *Learning & Memory*:38-45, 2009.
Braak et al., "Neuropathological stageing of Alzheimer-related changes," *Acta Neuropathol* 82:239-259, Jun. 1991.
Brookmeyer et al., "Survival Following a Diagnosis of Alzheimer Disease," *Arch Neurol* 59:1764-1767, Nov. 2002.
Bussière et al., "Morphological Characterization of Thioflavin-S-Positive Amyloid Plaques in Transgenic Alzheimer Mice and Effect of Passive Aβ Immunotherapy on Their Clearance," *American Journal of Pathology* 165(3):987-995, Sep. 2004.
DeMattos et al., "A Plaque-Specific Antibody Clears Existing β-amyloid Plaques in Alzheimer's Disease Mice," *Neuron* 76:908-920, Dec. 2012.
DeMattos et al., "Peripheral and anti-Aβ antibody alters CNS and plasma Aβ clearance and decreases brain Aβ burden in a mouse model of Alzheimer's disease," *PNAS* 98(15):8850-8855, Jul. 2001.
Fonseca et al., "The Presence of Isoaspartic Acid in β-Amyloid Plaques Indicates Plaque Age," *Experimental Neurology* 157:277-288, Feb. 1999.
Frost et al., "An anti-pyroglutamate-3 Aβ vaccine reduces plaques and improves cognition in APPswe/PS1ΔE9 mice," *Neurobiology of Aging* 36:3187-3199, 2015.
Frost et al., "Passive Immunization against Pyroglutamate-3 Amyloid-β Reduces Plaque Burden in Alzheimer-Like Transgenic Mice: A Pilot Study," *Neurodegenerative Dis* 10:265-270, 2012.
Frost et al., "Pyroglutamate-3 Amyloid-β Deposition in the Brains of Humans, Non-Human Primates, Canines, and Alzheimer Disease-Like Transgenic Mouse Models," *The American Journal of Pathology* 183(2):369-381, Aug. 2013.
Fukuda et al., "Synthesis, Aggregation, and Neurotoxicity of the Alzheimer's Aβ1-42 Amyloid Peptide and Its Isoaspartyl Isomers," *Bioorganic & Medicinal Chemistry Letters* 9:953-956, 1999.
Geiger et al., "Deamidation, Isomerization, and Racemization at Asparaginyl and Aspartyl Residues in Peptides," *The Journal of Biological Chemistry* 262(2):785-794, Jan. 1987.
Glenner et al., "Alzheimer's Disease and Down's Syndrome: Sharing of a Unique Cerebrovascular Amyloid Fibril Protein," *Biochemical and Biophysical Research Communications* 122(3):1131-1135, Aug. 1984.
Gnoth et al., "Targeting isoaspartate-modified Aβ rescues behavioral deficits in transgenic mice with Alzheimer's disease-like pathology," *Alzheimer's Research & Therapy* 12:1-20, 2020.
Gremer et al., "Fibril structure of amyloid-β(1-42) by cryo-electron microscopy," *Science* 358:116-119, Oct. 2017.
Grochowska et al., "Posttranslational modification impact on the mechanism by which amyloid-β induces synaptic dysfunction," *EMBO Reports* 18(6):962-981, 2017.
Güttler et al., "A quantitative analysis of spontaneous isoaspartate formation from N-terminal asparaginyl and aspartyl residues," *Amino Acids* 44:1205-1214, Jan. 2013.
Haass et al., "Targeting of cell-surface β-amyloid precursor protein to lysosomes: alternative processing into amyloid-bearing fragments," *Nature* 357:500-503, Jun. 1992.
Hyman et al., "Editorial on Consensus Recommendations for the Postmortem Diagnosis of Alzheimer Disease from the National

(56) References Cited

OTHER PUBLICATIONS

Institute on Aging and the Reagan Institute Working Group on Diagnostic Criteria for the Neuropathological Assessment of Alzheimer Disease," *Journal of Neuropathology and Experimental Neurology* 56(10):1095-1097, Oct. 1997.
Kozin et al., "Peripherally Applied Synthetic Peptide isoAsp7-Aβ(1-42) Triggers Cerebral β-Amyloidosis," *Neurotox Res* 24:370-376, May 2013.
Kulikova et al., "Intracerebral Injection of Metal-Binding Domain of Aβ Comprising the Isomerized Asp7 Increases the Amyloid Burden in Transgenic Mice," *Neurotox Res* 29:551-557, Feb. 2016.
Kumar et al., "Extracellular phosphorylation of the amyloid β-peptide promotes formation of toxic aggregates during the pathogenesis of Alzheimer's disease," *The EMBO Journal* 30:2255-2265, 2011.
Kummer et al., "Nitration of Tyrosine 10 Critically Enhances Amyloid β Aggregation and Plaque Formation," *Neuron* 71:833-844, Sep. 2011.
Kummer et al., "Truncated and modified amyloid-beta species," *Alzheimer's Research & Therapy* 6(28):1-9, 2014.
Kuo et al., "Irreversible dimerization/tetramerization and post-translational modifications inhibit proteolytic degradation of A β peptides of Alzheimer's disease," *Biochimica et Biophysica Acta* 1406:291-298, 1998.
Masters et al., "Biochemistry of Amyloid β-Protein and Amyloid Deposits in Alzheimer Disease," *Cold Spring Harb Perspect Med* 2:1-23, 2012.
Mirra et al., "The Consortium to Establish a Registry for Alzheimer's Disease (CERAD) Part II. Standardization of the neuropathologic assessment of Alzheimer's disease," *Neurology* 41:479-486, Apr. 1991.
Mitkevich et al., "Isomerization of Asp7 leads to increased toxic effect of amyloid-β42 on human neuronal cells," *Cell Death and Disease* 4:2013. (1 page).
The National Institute on Aging et al., "Consensus Recommendations for the Postmortem Diagnosis of Alzheimer's Disease," *Neurobiology of Aging* 18(4):1-2, 1997.
Oakley et al., "Intraneuronal β-Amyloid Aggregates, Neurodegeneration, and Neuron Loss in Transgenic Mice with Five Familial Alzheimer's Disease Mutations: Potential Factors in Amyloid Plaque Formation," *The Journal of Neuroscience* 26(40):10129-10140, Oct. 2006.
Prince et al., "Recent global trends in the prevalence and incidence of dementia, and survival with dementia," *Alzheimer's Research & Therapy* 8:1-13, 2016.
Puzzo et al., "Endogenous Amyloid-β is Necessary for Hippocampal Synaptic Plasticity and Memory," *ANNALS of Neurology* 69(5):819-830, May 2011.
Reissner et al., "Deamidation and isoaspartate formation in proteins: unwanted alterations or surreptitious signals?" *CMLS, Cell. Mol. Life Sci.* 60:1281-1295, 2003.
Rezaei-Ghaleh et al., "Phosphorylation modifies the molecular stability of β-amyloid deposits," *Nature Communications* 7:1-9, Apr. 2016.
Robinson et al., "Controlled Deamidation of Peptides and Proteins: An Experimental Hazard and a Possible Biological Timer," *PNAS* 66(3):753-757, Jul. 1970.
Robinson et al., "Deamidation of Glutaminyl and Asparaginyl Residues in Peptides and Proteins," *Curr Top Cell Regul.* 8:247-95, 1974.
Robinson et al., "Molecular clocks," *PNAS* 98(3):944-949, Jan. 2001.
Roher et al., "Structural Alterations in the Peptide Backbone of β-Amyloid Core Protein May Account for Its Deposition and Stability in Alzheimer's Disease," *The Journal of Biological Chemistry* 268(5):2072-3083, Feb. 1993.
Schlenzig et al., "Pyroglutamate Formation Influences Solubility and Amyloidogenicity of Amyloid Peptides," *Biochemistry* 48:7072-7078, 2009.
Selkoe et al., "The amyloid hypothesis of Alzheimer's disease at 25 years," *EMBO Molecular Medicine* 8(6):595-608, 2016.

Shimizu et al., "Biological Significance of Isoaspartate and Its Repair System," *Biol. Pharm. Bull.* 28(9):1590-1596, 2005.
Shimizu et al., "Isoaspartate Formation and Neurodegeneration in Alzheimer's Disease," *Archives of Biochemistry and Biophysics* 381(2):225-234, Sep. 2000.
Shimizu et al., "Isoaspartate Formation at Position 23 of Amyloid Beta Peptide Enhanced Fibril Formation and Deposited Onto Senile Plaques and Vascular Amyloids in Alzheimer's Disease," *Journal of Neuroscience Research* 70:451-461, 2002.
Stephenson et al., "Succinimide Formation from Aspartyl and Asparaginyl Peptides as a Model for the Spontaneous Degradation of Proteins," *The Journal of Biological Chemistry* 264(11):6164-6170, Apr. 1989.
Sugiki et al., "Site-specific aspartic acid isomerization regulates self-assembly and neurotoxicity of amyloid-β," *Biochemical and Biophysical Research Communications* 441:493-498, Oct. 2013.
Toropygin et al., "The N-domain of angiotensin-converting enzyme specifically hydrolyzes the Arg-5-His-6 bond of Alzheimer's Aβ-(1-16) peptide and its isoAsp-7 analogue with different efficiency as evidenced by quantitative matrix-assisted laser desorption/ionization time-of-flight mass spectrometry," *Rapid Comm. Mass Spectrom.* 22:231-239, 2008.
Tsvetkov et al., "Isomerization of the Asp7 Residue Results in Zinc-Induced Oligomerization of Alzheimer's Disease Amyloid β(1-16) Peptide," *ChemBioChem* 9:1564-1567, 2008.
Tsvetkov et al., "Minimal $Zn^{2+}$ Binding Site of Amyloid-β," *Biophysical Journal* 99:L84-L86, Nov. 2010.
Wakutani et al., "Novel amyloid precursor protein gene missense mutation (D678N) in probable familial Alzheimer's disease," *J Neurol Neurosurg Psychiatry* 75:1039-1042, 2004.
Wohr et al., "Pseudo-Prolines in Peptide Synthesis: Direct Insertion of Serine and Threonine Derived Oxazolidines in Dipeptides," *Tetrahedron Letters* 36(2):3847-3848, 1995.
Wulff et al., "Enhanced Fibril Fragmentation of N-Terminally Truncate4d and Pyroglutamyl-Modified Aβ Peptides," *Angew. Chem. Int. Ed.* 55:5081-5084, 2016.
Xiang et al., "Physiological amyloid-beta clearance in the periphery and its therapeutic potential for Alzheimer's disease," *Acta Neuropathol* 130:487-499, 2015.
Zhang et al., "Atomic and Dynamic Insights into the Beneficial Effect of the 1,4-Naphthoquinon-2-yl-$_L$-tryptophan Inhibitor on Alzheimer's Aβ1-42 Dimer in Terms of Aggregation and Toxicity," *ACS Chem. Neurosci.* 5:148-159, 2014.
Fabian et al., "Synthetic post-translationally modified human Aβ peptide exhibits a markedly increased tendency to form β-pleated sheets *in vitro*," *European Journal of Biochemistry* 221:959-964, 1994.
Shimizu et al., "Biological Significance of Isoaspartate and Its Repair System," *Biological & Pharmaceutical Bulletin* 28(9):1590-1596, 2005.
Shimizu et al., "Isoaspartate Formation and Neurodegeneration in Alzheimer's Disease," *Archives of Biochemistry and Biophysics* 381(2):225-234, 2000.
Zhang et al. "Atomic and Dynamic Insights into the Beneficial Effect of the 1,4-Naphthoquinon-2-yl-L-tryptophan Inhibitor on Alzheimer's Aβ1-42 Dimer in Terms of Aggregation and Toxicity," *ACS Chemical Neuroscience* 5(2):148-159, 2014.
Al-Lazikani et al., "Standard Conformations for the Canonical Structures of Immunoglobins," *J. Mol. Biol.* 273:927-948, 1997.
Ano et al., "Iso-α-acids, Bitter Components of Beer, Prevent Inflammation and Cognitive Decline Induced in a Mouse Model of Alzheimer's Disease," *The Journal of Biological Chemistry* 292(9):3720-3728, Mar. 3, 2017.
Ardestani et al., "Modulation of neuroinflammation and pathology in the 5XFAD mouse model of Alzheimer's Disease using a biased and selective beta-1 adrenergic receptor partial agonist," *Neuropharmacology* 116:371-386, Apr. 2017.
Barbas III et al., "Assembly of combinatorial antibody libraries on phage surfaces: The gene III site," *Proc. Natl. Acad. Sci. USA* 88:7978-7982, Sep. 19, 1991.
Beidler et al., "Cloning and high level expression of a chimeric antibody with specificity for human carcinoembryonic antigen," *J Immunol* 141(11):4053-4060, Dec. 1, 1988.

(56) References Cited

OTHER PUBLICATIONS

Better et al., "*Escherichia coli* Secretion of an Active Chimeric Antibody Fragment," *Science* 240:1041-1043, May 20, 1988.

Bird et al., "Single-Chain Antigen-Binding Proteins," *Science* 242:423-426, Oct. 21, 1988.

Brüggemann et al., "Human antibody production in transgenic mice: expression from 100 kb of the human IgH locus," *Eur. J. Immunol.* 21:1323-1326, 1991.

Cha et al., "Protein-Induced Pluripotent Stem Cells Ameliorate Cognitive Dysfunction and Reduce Aβ Deposition in a Mouse Model of Alzheimer's Disease," *Stem Cells Translational Medicine* 6:293-305, 2017.

Chothia et al., "Canonical Structures for the Hypervariable Regions of Immunoglobulins," *J. Mol. Biol.* 196:901-917, 1987.

Clackson et al., "Making antibody fragments using phage display libraries," *Nature* 352:624-628, Aug. 15, 1991.

Colcher et al., "Single-Chain Antibodies in Pancreatic Cancer," *Annals New York Academy of Science*:263-280.

Cox et al., *The Assay Guidance Manual: Immunoassay Methods*, Eli Lilly & Company and the National Center for Advancing Translational Sciences;, Bethesda, Maryland, 2004, pp. 1-39.

Fuchs et al., "Targeting Recombinant Antibodies to the Surface of *Escherichia coli*: Fusion to a Peptidoglycan Associated Lipoprotein," *Biotechnology* 9:1369-1372, Dec. 1991.

Garrard et al., "$F_{AB}$ Assembly and Enrichment in a Monovalent Phage Display System," *Biotechnology* 9:1373-1377, Dec. 1991.

Gram et al., "*In vitro* selection and affinity maturation of antibodies from a naive combinatorial immunoglobulin library," *Proc. Natl. Acad. Sci. USA* 89:3576-3580, Apr. 1992.

Green et al., "Antigen-specific human monoclonal antibodies from mice engineered with human Ig heavy and light chain YACs," *Nature Genetics* 7:13-21, May 1994.

Griffiths et al., "Human anti-self antibodies with high specificity from phage display libraries," *The EMBO Journal* 12(2):725-734, 1993.

Hawkins et al., "Selection of Phage Antibodies by Binding Affinity Mimicking Affinity Maturation," *J. Mol. Biol.* 226:889-896, 1992.

Holmes et al., "Long-term effects of $A\beta_{42}$ immunisation in Alzheimer's disease: follow-up of a randomised, placebo-controlled phase I trial," *Lancet* 372:216-232, 2008.

Hoogenboom et al., "Multi-subunit proteins on the surface of filamentous phage: methodologies for displaying antibody (Fab) heavy and light chains," *Nucleic Acids Research* 19(15):4133-4137, 1991.

Hsu et al., "Use of Avidin-Biotin-Peroxidase Complex (ABC) in Immunoperoxidase Techniques: A Comparison between ABC and Unlabeled Antibody (PAP) Procedures," *The Journal of Histochemistry and Cytochemistry* 29(4):577-580, 1981.

Huse et al., "Generation of a Large Combinatorial Library of the Immunoglobulin Repertoire in Phage Lambda," *Science* 246:1275-1281, Dec. 8, 1989.

Huston et al., "Protein engineering of antibody binding sites: Recovery of specific activity in an anti-digoxin single-chain Fv analogue produced in *Escherichia coli*," *Proc. Natl. Acad. Sci. USA* 85:5879-5883, Aug. 1988.

Jones et al., "Replacing the complementarity-determining regions in a human antibody with those from a mouse," *Nature* 321:522-525, May 29, 1986.

Kozin et al., "Amyloid-β containing isoaspartate 7 as potential biomarker and drug target in Alzheimer's disease," *Mendeleev Comm.* 26:269-275, 2016.

Liu et al., "Chimeric mouse-human IgG1 antibody that can mediate lysis of cancer cells," *Proc. Natl. Acad. Sci. USA* 84:3439-3443, May 1987.

Liu et al., "Production of a mouse-human chimeric monoclonal antibody to CD20 with potent Fc-dependent biologic activity," *J. Immunol.* 139:3521-3526, 1987.

Lonberg et al., "Antigen-specific human antibodies from mice comprising four distinct genetic modifications," *Nature* 368:856-859, Apr. 28, 1994.

MacPherson et al., "Peripheral administration of the soluble TNF inhibitor XPro1595 modifies brain immune cell profiles, decreases beta-amyloid plaque load, and rescues long-term potentiation in 5xFAD mice," *Neurobiol. Dis.* 102:81-95, Jun. 2017.

Martin, "Protein Sequence and Structure Analysis of Antibody Variable Domains," *Antibody Engineering* 2:33-51, 2010.

Moreth et al., "Passive anti-amyloid immunotherapy in Alzheimer's disease: What are the most promising targets?" *Immunity & Ageing* 10(18):1-9, 2013.

Morrison, "Transfectomas Provide Novel Chimeric Antibodies," *Science* 229:1202-1207, Sep. 20, 1985.

Morrison et al., "Chimeric human antibody molecules: Mouse antigen-binding domains with human constant region domains," *Proc. Natl. Acad. Sci. USA* 81:6851-6855, Nov. 1984.

Nishimura et al., "Recombinant Human-House Chimeric Monoclonal Antibody Specific for Common Acute Lymphocytic Leukemia Antigen," *Cancer Research* 47:999-1005, Feb. 15, 1987.

Orgogozo et al., "Subacute meningoencephalitis in a subset of patients with AD after Aβ42 immunization," *Neurology* 61:46-54, Jul. 2003.

Petersen, "Mild cognitive impairment as a diagnostic entity," *Journal of Internal Medicine* 256:183-194, 2004.

Reiter et al., "Antibody Engineering of Recombinant Fv Immunotoxins for Improved Targeting of Cancer: Disulfide-stabilized Fv Immunotoxins," *Clinical Cancer Research* 2:245-252, Feb. 1996.

Savva et al., "Age, Neuropathology, and Dementia," *N Engl J Med* 360(22):2302-2309, May 28, 2009.

Shaw et al., "Mouse/Human Chimeric Antibodies to a Tumor-Associated Antigen: Biologic Activity of the Four Human IgG Subclasses," *Articles* 80(19):1553-1559, Dec. 7, 1988.

Sun et al., "Chimeric antibody with human constant regions and mouse variable regions directed against carcinoma-associated antigen 17-1A," *Proc. Natl. Acad. Sci. USA* 84:214-218, Jan. 1987.

Torika et al., "Intranasal telmisartan ameliorates brain pathology in five familial Alzheimer's disease mice," *Brain, Behavior, and Immunity* 64:80-90, 2017.

Tuaillon et al., "Human immunoglobulin heavy-chain minilocus recombination in transgenic mice: Gene-segment use in μ and γ transcripts," *Proc. Natl. Acad. Sci. USA* 90:3720-3724, Apr. 1993.

Verhoeyen et al., "Reshaping Human Antibodies: Grafting an Antilysozyme Activity," *Science* 239:1534-1536, Mar. 25, 1988.

Wood et al., "The synthesis and *in vivo* assembly of functional antibodies in yeast," *Nature* 314:446-449, Apr. 4, 1985.

\* cited by examiner

SEQUENCE LISTING

```
<160> NUMBER OF SEQ ID NOS: 68

<210> SEQ ID NO 1
<211> LENGTH: 42
<212> TYPE: PRT
<213> ORGANISM: Artificial Sequence
<220> FEATURE:
<223> OTHER INFORMATION: Amyloid beta 1-42

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40
```

```
<210> SEQ ID NO 2
<211> LENGTH: 40
<212> TYPE: PRT
<213> ORGANISM: Artificial Sequence
<220> FEATURE:
<223> OTHER INFORMATION: Amyloid beta 1-40

<400> SEQUENCE: 2

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 3
<211> LENGTH: 13
<212> TYPE: PRT
<213> ORGANISM: Artificial Sequence
<220> FEATURE:
<223> OTHER INFORMATION: isoD7-Amyloid beta(1-12)Cys
<220> FEATURE:
<221> NAME/KEY: MOD_RES
<222> LOCATION: 7
<223> OTHER INFORMATION: L-IsoAsp

<400> SEQUENCE: 3

Asp Ala Glu Phe Arg His Xaa Ser Gly Tyr Glu Val Cys
1               5                   10

<210> SEQ ID NO 4
<211> LENGTH: 16
<212> TYPE: PRT
<213> ORGANISM: Artificial Sequence
<220> FEATURE:
<223> OTHER INFORMATION: isoD7-Amyloid beta(5-9)repCys
<220> FEATURE:
<221> NAME/KEY: MOD_RES
<222> LOCATION: 3
<223> OTHER INFORMATION: L-IsoAsp
<220> FEATURE:
<221> NAME/KEY: MOD_RES
<222> LOCATION: 8
<223> OTHER INFORMATION: L-IsoAsp
<220> FEATURE:
<221> NAME/KEY: MOD_RES
<222> LOCATION: 13
<223> OTHER INFORMATION: L-IsoAsp

<400> SEQUENCE: 4

Arg His Xaa Ser Gly Arg His Xaa Ser Gly Arg His Xaa Ser Gly Cys
1               5                   10                  15

<210> SEQ ID NO 5
<211> LENGTH: 18
<212> TYPE: PRT
<213> ORGANISM: Artificial Sequence
<220> FEATURE:
<223> OTHER INFORMATION: isoD7-Amyloid beta(1-18)PEG-Biotin
<220> FEATURE:
<221> NAME/KEY: MOD_RES
<222> LOCATION: 7
<223> OTHER INFORMATION: L-IsoAsp
<220> FEATURE:
<221> NAME/KEY: MOD_RES
<222> LOCATION: 18
<223> OTHER INFORMATION: PEG-Biotin

<400> SEQUENCE: 5

Asp Ala Glu Phe Arg His Xaa Ser Gly Tyr Glu Val His His Gln Lys
```

```
                   1               5                  10                  15

Leu Val

<210> SEQ ID NO 6
<211> LENGTH: 18
<212> TYPE: PRT
<213> ORGANISM: Artificial Sequence
<220> FEATURE:
<223> OTHER INFORMATION: Amyloid beta(1-18)PEG-Biotin
<220> FEATURE:
<221> NAME/KEY: MOD_RES
<222> LOCATION: 18
<223> OTHER INFORMATION: PEG-Biotin

<400> SEQUENCE: 6

Asp Ala Glu Phe Arg His Asp Ser Gly Tyr Glu Val His His Gln Lys
1               5                   10                  15

Leu Val

<210> SEQ ID NO 7
<211> LENGTH: 17
<212> TYPE: PRT
<213> ORGANISM: Artificial Sequence
<220> FEATURE:
<223> OTHER INFORMATION: isod7-Amyloid beta(1-17)
<220> FEATURE:
<221> NAME/KEY: MOD_RES
<222> LOCATION: 7
<223> OTHER INFORMATION: D-IsoAsp

<400> SEQUENCE: 7

Asp Ala Glu Phe Arg His Xaa Ser Gly Tyr Glu Val His His Gln Lys
1               5                   10                  15

Leu

<210> SEQ ID NO 8
<211> LENGTH: 18
<212> TYPE: PRT
<213> ORGANISM: Artificial Sequence
<220> FEATURE:
<223> OTHER INFORMATION: Amyloid beta(1-18)

<400> SEQUENCE: 8

Asp Ala Glu Phe Arg His Asp Ser Gly Tyr Glu Val His His Gln Lys
1               5                   10                  15

Leu Val

<210> SEQ ID NO 9
<211> LENGTH: 17
<212> TYPE: PRT
<213> ORGANISM: Artificial Sequence
<220> FEATURE:
<223> OTHER INFORMATION: K11 LCDR1

<400> SEQUENCE: 9

Lys Ser Ser Gln Ser Leu Leu Asn Ser Arg Asn Arg Lys Asn Tyr Leu
1               5                   10                  15

Ala

<210> SEQ ID NO 10
<211> LENGTH: 17
<212> TYPE: PRT
<213> ORGANISM: Artificial Sequence
<220> FEATURE:
<223> OTHER INFORMATION: K11 LCDR1 consensus
```

-continued

```
<220> FEATURE:
<221> NAME/KEY: VARIANT
<222> LOCATION: 9
<223> OTHER INFORMATION: S or R
<220> FEATURE:
<221> NAME/KEY: VARIANT
<222> LOCATION: 11
<223> OTHER INFORMATION: N or T

<400> SEQUENCE: 10

Lys Ser Ser Gln Ser Leu Leu Asn Xaa Arg Xaa Arg Lys Asn Tyr Leu
1               5                   10                  15

Ala

<210> SEQ ID NO 11
<211> LENGTH: 7
<212> TYPE: PRT
<213> ORGANISM: Artificial Sequence
<220> FEATURE:
<223> OTHER INFORMATION: K11 LCDR2

<400> SEQUENCE: 11

Trp Ala Ser Thr Arg Asp Ser
1               5

<210> SEQ ID NO 12
<211> LENGTH: 7
<212> TYPE: PRT
<213> ORGANISM: Artificial Sequence
<220> FEATURE:
<223> OTHER INFORMATION: K11 LCDR2 consensus
<220> FEATURE:
<221> NAME/KEY: VARIANT
<222> LOCATION: 6
<223> OTHER INFORMATION: D or E

<400> SEQUENCE: 12

Trp Ala Ser Thr Arg Xaa Ser
1               5

<210> SEQ ID NO 13
<211> LENGTH: 8
<212> TYPE: PRT
<213> ORGANISM: Artificial Sequence
<220> FEATURE:
<223> OTHER INFORMATION: K11 LCDR3

<400> SEQUENCE: 13

Lys Gln Ser Tyr Asn Leu Arg Thr
1               5

<210> SEQ ID NO 14
<211> LENGTH: 10
<212> TYPE: PRT
<213> ORGANISM: Artificial Sequence
<220> FEATURE:
<223> OTHER INFORMATION: K11 HCDR1

<400> SEQUENCE: 14

Gly Phe Ser Leu Thr Ser Tyr Gly Val His
1               5                   10

<210> SEQ ID NO 15
<211> LENGTH: 16
<212> TYPE: PRT
<213> ORGANISM: Artificial Sequence
<220> FEATURE:
<223> OTHER INFORMATION: K11 HCDR2
```

```
<400> SEQUENCE: 15

Ala Leu Trp Ala Ser Gly Asn Thr Asp Tyr Ser Ser Thr Leu Met Ser
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: K11 HCDR2 consensus
<220> FEATURE:
<221> NAME/KEY: VARIANT
<222> LOCATION: 1
<223> OTHER INFORMATION: A or V
<220> FEATURE:
<221> NAME/KEY: VARIANT
<222> LOCATION: 7
<223> OTHER INFORMATION: N or R
<220> FEATURE:
<221> NAME/KEY: VARIANT
<222> LOCATION: 11
<223> OTHER INFORMATION: S or N
<220> FEATURE:
<221> NAME/KEY: VARIANT
<222> LOCATION: 13
<223> OTHER INFORMATION: T or A

<400> SEQUENCE: 16

Xaa Leu Trp Ala Ser Gly Xaa Thr Asp Tyr Xaa Ser Xaa Leu Met Ser
1               5                   10                  15

<210> SEQ ID NO 17
<211> LENGTH: 12
<212> TYPE: PRT
<213> ORGANISM: Artificial Sequence
<220> FEATURE:
<223> OTHER INFORMATION: K11 HCDR3

<400> SEQUENCE: 17

Asp Arg Gly Ile Leu Thr Gly Gly Tyr Phe Asp Val
1               5                   10

<210> SEQ ID NO 18
<211> LENGTH: 12
<212> TYPE: PRT
<213> ORGANISM: Artificial Sequence
<220> FEATURE:
<223> OTHER INFORMATION: K11 HCDR3 consensus
<220> FEATURE:
<221> NAME/KEY: VARIANT
<222> LOCATION: 5
<223> OTHER INFORMATION: L, T or M

<400> SEQUENCE: 18

Asp Arg Gly Ile Xaa Thr Gly Gly Tyr Phe Asp Val
1               5                   10

<210> SEQ ID NO 19
<211> LENGTH: 112
<212> TYPE: PRT
<213> ORGANISM: Artificial Sequence
<220> FEATURE:
<223> OTHER INFORMATION: K11 VL

<400> SEQUENCE: 19

Asp Ile Val Met Ser Gln Ser Pro Thr Ser Leu Ala Val Ser Ala Gly
1               5                   10                  15

Glu Lys Val Thr Met Ser Cys Lys Ser Ser Gln Ser Leu Leu Asn Ser
```

```
                    20                  25                  30

Arg Asn Arg Lys Asn Tyr Leu Ala Trp Tyr Gln Gln Lys Pro Gly Gln
            35                  40                  45

Ser Pro Lys Leu Leu Ile Tyr Trp Ala Ser Thr Arg Asp Ser Gly Val
        50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Lys Gln
                    85                  90                  95

Ser Tyr Asn Leu Arg Thr Phe Gly Gly Gly Thr Lys Leu Glu Ile Lys
                100                 105                 110
```

<210> SEQ ID NO 20
<211> LENGTH: 120
<212> TYPE: PRT
<213> ORGANISM: Artificial Sequence
<220> FEATURE:
<223> OTHER INFORMATION: K11 VH

<400> SEQUENCE: 20

```
Gln Val Gln Leu Lys Glu Ser Gly Pro Gly Leu Val Ala Pro Ser Gln
 1               5                  10                  15

Ser Leu Ser Ile Thr Cys Thr Val Ser Gly Phe Ser Leu Thr Ser Tyr
                20                  25                  30

Gly Val His Trp Val Arg Gln Pro Pro Gly Lys Gly Leu Glu Trp Leu
            35                  40                  45

Gly Ala Leu Trp Ala Ser Gly Asn Thr Asp Tyr Ser Ser Ala Leu Met
        50                  55                  60

Ser Arg Leu Ser Ile Ser Lys Asp Asn Ser Lys Ser Gln Val Phe Leu
 65                  70                  75                  80

Lys Met Asn Ser Leu Gln Thr Asp Asp Thr Ala Met Tyr Tyr Cys Ala
                85                  90                  95

Arg Asp Arg Gly Ile Met Thr Gly Gly Tyr Phe Asp Val Trp Gly Ala
                100                 105                 110

Gly Thr Thr Val Thr Val Ser Ser
        115                 120
```

<210> SEQ ID NO 21
<211> LENGTH: 219
<212> TYPE: PRT
<213> ORGANISM: Artificial Sequence
<220> FEATURE:
<223> OTHER INFORMATION: K11 LC

<400> SEQUENCE: 21

```
Asp Ile Val Met Ser Gln Ser Pro Thr Ser Leu Ala Val Ser Ala Gly
 1               5                  10                  15

Glu Lys Val Thr Met Ser Cys Lys Ser Ser Gln Ser Leu Leu Asn Ser
                20                  25                  30

Arg Asn Arg Lys Asn Tyr Leu Ala Trp Tyr Gln Gln Lys Pro Gly Gln
            35                  40                  45

Ser Pro Lys Leu Leu Ile Tyr Trp Ala Ser Thr Arg Asp Ser Gly Val
        50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Lys Gln
                85                  90                  95
```

```
Ser Tyr Asn Leu Arg Thr Phe Gly Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215

<210> SEQ ID NO 22
<211> LENGTH: 444
<212> TYPE: PRT
<213> ORGANISM: Artificial Sequence
<220> FEATURE:
<223> OTHER INFORMATION: K11 HC

<400> SEQUENCE: 22

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Pro Pro Gly Lys Gly Leu Glu Trp Leu
        35                  40                  45

Gly Ala Leu Trp Ala Ser Gly Asn Thr Asp Tyr Ser Ser Thr Leu Met
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Tyr Cys Ala
                85                  90                  95

Arg Asp Arg Gly Ile Leu Thr Gly Gly Tyr Phe Asp Val Trp Gly Ala
            100                 105                 110

Gly Thr Thr Val Thr Val Ser Ser Ala Lys Thr Thr Pro Pro Ser Val
        115                 120                 125

Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Pro Ser
            180                 185                 190

Ser Thr Trp Pro Ser Glu Thr Val Thr Cys Asn Val Ala His Pro Ala
        195                 200                 205

Ser Ser Thr Lys Val Asp Lys Lys Ile Val Pro Arg Asp Cys Gly Cys
    210                 215                 220

Lys Pro Cys Ile Cys Thr Val Pro Glu Val Ser Ser Val Phe Ile Phe
225                 230                 235                 240
```

```
Pro Pro Lys Pro Lys Asp Val Leu Thr Ile Thr Leu Thr Pro Lys Val
            245                 250                 255

Thr Cys Val Val Val Asp Ile Ser Lys Asp Asp Pro Glu Val Gln Phe
            260                 265                 270

Ser Trp Phe Val Asp Asp Val Glu Val His Thr Ala Gln Thr Gln Pro
            275                 280             285

Arg Glu Glu Gln Phe Asn Ser Thr Phe Arg Ser Val Ser Glu Leu Pro
    290                 295                 300

Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr
                325                 330                 335

Lys Gly Arg Pro Lys Ala Pro Gln Val Tyr Thr Ile Pro Pro Pro Lys
            340                 345                 350

Glu Gln Met Ala Lys Asp Lys Val Ser Leu Thr Cys Met Ile Thr Asp
            355                 360                 365

Phe Phe Pro Glu Asp Ile Thr Val Glu Trp Gln Trp Asn Gly Gln Pro
370                 375                 380

Ala Glu Asn Tyr Lys Asn Thr Gln Pro Ile Met Asp Thr Asp Gly Ser
385                 390                 395                 400

Tyr Phe Val Tyr Ser Lys Leu Asn Val Gln Lys Ser Asn Trp Glu Ala
                405                 410                 415

Gly Asn Thr Phe Thr Cys Ser Val Leu His Glu Gly Leu His Asn His
                420                 425                 430

His Thr Glu Lys Ser Leu Ser His Ser Pro Gly Lys
            435                 440

<210> SEQ ID NO 23
<211> LENGTH: 336
<212> TYPE: DNA
<213> ORGANISM: Artificial Sequence
<220> FEATURE:
<223> OTHER INFORMATION: K11 VL DNA

<400> SEQUENCE: 23
gacattgtga tgtcacagtc tccaacctcc ctggctgtgt cagcaggaga gaaggtcacc     60
atgagctgca atccagtca gagtctactc aacagtagaa accgaaagaa ctacttggct    120
tggtaccagc agaaaccagg gcagtctcct aaactgctga tctactgggc atccactagg    180
gattctgggg tccctgatcg cttcacaggc agtggatctg ggacagattt cactctcacc    240
atcagcagtg tgcaggctga agacctggca gtttattact gcaagcaatc ttataatctt    300
cggacgttcg gtggaggcac caagctggaa atcaaa                              336

<210> SEQ ID NO 24
<211> LENGTH: 360
<212> TYPE: DNA
<213> ORGANISM: Artificial Sequence
<220> FEATURE:
<223> OTHER INFORMATION: K11 VH DNA

<400> SEQUENCE: 24
caggtgcagc tgaaggagtc aggacctggc ctggtggcgc cctcacagag cctgtccatc     60
acttgcactg tctctggatt ttcattaacc agctatggtg tacactgggt tcgccagcct    120
ccaggaaagg gtctggagtg gctgggagca ctatgggcta gtggaaacac agattatagt    180
tcgactctca gtccagact gagcatcagc aaagacaact ccaagagcca gttttctta    240
```

<210> SEQ ID NO 25
<211> LENGTH: 657
<212> TYPE: DNA
<213> ORGANISM: Artificial Sequence
<220> FEATURE:
<223> OTHER INFORMATION: K11 LC DNA

<400> SEQUENCE: 25

```
gacattgtga tgtcacagtc tccaacctcc ctggctgtgt cagcaggaga gaaggtcacc      60
atgagctgca aatccagtca gagtctactc aacagtagaa accgaaagaa ctacttggct     120
tggtaccagc agaaaccagg gcagtctcct aaactgctga tctactgggc atccactagg     180
gattctgggg tccctgatcg cttcacaggc agtggatctg ggacagattt cactctcacc     240
atcagcagtg tgcaggctga agacctggca gtttattact gcaagcaatc ttataatctt     300
cggacgttcg gtggaggcac caagctggaa atcaaacggg ctgatgctgc accaactgta     360
tccatcttcc caccatccag tgagcagtta acatctggag gtgcctcagt cgtgtgcttc     420
ttgaacaact tctaccccaa agacatcaat gtcaagtgga gattgatgg cagtgaacga      480
caaaatggcg tcctgaacag ttggactgat caggacagca agacagcac ctacagcatg      540
agcagcaccc tcacgttgac caaggacgag tatgaacgca taacagcta tacctgtgag     600
gccactcaca gacatcaac ttcacccatt gtcaagagct caacaggaa tgagtgt        657
```

<210> SEQ ID NO 26
<211> LENGTH: 1332
<212> TYPE: DNA
<213> ORGANISM: Artificial Sequence
<220> FEATURE:
<223> OTHER INFORMATION: K11 HC DNA

<400> SEQUENCE: 26

```
caggtgcagc tgaaggagtc aggacctggc ctggtggcgc cctcacagag cctgtccatc      60
acttgcactg tctctggatt ttcattaacc agctatggtg tacactgggt tcgccagcct     120
ccaggaaagg gtctggagtg gctgggagca ctatgggcta gtggaaacac agattatagt     180
tcgactctca gtccagact gagcatcagc aaagacaact ccaagagcca gttttcttta     240
aaaatgaaca gtctgcaaac tgatgacaca gccatgtatt actgtgccag agatcggggg     300
attctgacgg agggtacttc gatgtctgg ggcgcaggga ccacggtcac cgtctcctca     360
gccaaaacga cacccccatc tgtctatcca ctggcccctg gatctgctgc ccaaactaac     420
tccatggtga ccctgggatg cctggtcaag ggctatttcc ctgagccagt gacagtgacc     480
tggaactctg gatccctgtc cagcggtgtg cacaccttcc cagctgtcct gcagtctgac     540
ctctacactc tgagcagctc agtgactgtc ccctccagcc ctcggcccag cgagaccgtc     600
acctgcaacg ttgcccaccc ggccagcagc accaaggtgg acaagaaaat tgtgcccagg     660
gattgtggtt gtaagccttg catatgtaca gtcccagaag tatcatctgt cttcatcttc     720
cccccaaagc ccaaggatgt cctcaccatt actctgactc ctaaggtcac gtgtgttgtg     780
gtagacatca gcaaggatga tcccgaggtc cagttcagct ggtttgtaga tgatgtggag     840
gtgcacacag ctcagacgca acccgggag gagcagttca acagcacttt ccgctcagtc     900
agtgaacttc ccatcatgca ccaggactgg ctcaatggca aggagttcaa atgcagggtc     960
aacagtgcag cttttcctg ccccatcgag aaaaccatat ccaaaaccaa aggcagaccg    1020
```

```
aaggctccac aggtgtacac cattccacct cccaaggagc agatggccaa ggataaagtc    1080
agtctgacct gcatgataac agacttcttc cctgaagaca taacagtgga gtggcagtgg    1140
aatgggcagc cagcggagaa ctacaagaac actcagccca tcatgaacac gaatggctct    1200
tacttcgtct acagcaagct caatgtgcag aagagcaact gggaggcagg aaatactttc    1260
acctgctctg tgttacatga gggcctgcac aaccaccata ctgagaagag cctctcccac    1320
tctcctggta aa                                                        1332
```

<210> SEQ ID NO 27
<211> LENGTH: 17
<212> TYPE: PRT
<213> ORGANISM: Artificial Sequence
<220> FEATURE:
<223> OTHER INFORMATION: K119 LCDR1

<400> SEQUENCE: 27

```
Lys Ser Ser Gln Ser Leu Phe Asn Ser Arg Thr Arg Lys Asn Tyr Val
1               5                   10                  15

Ala
```

<210> SEQ ID NO 28
<211> LENGTH: 17
<212> TYPE: PRT
<213> ORGANISM: Artificial Sequence
<220> FEATURE:
<223> OTHER INFORMATION: K119 LCDR1 consensus
<220> FEATURE:
<221> NAME/KEY: VARIANT
<222> LOCATION: 5
<223> OTHER INFORMATION: S or N
<220> FEATURE:
<221> NAME/KEY: VARIANT
<222> LOCATION: 7
<223> OTHER INFORMATION: F or L
<220> FEATURE:
<221> NAME/KEY: VARIANT
<222> LOCATION: 16
<223> OTHER INFORMATION: V or L

<400> SEQUENCE: 28

```
Lys Ser Ser Gln Xaa Leu Xaa Asn Ser Arg Thr Arg Lys Asn Tyr Xaa
1               5                   10                  15

Ala
```

<210> SEQ ID NO 29
<211> LENGTH: 7
<212> TYPE: PRT
<213> ORGANISM: Artificial Sequence
<220> FEATURE:
<223> OTHER INFORMATION: K119 LCDR2

<400> SEQUENCE: 29

```
Trp Ala Ser Thr Arg Glu Ser
1               5
```

<210> SEQ ID NO 30
<211> LENGTH: 8
<212> TYPE: PRT
<213> ORGANISM: Artificial Sequence
<220> FEATURE:
<223> OTHER INFORMATION: K119 LCDR3

<400> SEQUENCE: 30

```
Lys Gln Ser Tyr Asn Leu Arg Ala
1               5
```

```
1               5
```

```
<210> SEQ ID NO 31
<211> LENGTH: 8
<212> TYPE: PRT
<213> ORGANISM: Artificial Sequence
<220> FEATURE:
<223> OTHER INFORMATION: K119 LCDR3 consensus
<220> FEATURE:
<221> NAME/KEY: VARIANT
<222> LOCATION: 1
<223> OTHER INFORMATION: K or M
<220> FEATURE:
<221> NAME/KEY: VARIANT
<222> LOCATION: 8
<223> OTHER INFORMATION: A or T

<400> SEQUENCE: 31

Xaa Gln Ser Tyr Asn Leu Arg Xaa
1               5
```

```
<210> SEQ ID NO 32
<211> LENGTH: 10
<212> TYPE: PRT
<213> ORGANISM: Artificial Sequence
<220> FEATURE:
<223> OTHER INFORMATION: K119 HCDR1

<400> SEQUENCE: 32

Gly Phe Thr Phe Thr Asp Tyr Tyr Met Ser
1               5                   10
```

```
<210> SEQ ID NO 33
<211> LENGTH: 10
<212> TYPE: PRT
<213> ORGANISM: Artificial Sequence
<220> FEATURE:
<223> OTHER INFORMATION: K119 HCDR1 consensus
<220> FEATURE:
<221> NAME/KEY: VARIANT
<222> LOCATION: 5
<223> OTHER INFORMATION: T or S
<220> FEATURE:
<221> NAME/KEY: VARIANT
<222> LOCATION: 10
<223> OTHER INFORMATION: S or N

<400> SEQUENCE: 33

Gly Phe Thr Phe Xaa Asp Tyr Tyr Met Xaa
1               5                   10
```

```
<210> SEQ ID NO 34
<211> LENGTH: 19
<212> TYPE: PRT
<213> ORGANISM: Artificial Sequence
<220> FEATURE:
<223> OTHER INFORMATION: K119 HCDR2

<400> SEQUENCE: 34

Phe Ile Arg Asn Lys Ala Asn Gly Tyr Thr Thr Glu Tyr Ser Ala Ser
1               5                   10                  15

Val Lys Gly
```

```
<210> SEQ ID NO 35
<211> LENGTH: 8
<212> TYPE: PRT
<213> ORGANISM: Artificial Sequence
<220> FEATURE:
<223> OTHER INFORMATION: K119 HCDR3
```

```
<400> SEQUENCE: 35

Asp Ile Pro Thr Ile Met Asp Tyr
1               5

<210> SEQ ID NO 36
<211> LENGTH: 112
<212> TYPE: PRT
<213> ORGANISM: Artificial Sequence
<220> FEATURE:
<223> OTHER INFORMATION: K119 VL

<400> SEQUENCE: 36

Asp Ile Val Met Ser Gln Ser Pro Ser Ser Leu Ala Val Ser Ala Gly
1               5                   10                  15

Glu Lys Ala Thr Met Ser Cys Lys Ser Ser Gln Ser Leu Phe Asn Ser
            20                  25                  30

Arg Thr Arg Lys Asn Tyr Val Ala Trp Leu Gln Gln Lys Pro Gly Gln
        35                  40                  45

Ser Pro Lys Leu Leu Ile Ser Trp Ala Ser Thr Arg Glu Ser Gly Val
    50                  55                  60

Pro Asp Arg Phe Thr Gly Ser Gly Ser Gly Thr Asp Phe Ala Leu Thr
65                  70                  75                  80

Ile Thr Asn Val Gln Ala Glu Asp Leu Ala Val Tyr Tyr Cys Lys Gln
                85                  90                  95

Ser Tyr Asn Leu Arg Ala Phe Gly Gly Gly Thr Lys Leu Glu Ile Thr
            100                 105                 110

<210> SEQ ID NO 37
<211> LENGTH: 119
<212> TYPE: PRT
<213> ORGANISM: Artificial Sequence
<220> FEATURE:
<223> OTHER INFORMATION: K119 VH

<400> SEQUENCE: 37

Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Ala Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Thr Glu Asp Ser Ala Thr Tyr
                85                  90                  95

Tyr Cys Thr Arg Asp Ile Pro Thr Ile Met Asp Tyr Trp Gly Gln Gly
            100                 105                 110

Thr Ser Val Thr Val Ser Ser
        115

<210> SEQ ID NO 38
<211> LENGTH: 219
<212> TYPE: PRT
<213> ORGANISM: Artificial Sequence
<220> FEATURE:
<223> OTHER INFORMATION: K119 LC
```

<400> SEQUENCE: 38

```
Asp Ile Val Met Ser Gln Ser Pro Ser Leu Ala Val Ser Ala Gly
1               5                   10                  15

Glu Lys Ala Thr Met Ser Cys Lys Ser Ser Gln Ser Leu Phe Asn Ser
            20                  25                  30

Arg Thr Arg Lys Asn Tyr Val Ala Trp Leu Gln Gln Lys Pro Gly Gln
        35                  40                  45

Ser Pro Lys Leu Leu Ile Ser Trp Ala Ser Thr Arg Glu Ser Gly Val
    50                  55                  60

Pro Asp Arg Phe Thr Gly Ser Gly Ser Gly Thr Asp Phe Ala Leu Thr
65                  70                  75                  80

Ile Thr Asn Val Gln Ala Glu Asp Leu Ala Val Tyr Tyr Cys Lys Gln
                85                  90                  95

Ser Tyr Asn Leu Arg Ala Phe Gly Gly Gly Thr Lys Leu Glu Ile Thr
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215
```

<210> SEQ ID NO 39
<211> LENGTH: 449
<212> TYPE: PRT
<213> ORGANISM: Artificial Sequence
<220> FEATURE:
<223> OTHER INFORMATION: K119 HC

<400> SEQUENCE: 39

```
Glu Val Lys Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Ser Trp Val Arg Gln Pro Pro Gly Lys Ala Leu Glu Trp Leu
        35                  40                  45

Gly Phe Ile Arg Asn Lys Ala Asn Gly Tyr Thr Thr Glu Tyr Ser Ala
    50                  55                  60

Ser Val Lys Gly Arg Phe Thr Ile Ser Arg Asp Asn Ser Gln Ser Ile
65                  70                  75                  80

Leu Tyr Leu Gln Met Asn Thr Leu Arg Thr Glu Asp Ser Ala Thr Tyr
                85                  90                  95

Tyr Cys Thr Arg Asp Ile Pro Thr Ile Met Asp Tyr Trp Gly Gln Gly
            100                 105                 110

Thr Ser Val Thr Val Ser Ser Ala Lys Thr Thr Ala Pro Ser Val Tyr
        115                 120                 125

Pro Leu Ala Pro Val Cys Gly Asp Thr Thr Gly Ser Ser Val Thr Leu
```

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Thr Ser Ser
            180                 185                 190

Thr Trp Pro Ser Gln Ser Ile Thr Cys Asn Val Ala His Pro Ala Ser
            195                 200                 205

Ser Thr Lys Val Asp Lys Lys Ile Glu Pro Arg Gly Pro Thr Ile Lys
        210                 215                 220

Pro Cys Pro Pro Cys Lys Cys Pro Ala Pro Asn Leu Leu Gly Gly Pro
225                 230                 235                 240

Ser Val Phe Ile Phe Pro Pro Lys Ile Lys Asp Val Leu Met Ile Ser
                245                 250                 255

Leu Ser Pro Ile Val Thr Cys Val Val Val Asp Val Ser Glu Asp Asp
            260                 265                 270

Pro Asp Val Gln Ile Ser Trp Phe Val Asn Asn Val Glu Val His Thr
        275                 280                 285

Ala Gln Thr Gln Thr His Arg Glu Asp Tyr Asn Ser Thr Leu Arg Val
290                 295                 300

Val Ser Ala Leu Pro Ile Gln His Gln Asp Trp Met Ser Gly Lys Glu
305                 310                 315                 320

Phe Lys Cys Lys Val Asn Asn Lys Asp Leu Pro Ala Pro Ile Glu Arg
                325                 330                 335

Thr Ile Ser Lys Pro Lys Gly Ser Val Arg Ala Pro Gln Val Tyr Val
            340                 345                 350

Leu Pro Pro Pro Glu Glu Glu Met Thr Lys Lys Gln Val Thr Leu Thr
        355                 360                 365

Cys Met Val Thr Asp Phe Met Pro Glu Asp Ile Tyr Val Glu Trp Thr
370                 375                 380

Asn Asn Gly Lys Thr Glu Leu Asn Tyr Lys Asn Thr Glu Pro Val Leu
385                 390                 395                 400

Asp Ser Asp Gly Ser Tyr Phe Met Tyr Ser Lys Leu Arg Val Glu Lys
                405                 410                 415

Lys Asn Trp Val Glu Arg Asn Ser Tyr Ser Cys Ser Val Val His Glu
            420                 425                 430

Gly Leu His Asn His His Thr Thr Lys Ser Phe Ser Arg Thr Pro Gly
        435                 440                 445

Lys

<210> SEQ ID NO 40
<211> LENGTH: 336
<212> TYPE: DNA
<213> ORGANISM: Artificial Sequence
<220> FEATURE:
<223> OTHER INFORMATION: K119 VL DNA

<400> SEQUENCE: 40
gacattgtga tgtcacagtc tccatcctcc ctggctgtgt cagcaggaga gaaggccact    60
atgagctgca aatccagtca gagtctgttc aacagtagaa cccgaaagaa ctacgtggct   120
tggctccagc agaaaccagg gcagtctcct aaactactga tctcctgggc atccactagg   180
gaatctgggg tccctgatcg cttcacaggc agtggatctg ggacagattt cgctctcacc   240

```
atcaccaatg tgcaggctga agacctggca gtttattact gcaagcaatc ttataatctt    300
cgggcgttcg gtggaggcac caagctggaa atcaca                              336

<210> SEQ ID NO 41
<211> LENGTH: 357
<212> TYPE: DNA
<213> ORGANISM: Artificial Sequence
<220> FEATURE:
<223> OTHER INFORMATION: K119 VH DNA

<400> SEQUENCE: 41
gaggtgaagc tggtggagtc tggaggaggc ttggtacagc ctgggggttc tctgagactc     60
tcctgtgcaa cttctgggtt caccttcact gattattata tgagctgggt ccgccagcct    120
ccaggaaagg cacttgagtg gttgggtttt attagaaaca agctaatgg ttatacaaca     180 gagtacagtg catctgtgaa gggtcggttc accatctcca gataattc ccaaagcatc      240 ctctatcttc aaatgaacac cctgagaact gaggacagtg ccacttatta ctgtacaaga    300
gatatcccca ctatcatgga ctactggggt caaggaacct cagtcaccgt ctcctca       357

<210> SEQ ID NO 42
<211> LENGTH: 657
<212> TYPE: DNA
<213> ORGANISM: Artificial Sequence
<220> FEATURE:
<223> OTHER INFORMATION: K119 LC DNA

<400> SEQUENCE: 42
gacattgtga tgtcacagtc tccatcctcc ctggctgtgt cagcaggaga gaaggccact     60
atgagctgca atccagtca gagtctgttc aacagtagaa cccgaaagaa ctacgtggct    120
tggctccagc agaaaccagg gcagtctcct aaactactga tctcctgggc atccactagg    180
gaatctgggg tccctgatcg cttcacaggc agtggatctg ggacagattt cgctctcacc    240
atcaccaatg tgcaggctga agacctggca gtttattact gcaagcaatc ttataatctt    300
cgggcgttcg gtggaggcac caagctggaa atcacacggg ctgatgctgc accaactgta    360
tccatcttcc caccatccag tgagcagtta acatctggag gtgcctcagt cgtgtgcttc    420
ttgaacaact ctaccccaa agacatcaat gtcaagtgga gattgatgg cagtgaacga     480 caaaatggcg tcctgaacag ttggactgat caggacagca agacagcac ctacagcatg      540 agcagcaccc tcacgttgac caaggacgag tatgaacgac ataacagcta cctgtgagag    600
gccactcaca agacatcaac ttcacccatt gtcaagagct caacaggaa tgagtgt        657

<210> SEQ ID NO 43
<211> LENGTH: 1347
<212> TYPE: DNA
<213> ORGANISM: Artificial Sequence
<220> FEATURE:
<223> OTHER INFORMATION: K119 HC DNA

<400> SEQUENCE: 43
gaggtgaagc tggtggagtc tggaggaggc ttggtacagc ctgggggttc tctgagactc     60
tcctgtgcaa cttctgggtt caccttcact gattattata tgagctgggt ccgccagcct    120
ccaggaaagg cacttgagtg gttgggtttt attagaaaca agctaatgg ttatacaaca     180 gagtacagtg catctgtgaa gggtcggttc accatctcca gataattc ccaaagcatc      240 ctctatcttc aaatgaacac cctgagaact gaggacagtg ccacttatta ctgtacaaga    300
gatatcccca ctatcatgga ctactggggt caaggaacct cagtcaccgt ctcctcagcc    360
```

```
aaaacaacag ccccatcggt ctatccactg gcccctgtgt gtggagatac aactggctcc    420
tcggtgactc taggatgcct ggtcaagggt tatttccctg agccagtgac cttgacctgg    480
aactctggat ccctgtccag tggtgtgcac accttcccag ctgtcctgca gtctgacctc    540
tacaccctca gcagctcagt gactgtaacc tcgagcacct ggcccagcca gtccatcacc    600
tgcaatgtgg cccacccggc aagcagcacc aaggtggaca gaaaattga gcccagaggg    660 cccacaatca agccctgtcc tccatgcaaa tgcccagcac ctaacctctt gggtggacca    720
tccgtcttca tcttccctcc aaagatcaag gatgtactca tgatctccct gagccccata    780
gtcacatgtg tggtggtgga tgtgagcgag gatgacccag atgtccagat cagctggttt    840
gtgaacaacg tggaagtaca cacagctcag acacaaaccc atagagagga ttacaacagt    900
actctccggg tggtcagtgc cctccccatc cagcaccagg actggatgag tggcaaggag    960
ttcaaatgca aggtcaacaa caaagacctc ccagcgccca tcgagagaac catctcaaaa   1020
cccaaagggt cagtaagagc tccacaggta tatgtcttgc ctccaccaga agaagagatg   1080
actaagaaac aggtcactct gacctgcatg gtcacagact tcatgcctga agacatttac   1140
gtggagtgga ccaacaacgg gaaaacagag ctaaactaca agaacactga accagtcctg   1200
gactctgatg gttcttactt catgtacagc aagctgagag tggaaaagaa gaactgggtg   1260
gaaagaaata gctactcctg ttcagtggtc acgagggtc tgcacaatca ccacacgact   1320
aagagcttct cccggactcc gggtaaa                                       1347

<210> SEQ ID NO 44
<211> LENGTH: 18
<212> TYPE: PRT
<213> ORGANISM: Artificial Sequence
<220> FEATURE:
<223> OTHER INFORMATION: isoD7-Amyloid beta(1-18)
<220> FEATURE:
<221> NAME/KEY: MOD_RES
<222> LOCATION: 7
<223> OTHER INFORMATION: L-IsoAsp

<400> SEQUENCE: 44

Asp Ala Glu Phe Arg His Xaa Ser Gly Tyr Glu Val His His Gln Lys
1               5                   10                  15

Leu Val

<210> SEQ ID NO 45
<211> LENGTH: 40
<212> TYPE: PRT
<213> ORGANISM: Artificial Sequence
<220> FEATURE:
<223> OTHER INFORMATION: isoD7-Amyloid beta(1-40)
<220> FEATURE:
<221> NAME/KEY: MOD_RES
<222> LOCATION: 7
<223> OTHER INFORMATION: L-IsoAsp

<400> SEQUENCE: 45

Asp Ala Glu Phe Arg His Xaa Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 46
```

```
<211> LENGTH: 18
<212> TYPE: PRT
<213> ORGANISM: Artificial Sequence
<220> FEATURE:
<223> OTHER INFORMATION: isoD7-3nitroY10-Amyloid beta(1-18)
<220> FEATURE:
<221> NAME/KEY: MOD_RES
<222> LOCATION: 7
<223> OTHER INFORMATION: L-IsoAsp
<220> FEATURE:
<221> NAME/KEY: MOD_RES
<222> LOCATION: 10
<223> OTHER INFORMATION: 3-Nitrotyrosine

<400> SEQUENCE: 46

Asp Ala Glu Phe Arg His Xaa Ser Gly Xaa Glu Val His His Gln Lys
1               5                   10                  15

Leu Val

<210> SEQ ID NO 47
<211> LENGTH: 16
<212> TYPE: PRT
<213> ORGANISM: Artificial Sequence
<220> FEATURE:
<221> NAME/KEY: MOD_RES
<222> LOCATION: 1
<223> OTHER INFORMATION: L-pyroglutamate
<220> FEATURE:
<223> OTHER INFORMATION: pE3-Amyloid beta(3-18)

<400> SEQUENCE: 47

Xaa Phe Arg His Asp Ser Gly Tyr Glu Val His His Gln Lys Leu Val
1               5                   10                  15

<210> SEQ ID NO 48
<211> LENGTH: 16
<212> TYPE: PRT
<213> ORGANISM: Artificial Sequence
<220> FEATURE:
<221> NAME/KEY: MOD_RES
<222> LOCATION: 1
<223> OTHER INFORMATION: L-pyroglutamate
<220> FEATURE:
<223> OTHER INFORMATION: pE3-isoD7-Amyloid beta(3-18)
<220> FEATURE:
<221> NAME/KEY: MOD_RES
<222> LOCATION: 5
<223> OTHER INFORMATION: L-IsoAsp

<400> SEQUENCE: 48

Xaa Phe Arg His Xaa Ser Gly Tyr Glu Val His His Gln Lys Leu Val
1               5                   10                  15

<210> SEQ ID NO 49
<211> LENGTH: 18
<212> TYPE: PRT
<213> ORGANISM: Artificial Sequence
<220> FEATURE:
<223> OTHER INFORMATION: isoD7-phosphoSer8-Amyloid beta(1-18)
<220> FEATURE:
<221> NAME/KEY: MOD_RES
<222> LOCATION: 7
<223> OTHER INFORMATION: L-IsoAsp
<220> FEATURE:
<221> NAME/KEY: MOD_RES
<222> LOCATION: 8
<223> OTHER INFORMATION: Phosphoserine

<400> SEQUENCE: 49

Asp Ala Glu Phe Arg His Xaa Xaa Gly Tyr Glu Val His His Gln Lys
1               5                   10                  15
```

Leu Val

```
<210> SEQ ID NO 50
<211> LENGTH: 18
<212> TYPE: PRT
<213> ORGANISM: Artificial Sequence
<220> FEATURE:
<223> OTHER INFORMATION: Mouse isoD7-Amyloid beta(1-18)
<220> FEATURE:
<221> NAME/KEY: MOD_RES
<222> LOCATION: 7
<223> OTHER INFORMATION: L-IsoAsp

<400> SEQUENCE: 50
```

Asp Ala Glu Phe Gly His Xaa Ser Gly Phe Glu Val Arg His Gln Lys
1               5                   10                  15

Leu Val

```
<210> SEQ ID NO 51
<211> LENGTH: 30
<212> TYPE: PRT
<213> ORGANISM: Artificial Sequence
<220> FEATURE:
<223> OTHER INFORMATION: isoD7-Amyloid beta(1-30)
<220> FEATURE:
<221> NAME/KEY: MOD_RES
<222> LOCATION: 7
<223> OTHER INFORMATION: L-IsoAsp

<400> SEQUENCE: 51
```

Asp Ala Glu Phe Arg His Xaa Ser Gly Tyr Glu Val His His Gln Lys
1               5                   10                  15

Leu Val Phe Phe Ala Glu Asp Val Gly Ser Asn Lys Gly Ala
            20                  25                  30

```
<210> SEQ ID NO 52
<211> LENGTH: 30
<212> TYPE: PRT
<213> ORGANISM: Artificial Sequence
<220> FEATURE:
<223> OTHER INFORMATION: Amyloid beta(1-30)

<400> SEQUENCE: 52
```

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala
            20                  25                  30

```
<210> SEQ ID NO 53
<211> LENGTH: 112
<212> TYPE: PRT
<213> ORGANISM: Artificial Sequence
<220> FEATURE:
<223> OTHER INFORMATION: hVL11-IGKV4-1

<400> SEQUENCE: 53
```

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Asn Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Asp Ser Gly Val
    50                  55                  60

```
Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Asn Leu Arg Thr Phe Gly Gln Gly Thr Lys Leu Glu Ile Lys
            100                 105                 110
```

<210> SEQ ID NO 54
<211> LENGTH: 336
<212> TYPE: DNA
<213> ORGANISM: Artificial Sequence
<220> FEATURE:
<223> OTHER INFORMATION: hVL11-IGKV4-1 DNA

<400> SEQUENCE: 54

```
gacatcgtga tgacacagag ccccgattct ctggccgtgt ctctgggaga gagagccacc     60
atcaactgca agagcagcca gagcctgctg aacagccgga accggaagaa ttacctggcc    120
tggtatcagc agaagcccgg ccagcctcct aagctgctga tctactgggc cagcaccaga    180
gatagcggcg tgcccgatag attttctggc tctggcagcg gcaccgactt caccctgaca    240
atttctagcc tgcaagccga ggacgtggcc gtgtactact gcaagcagag ctacaacctg    300
cggacctttg gccagggcac caagctggaa atcaaa                              336
```

<210> SEQ ID NO 55
<211> LENGTH: 112
<212> TYPE: PRT
<213> ORGANISM: Artificial Sequence
<220> FEATURE:
<223> OTHER INFORMATION: hVL11-IGKV3-20*01

<400> SEQUENCE: 55

```
Glu Ile Val Leu Thr Gln Ser Pro Gly Thr Leu Ser Leu Ser Pro Gly
1               5                   10                  15

Glu Arg Ala Thr Leu Ser Cys Lys Ser Ser Gln Ser Leu Leu Asn Ser
                20                  25                  30

Arg Asn Arg Lys Asn Tyr Leu Ala Trp Tyr Gln Gln Lys Pro Gly Gln
            35                  40                  45

Ala Pro Arg Leu Leu Ile Tyr Trp Ala Ser Thr Arg Asp Ser Gly Ile
        50                  55                  60

Pro Asp Arg Phe Ser Gly Ser Gly Ser Gly Thr Asp Tyr Thr Leu Thr
65                  70                  75                  80

Ile Ser Arg Leu Glu Pro Glu Asp Phe Ala Val Tyr Tyr Cys Lys Gln
                85                  90                  95

Ser Tyr Asn Leu Arg Thr Phe Gly Gly Gly Thr Lys Val Glu Ile Lys
            100                 105                 110
```

<210> SEQ ID NO 56
<211> LENGTH: 336
<212> TYPE: DNA
<213> ORGANISM: Artificial Sequence
<220> FEATURE:
<223> OTHER INFORMATION: hVL11-IGKV3-20*01 DNA

<400> SEQUENCE: 56

```
gagatcgtgc tgacacagag ccccggaaca ctgtcactgt ctccaggcga aagagccaca    60
ctgagctgca agagcagcca gagcctgctg aacagccgga accggaagaa ttacctggcc   120
tggtatcagc agaagcccgg acaggctcct cggctgctga tctattgggc cagcacaaga   180
```

```
gacagcggca tccccgatag attttccggc agcggcagcg gaaccgacta caccctgaca    240
atcagcagac tggaacccga ggacttcgcc gtgtactact gcaagcagag ctacaacctg    300
cggacctttg gcggaggcac caaggtggaa atcaaa                              336
```

```
<210> SEQ ID NO 57
<211> LENGTH: 219
<212> TYPE: PRT
<213> ORGANISM: Artificial Sequence
<220> FEATURE:
<223> OTHER INFORMATION: hLC11-IGKV4-1 (kappa)

<400> SEQUENCE: 57
```

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Asn Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Asp Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Lys Gln
                85                  90                  95

Ser Tyr Asn Leu Arg Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

```
<210> SEQ ID NO 58
<211> LENGTH: 657
<212> TYPE: DNA
<213> ORGANISM: Artificial Sequence
<220> FEATURE:
<223> OTHER INFORMATION: hLC11-IGKV4-1 (kappa) DNA

<400> SEQUENCE: 58
```

```
gacatcgtga tgacacagag ccccgattct ctggccgtgt ctctgggaga gagagccacc     60
atcaactgca agagcagcca gagcctgctg aacagccgga accggaagaa ttacctggcc    120
tggtatcagc agaagcccgg ccagcctcct aagctgctga tctactgggc cagcaccaga    180
gatagcggcg tgcccgatag attttctggc tctggcagcg gcaccgactt caccctgaca    240
atttctagcc tgcaagccga ggacgtggcc gtgtactact gcaagcagag ctacaacctg    300
cggacctttg gccagggcac caagctggaa atcaaaagga ccgtggccgc accctctgtg    360
```

```
ttcatcttcc cccccagcga cgagcagctg aagagcggca ctgcatctgt cgtgtgtctg    420
ctgaacaact tctacccaag ggaggcgaaa gtgcagtgga aggtagacaa cgccttgcaa    480
tccggcaact cccaggagag cgtgaccgag caggacagca agactcaac ctacagcctg     540 agcagtactt tgaccctgtc taaggccgat tacgagaagc acaaggtgta cgcctgcgag    600
gtaacccacc agggactgag ctctcccgtg accaagagct caacagggg cgagtgc       657
```

<210> SEQ ID NO 59
<211> LENGTH: 219
<212> TYPE: PRT
<213> ORGANISM: Artificial Sequence
<220> FEATURE:
<223> OTHER INFORMATION: hLC11-IGKV3-20*01 (kappa)

<400> SEQUENCE: 59

```
Glu Ile Val Leu Thr Gln Ser Pro Gly Thr Leu Ser Leu Ser Pro Gly
1               5                   10                  15

Glu Arg Ala Thr Leu Ser Cys Lys Ser Ser Gln Ser Leu Leu Asn Ser
            20                  25                  30

Arg Asn Arg Lys Asn Tyr Leu Ala Trp Tyr Gln Gln Lys Pro Gly Gln
        35                  40                  45

Ala Pro Arg Leu Leu Ile Tyr Trp Ala Ser Thr Arg Asp Ser Gly Ile
    50                  55                  60

Pro Asp Arg Phe Ser Gly Ser Gly Ser Gly Thr Asp Tyr Thr Leu Thr
65                  70                  75                  80

Ile Ser Arg Leu Glu Pro Glu Asp Phe Ala Val Tyr Tyr Cys Lys Gln
                85                  90                  95

Ser Tyr Asn Leu Arg Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 60
<211> LENGTH: 657
<212> TYPE: DNA
<213> ORGANISM: Artificial Sequence
<220> FEATURE:
<223> OTHER INFORMATION: hLC11-IGKV3-20*01 (kappa) DNA

<400> SEQUENCE: 60

```
gagatcgtgc tgacacagag ccccggaaca ctgtcactgt ctccaggcga aagagccaca    60
ctgagctgca agagcagcca gagcctgctg aacagccgga accggaagaa ttacctggcc   120
tggtatcagc agaagcccgg acaggctcct cggctgctga tctattgggc cagcacaaga   180
```

```
gacagcggca tccccgatag attttccggc agcggcagcg aaccgactac accctgaca     240 atcagcagac tggaacccga ggacttcgcc gtgtactact gcaagcagag ctacaacctg     300
cggacctttg gcggaggcac caaggtggaa atcaaaagga ccgtggccgc accctctgtg     360
ttcatcttcc cccccagcga cgagcagctg aagagcggca ctgcatctgt cgtgtgtctg     420
ctgaacaact tctacccaag ggaggcgaaa gtgcagtgga aggtagacaa cgccttgcaa     480
tccggcaact cccaggagag cgtgaccgag caggacagca agactcaac ctacagcctg     540 agcagtactt tgaccctgtc taaggccgat tacgagaagc acaaggtgta cgcctgcgag     600
gtaacccacc agggactgag ctctcccgtg accaagagct caacagggg cgagtgc       657
```

```
<210> SEQ ID NO 61
<211> LENGTH: 120
<212> TYPE: PRT
<213> ORGANISM: Artificial Sequence
<220> FEATURE:
<223> OTHER INFORMATION: hVH11-IGHV4-4

<400> SEQUENCE: 61

Gln Val Gln Leu Gln Glu Ser Gly Pro Gly Leu Val Lys Pro Ser Gly
1               5                   10                  15

Thr Leu Ser Leu Thr Cys Ala Val Ser Gly Phe Ser Leu Thr Ser Tyr
            20                  25                  30

Gly Val His Trp Val Arg Gln Pro Pro Gly Lys Gly Leu Glu Trp Leu
        35                  40                  45

Gly Ala Leu Trp Ala Ser Gly Asn Thr Asp Tyr Ser Ser Thr Leu Met
    50                  55                  60

Ser Arg Val Thr Ile Ser Val Asp Lys Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Asp Arg Gly Ile Leu Thr Gly Gly Tyr Phe Asp Val Trp Gly Lys
            100                 105                 110

Gly Thr Thr Val Thr Val Ser Ser
        115                 120
```

```
<210> SEQ ID NO 62
<211> LENGTH: 360
<212> TYPE: DNA
<213> ORGANISM: Artificial Sequence
<220> FEATURE:
<223> OTHER INFORMATION: hVH11-IGHV4-4 DNA

<400> SEQUENCE: 62
caggttcagc tgcaagaatc tggccctggc ctggtcaagc ctagcggaac actgtctctg     60
acctgtgccg tgtccggctt tagcctgaca agctatgggg tgcactgggt ccgacagcct    120
ccaggcaaag gactgaatg gctgggagca ctgtgggcct ctggcaacac agattacagc    180
agcaccctga tgagcagagt gaccatcagc gtggacaaga gcaagaacca gttcagcctg    240
cggctgagca gcgtgacagc tgctgataca gccgtgtact actgcgccag agacagaggc    300
attctgaccg gcggctactt cgatgtgtgg ggcaagggaa ccaccgtgac cgttagttct    360
```

```
<210> SEQ ID NO 63
<211> LENGTH: 120
<212> TYPE: PRT
<213> ORGANISM: Artificial Sequence
<220> FEATURE:
<223> OTHER INFORMATION: hVH11-IGHV4-59
```

-continued

<400> SEQUENCE: 63

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Leu
        35                  40                  45

Gly Ala Leu Trp Ala Ser Gly Asn Thr Asp Tyr Ser Ser Thr Leu Met
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Arg Gly Ile Leu Thr Gly Gly Tyr Phe Asp Leu Trp Gly Arg
            100                 105                 110

Gly Thr Leu Val Thr Val Ser Ser
        115                 120

<210> SEQ ID NO 64
<211> LENGTH: 360
<212> TYPE: DNA
<213> ORGANISM: Artificial Sequence
<220> FEATURE:
<223> OTHER INFORMATION: hVH11-IGHV4-59 DNA

<400> SEQUENCE: 64
caggttcagc tgcaagaatc tggccctggc ctggtcaagc ctagcgagac actgagcctg      60
acctgtaccg tgtccggctt tagcctgaca agctacgggg tgcactggat cagacagcct     120
ccaggcaaag gcctggaatg gctgggagca ctttgggcct ctggcaacac cgattacagc     180
agcaccctga tgagcagagt gaccatcagc gtggacacca gcaagaacca gttcagcctg     240
aagctgagca gcgtgacagc cgccgataca gccgtgtact actgcgccag agacagaggc     300
attctgaccg gcggctactt cgatctgtgg ggcagaggaa cactggtcac cgtcagttct     360

<210> SEQ ID NO 65
<211> LENGTH: 450
<212> TYPE: PRT
<213> ORGANISM: Artificial Sequence
<220> FEATURE:
<223> OTHER INFORMATION: hHC11-IGHV4-4 (IgG1)

<400> SEQUENCE: 65

Gln Val Gln Leu Gln Glu Ser Gly Pro Gly Leu Val Lys Pro Ser Gly
1               5                   10                  15

Thr Leu Ser Leu Thr Cys Ala Val Ser Gly Phe Ser Leu Thr Ser Tyr
            20                  25                  30

Gly Val His Trp Val Arg Gln Pro Pro Gly Lys Gly Leu Glu Trp Leu
        35                  40                  45

Gly Ala Leu Trp Ala Ser Gly Asn Thr Asp Tyr Ser Ser Thr Leu Met
    50                  55                  60

Ser Arg Val Thr Ile Ser Val Asp Lys Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Asp Arg Gly Ile Leu Thr Gly Gly Tyr Phe Asp Val Trp Gly Lys
            100                 105                 110

Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 66
<211> LENGTH: 1350
<212> TYPE: DNA
<213> ORGANISM: Artificial Sequence
<220> FEATURE:
<223> OTHER INFORMATION: hHC11-IGHV4-4 (IgG1) DNA

<400> SEQUENCE: 66
caggttcagc tgcaagaatc tggccctggc ctggtcaagc ctagcggaac actgtctctg        60

```
acctgtgccg tgtccggctt tagcctgaca agctatgggg tgcactgggt ccgacagcct    120
ccaggcaaag gactggaatg gctgggagca ctgtgggcct ctggcaacac agattacagc    180
agcaccctga tgagcagagt gaccatcagc gtggacaaga gcaagaacca gttcagcctg    240
cggctgagca gcgtgacagc tgctgataca gccgtgtact actgcgccag agacagaggc    300
attctgaccg gcggctactt cgatgtgtgg ggcaagggaa ccaccgtgac cgttagttct    360
gccagcacta agggcccgag cgtgttcccc ctcgccccta gcagtaagag caccagcggt    420
ggcacggcgg cacttggctg cttggttaag gactacttcc cagagcccgt gaccgtgtcc    480
tggaactctg ggcacttac  cagtggcgtg cacaccttcc ccgctgtact gcagagcagc    540
ggcttgtaca gcttgtcttc cgtcgtaacg gtgcccagca gcagcttggg aacccagacc    600
tacatctgca acgtaaacca caagccatcc aacaccaagg tagacaaaaa ggtcgaaccc    660
aagtcctgcg acaagaccca cacctgtcca ccctgtcctg cacccgagct cctgggaggt    720
cccagcgttt tcctgttccc tccaaagcca aaggatacccc tgatgatcag caggaccccc    780
gaggtgacct gcgtggtggt ggacgtgagc cacgaagacc ctgaggtcaa gttcaactgg    840
tacgttgatg gggtggaggt acacaatgcc aagaccaaac ctcgagagga gcaatacaac    900
agcacctacc gagttgtgag cgtgcttacc gtgctgcacc aggactggct gaacggcaag    960
gagtacaagt gcaaggtgag caacaaggct ctgccggctc ccatcgagaa gaccatcagc    1020
aaggccaagg gccagcccag ggagccacag gtttacacgt tgcccccctc aagggacgag    1080
ttgaccaaga accaggtttc cctcacgtgc cttgtgaagg gcttctaccc cagcgacatc    1140
gccgtggaat gggagagcaa cgggcagccc gagaacaact acaagacgac ccccctgtt     1200 ctggacagcg acggctcttt cttcctgtat tcaaagctca ccgtggacaa aagcaggtgg    1260 cagcaggggta atgtgttctc ctgcagcgtg atgcacgagg ccctgcataa ccactacacc    1320
caaaagagct tgagcctctc ccccggtaag                                     1350
```

<210> SEQ ID NO 67
<211> LENGTH: 450
<212> TYPE: PRT
<213> ORGANISM: Artificial Sequence
<220> FEATURE:
<223> OTHER INFORMATION: hHC11-IGHV4-59 (IgG1)

<400> SEQUENCE: 67

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Leu
        35                  40                  45

Gly Ala Leu Trp Ala Ser Gly Asn Thr Asp Tyr Ser Ser Thr Leu Met
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Arg Gly Ile Leu Thr Gly Gly Tyr Phe Asp Leu Trp Gly Arg
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
```

```
                   130                 135                 140
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 68
<211> LENGTH: 1350
<212> TYPE: DNA
<213> ORGANISM: Artificial Sequence
<220> FEATURE:
<223> OTHER INFORMATION: hHC11-IGHV4-59 (IgG1) DNA

<400> SEQUENCE: 68
caggttcagc tgcaagaatc tggccctggc ctggtcaagc ctagcgagac actgagcctg      60
acctgtaccg tgtccggctt tagcctgaca agctacgggg tgcactggat cagacagcct     120
ccaggcaaag gcctggaatg gctgggagca ctttgggcct ctggcaacac cgattacagc     180
agcacccctg tgagcagagt gaccatcagc gtggacacca gcaagaacca gttcagcctg     240
```

-continued

```
aagctgagca gcgtgacagc cgccgataca gccgtgtact actgcgccag agacagaggc    300
attctgaccg gcggctactt cgatctgtgg ggcagaggaa cactggtcac cgtcagttct    360
gccagcacta agggcccgag cgtgttcccc ctcgcccta gcagtaagag caccagcggt    420 ggcacgcgg cacttggctg cttggttaag gactacttcc cagagccgt gaccgtgtcc     480 tggaactctg gggcacttac cagtggcgtg cacaccttcc ccgctgtact gcagagcagc    540
ggcttgtaca gcttgtcttc cgtcgtaacg gtgcccagca gcagcttggg aacccagacc    600
tacatctgca acgtaaacca caagccatcc aacaccaagg tagacaaaaa ggtcgaaccc    660
aagtcctgcg acaagaccca cacctgtcca ccctgtcctg cacccgagct cctgggaggt    720
cccagcgttt tcctgttccc tccaaagcca aaggatccc tgatgatcag caggaccccc     780
gaggtgacct gcgtggtggt ggacgtgagc cacgaagacc ctgaggtcaa gttcaactgg    840
tacgttgatg gggtggaggt acacaatgcc aagaccaaac ctcgagagga gcaatacaac    900
agcacctacc gagttgtgag cgtgcttacc gtgctgcacc aggactggct gaacggcaag    960
gagtacaagt gcaaggtgag caacaaggct ctgccggctc ccatcgagaa gaccatcagc   1020
aaggccaagg gccagcccag ggagccacag gtttacacgt tgcccccctc aagggacgag   1080
ttgaccaaga accaggtttc cctcacgtgc cttgtgaagg gcttctaccc cagcgacatc   1140
gccgtggaat gggagagcaa cgggcagccc gagaacaact acaagacgac ccccccctgtt  1200 ctggacagcg acggctcttt cttcctgtat tcaaagctca ccgtggacaa aagcaggtgg   1260
cagcagggta atgtgttctc ctgcagcgtg atgcacgagg ccctgcataa ccactacacc   1320
caaaagagct tgagcctctc ccccggtaag                                    1350
```

ANTI-ISOASP7 AMYLOID β (Aβ) ANTIBODIES AND USES THEREOF

STATEMENT REGARDING SEQUENCE LISTING

The Sequence Listing associated with this application is provided in text format in lieu of a paper copy, and is hereby incorporated by reference into the specification. The name of the text file containing the Sequence Listing is 360079_401USPC_SEQUENCE_LISTING.txt. The text file is 57.1 KB, was created on Jul. 15, 2020, and is being submitted electronically via EFS-Web.

TECHNICAL FIELD

The present invention can be included in the field of medicine. Specifically, the present invention provides antibodies and antigen-binding fragments thereof which can bind isoAsp7 amyloid β (A(β) and a pharmaceutical composition comprising the antibodies or antigen-binding fragments thereof. The antibodies, antigen-binding fragments thereof and the pharmaceutical composition can be used to treat and/or prevent neurodegenerative diseases. Further, the present invention provides hybridoma cell lines, the use of the antibodies or antigen-binding fragments thereof for the diagnosis and/or prognosis of a neurodegenerative disease and a method for detecting isoAsp7 Aβ in an isolated sample.

BACKGROUND ART

Alzheimer's disease (AD) is a progressive incurable neuronal damage of the brain, occurring in mid or late life. One of the first symptoms is short-term memory loss, followed by behavioral issues and disorientation up to loss of body functions. AD always leads to death; usually people die 7 to 10 years after diagnosis.

Two histological alterations can be seen post mortem in AD patients: senile plaques and neurofibrillary tangles, consisting of hyperphosphorylated Tau protein. The former are extracellular deposits, basically composed of fibrillary amyloid beta (Aβ). Aβ peptides arise through endoproteolytic cleavage of APP. Because of their presence within the transmembrane region of APP, Aβ peptides are high in hydrophobic side chains, resulting in poor solubility. After release of Aβ peptides, they have a strong tendency to aggregate. In AD patients, there is an imbalance between generation and degradation of Aβ peptides, they aggregate and deposit, leading to neuronal cell death. The main Aβ variants observed in human brain are Aβ40 and Aβ42, but also N-terminal truncated variants and other posttranslational modified forms are observed in plaques.

There are two different types of AD: the very rare hereditary form (familial AD-FAD) and the sporadic form, of which about 95 percent of patients are affected. FAD is marked by AD symptoms that appear at an unusually early age. Beside presenilin 1 (PSI) and presenilin 2 (PS2), APP belongs to the three known genes that can cause FAD. Mutations in these genes lead to increased Aβ production and virtually guarantee the development of AD. However, it remains unresolved how Aβ exerts its toxic effects. As a genetic disorder, FAD is clearly the consequence of the malfunctioning of the mutated genes, whereas the cause of late-onset spontaneous AD is still not completely understood.

Not only are the reasons for the development of spontaneous AD unknown, scientists all over the world are trying to find AD biomarkers in order to identify AD patients in a possibly early stage. AD can be divided into a pre-symptomatic phase in which subjects are cognitively normal, a prodromal phase known as mild cognitive impairment (MCI) and a third phase when patients show dementia with impairments or even loss of function in daily activities (Petersen (2004) J Intern Med 256:183-94; Savva et al. (2009) N Engl J Med 360:2302-2309). To date, the only highly predictive biomarkers for AD are the genetic mutations that are pathogenic for FAD. They can be detected years before disease onset and identify those individuals who will go on to develop AD later in life. The Alzheimer's disease Neuroimaging Initiative (ADNI) generated a model for the temporal ordering of AD biomarkers which suggests that Aβ amyloid biomarkers become abnormal first, followed by changes in neurodegenerative biomarkers (CSF tau, FDG-PET, MRI) and the onset of clinical symptoms. That means, Aβ peptide arises to pathological concentrations in brain even before patients show first neurological symptoms in the MCI phase. Furthermore, it could be shown that not only mutations, but also posttranslational modifications of the Aβ peptide can accelerate their aggregation behavior, possibly resulting in a severe course of disease.

One posttranslational modification observed in the Aβ peptide is the formation of isoaspartate (isoAsp). The generation of isoAsp from aspartyl residues is a spontaneous posttranslational modification of peptides and proteins. This reaction is considered to determine the half-life of proteins (Robinson and Rudd (1974) Curr Top Cell Regul. 8(0):247-95; Robinson and Robinson (2001) PNAS 98(3):944-949). Besides that, isoAsp-formation introduces an additional methylene group into the backbone of the protein or peptide (Aswad et al. (2000) J Pharm Biomed Anal. 21(6):1129-36; Geiger and Clarke (1987) J Biol Chem 262:785-794), consequently altering its structure. This post-translational modification may also change the properties of proteins like solubility, conformation and function. IsoAsp forms most easily at sequences in which the side chain of the C-flanking amino acid is relatively small and hydrophilic, and is less likely to form when bulky or hydrophobic residues are in this position. The most favorable C-flanking amino acids are glycine, serine, and histidine (Shimizu et al. (2005) Biol Pharm Bull. 28(9):1590-6).

After deposition of insoluble Aβ in senile plaques, the formation of isoAsp7 is likely to occur as time goes by, since Aβ has a serine residue in position 8. The presence of isoAsp7 Aβ in brains of AD patients was first described in 1993 (Roher et al. (1993) Proc. Natl. Acad. Sci. USA 90:10836-10840). By using polyclonal anti-isoAsp7 Aβ antibodies, it could be shown that isoAsp7 Aβ is present in extracellular deposits in AD brain as well as amyloid-bearing vessels and serves as an indicator of plaque age (Fonseca et al. (1999) Exp Neurol. 157(2):277-88; Shimizu et al. (2000) Arch Biochem Biophys. 381(2):225-34). Aβ is able to activate the classical complement pathway (CCP) by direct binding of C1q, resulting in the recruitment of reactive glial cells to the site of fibrillary Aβ protein plaque. Velazquez and colleagues found that isomerization of Asp7 resulted in complete elimination of CCP activation. This could prevent plaque recognition by the complement system.

Since an isoAsp7 modification does not influence aggregation of Aβ peptides (Fukuda et al. (1999) Bioorg Med Chem Lett. 9(7):953-6; Shimizu et al. (2002) J Neurosci Res. 70(3):451-61), it is not likely that this modification accelerates deposition and plaque formation. However, Wakutani et al. described in the year 2004 a new case of FAD, called Japanese-Tottori FAD. In some members of this family, a missense mutation within APP (D678N) replaces the aspartate 7 of Aβ with asparagine (Wakutani et al. (2004) J Neurol Neurosurg Psychiatry. 75(7):1039-42). Asparagine residues undergo isomerization about 10 times quicker than aspartate (Stephenson and Clarke (1989) J Biol Chem 264: 6164-6170). Manifestation of AD symptoms in this pedigree may be not due to Asn7-Aβ, but the enhanced formation of isoAsp7 Aβ.

Although AD has been known for over 100 years, there are still only symptomatic treatments available on the market. Active immunization approaches with Aβ and fragments thereof as well as passive immunization with anti-Aβ antibodies was effective in different animal models. Vaccination of humans with Aβ inhibited the development of Aβ plaques and reduced the Aβ burden in AD patients. However, the clinical studies needed to be stopped due to some patients developing severe meningoencephalitis (Orgogozo et al. (2003) Neurology 61:46-54) or a humoral and cellular response against Aβ resulting in a strong immune response against the endogenous Aβ peptide (Holmes et al. (2008) Lancet 372:216-223).

Consequently, passive immunization was considered safer and more controllable than active immunization. Several antibodies targeting the Aβ peptide have been used in clinical trials of passive immunization therapy in AD patients. However, most antibodies are directed against linear epitopes in the native non modified peptide. Treatment studies showed a positive effect, but have side effects such as amyloid-related imaging abnormalities (ARIA), seizures and death (Moreth et al. (2013) Immun Ageing. 10(1):18).

Thus, there is a need for antibodies for the effective treatment and/or prevention of Aβ plaque-associated diseases such as Alzheimer's disease. The present application provides antibodies that were found to be more effective in a relevant animal model and are thus expected to be more effective at treating and/or preventing Aβ plaque-associated diseases such as Alzheimer's disease.

FIGURES

FIG. 1: Investigation of antibody specificity by Dot Blot analysis. 2 μl of Aβ peptides were spotted in descending concentrations on a nitrocellulose membrane and blocked for 1 h in blocking solution (5% (w/v) milk powder in TBS-T (TBS+0.05% Tween 20 (v/v)). Antibodies K11 (A), K119 (B) and 6E10 (C) were diluted to 1 μg/ml in blocking solution and incubated with the membrane for 1 h, followed by 3×5 minutes washing steps with TBS-T. Anti-mouse antibody conjugated to alkaline phosphatase (AP) was added and incubated for 1 h, followed by 3×5 minutes washing steps and subsequent colorimetric detection of AP activity by addition of substrates BCIP (5-bromo-4-chloro-3-indolyl-phosphate) and NBT (nitro blue tetrazolium). 1—isod7-Aβ(1-17); 2—isoD7-Aβ(5-9)rep; 3—Aβ(1-18); 4—isoD7-Aβ(1-12). Of note, antibody 6E10 does not recognize isoAsp-modified Aβ.

Figure 2:
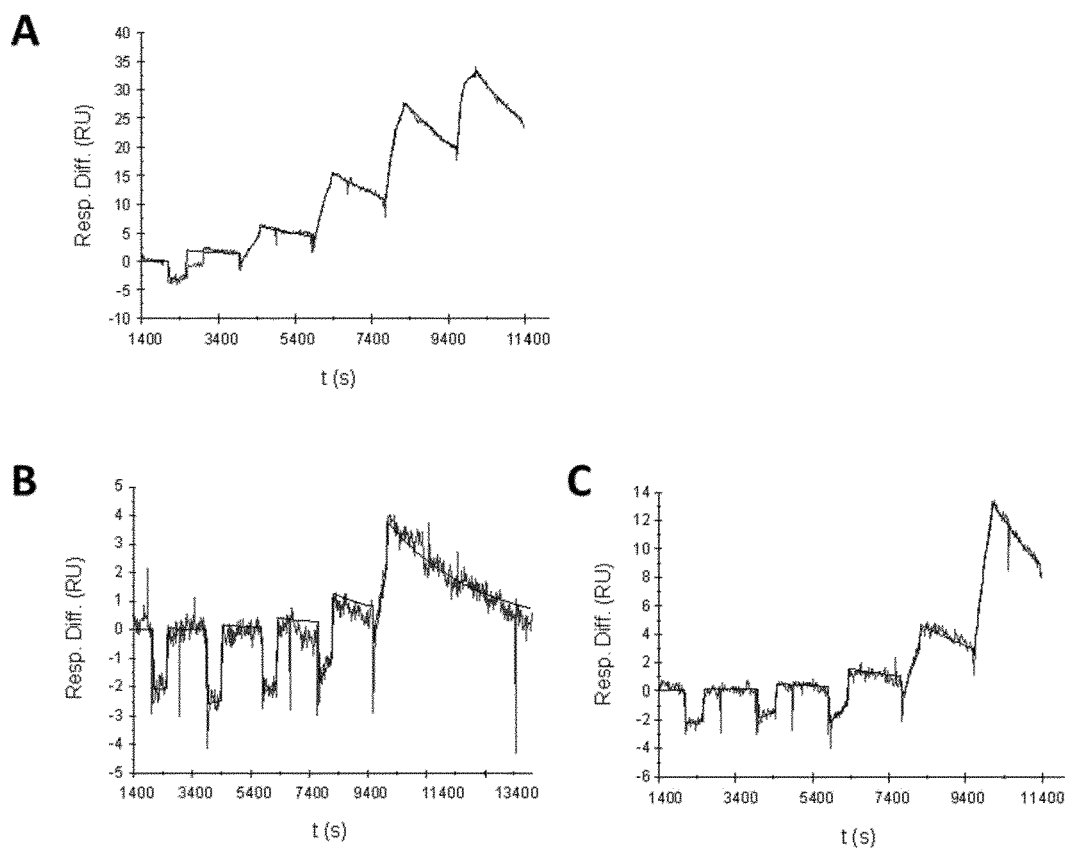

FIG. 2: Determination of binding constants of immobilized K11 with different Aβ-peptides by SPR analysis. 1,500-2,000 RU of antibody K11 were immobilized on a CM5 chip by binding to goat anti mouse IgG. Monomeric Aβ peptides were injected in varying concentrations. $K_D$ values were calculated by using single-cycle kinetic analysis of BIAevaluation software. A—isoD7-Aβ(1-18) was applied at 1 nM, 3 nM, 9 nM, 27 nM, 81 nM and 243 nM. B—isod7-Aβ(1-17) was applied at 1 nM, 3 nM, 9 nM, 27 nM, 81 nM and 243 nM. C—Aβ(1-18) was applied at 10 mM, 30 nM, 90 nM, 270 nM, 810 nM and 2430 nM.

Figure 3:
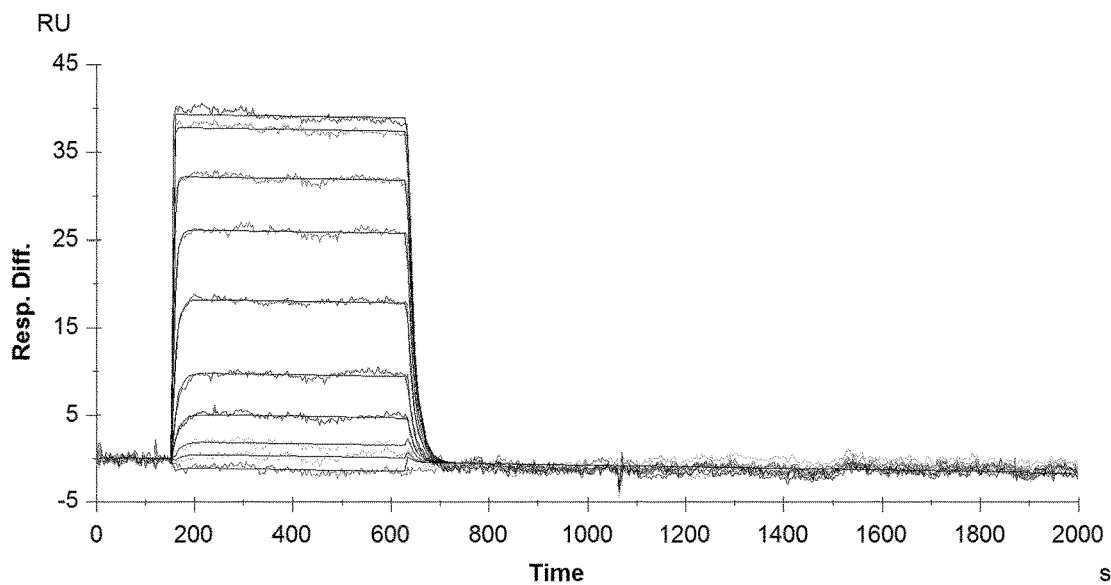

FIG. 3: $K_D$ value determination of immobilized K119 with isoD7-Aβ(1-18) by SPR analysis. About 2,000 RU of antibody K119 were immobilized on a CM5 chip by binding to goat anti mouse IgG. Monomeric isoD7-Aβ(1-18) peptides were injected in varying concentrations (1 nM, 2 nM, 5 nM, 10 nM, 20 nM, 50 nM, 100 nM, 200 nM, 500 nM, 1 μM). $K_D$ value was calculated by using multi-cycle kinetic analysis of BIAevaluation software.

Figure 4:
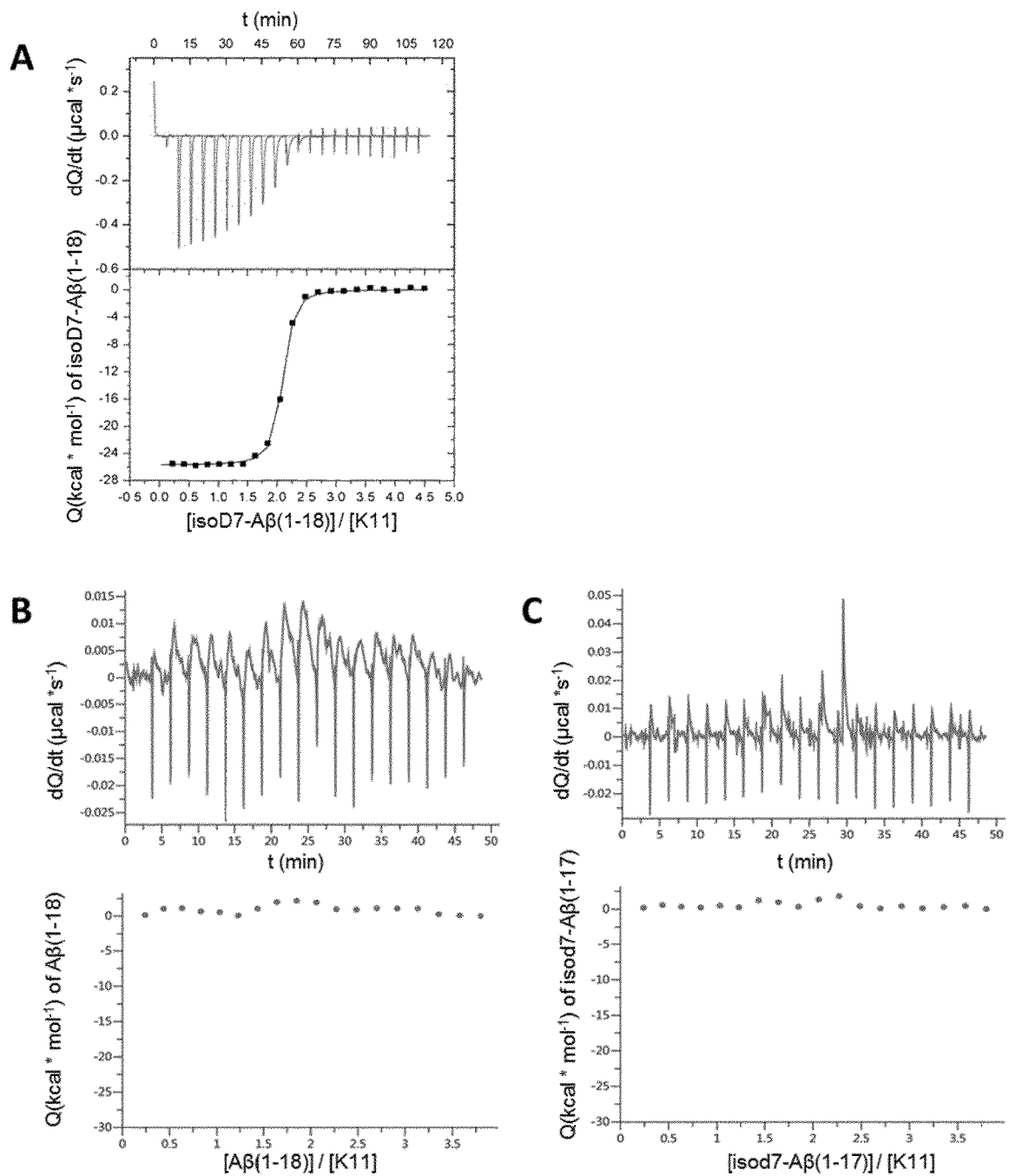

FIG. 4: Thermodynamic characterization of K11 with different Aβ-peptides. Determination of the thermodynamic parameter of K11 with different antigens at 25° C. K11 was dialyzed against an Aβ-peptides dissolved in ITC buffer (25 mM $KH_2PO_4$; 25 mM $Na_2HPO_4$; 150 mM NaCl; 1 mM EDTA, pH 7.4). Peptides were added every 5 minutes to antibody solution in the following concentrations:

A—50.8 μM isoD7-Aβ(1-18) was titrated to 2.5 μM K11
B—56.7 μM Aβ(1-18) was titrated to 11.9 μM K11
C—238 μM isod7-Aβ(1-17) was titrated to 11.9 μM K11

The top graphs show raw data of heat pulses resulting from titration of antigen in the calorimetric cell with antibody K11. The bottom graphs show the integrated heat pulses, normalized per mol of injectant as a function of molar ratio.

Figure 5:
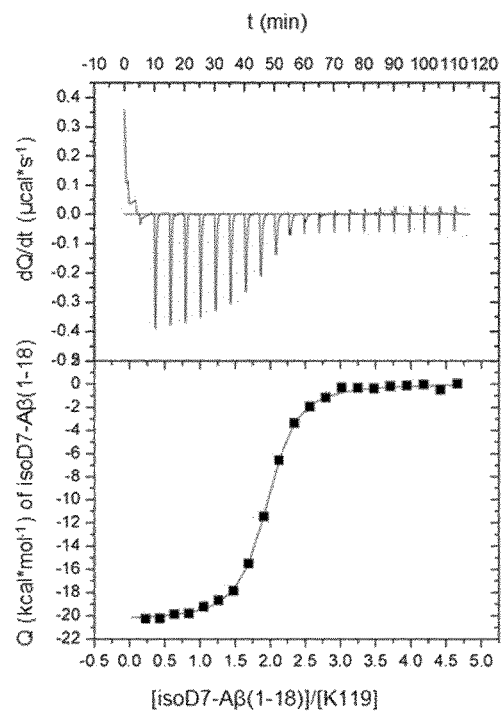

FIG. 5: Thermodynamic characterization of K119 binding to isoD7-Aβ(1-18) by using isothermal titration calorimetry. K119 was dialyzed against and the peptide isoD7-Aβ(1-18) dissolved in ITC buffer (25 mM KH2PO4; 25 mM Na2HPO4; 150 mM NaCl; 1 mM EDTA, pH 7.4). 44.9 μM peptide solution was added every 5 minutes to 2.2 μM antibody solution. The top graph shows raw data of heat pulses resulting from titration of antigen in the calorimetric cell with antibody K119. The bottom graph shows the integrated heat pulses, normalized per mol of injectant as a function of molar ratio.

Figure 6:
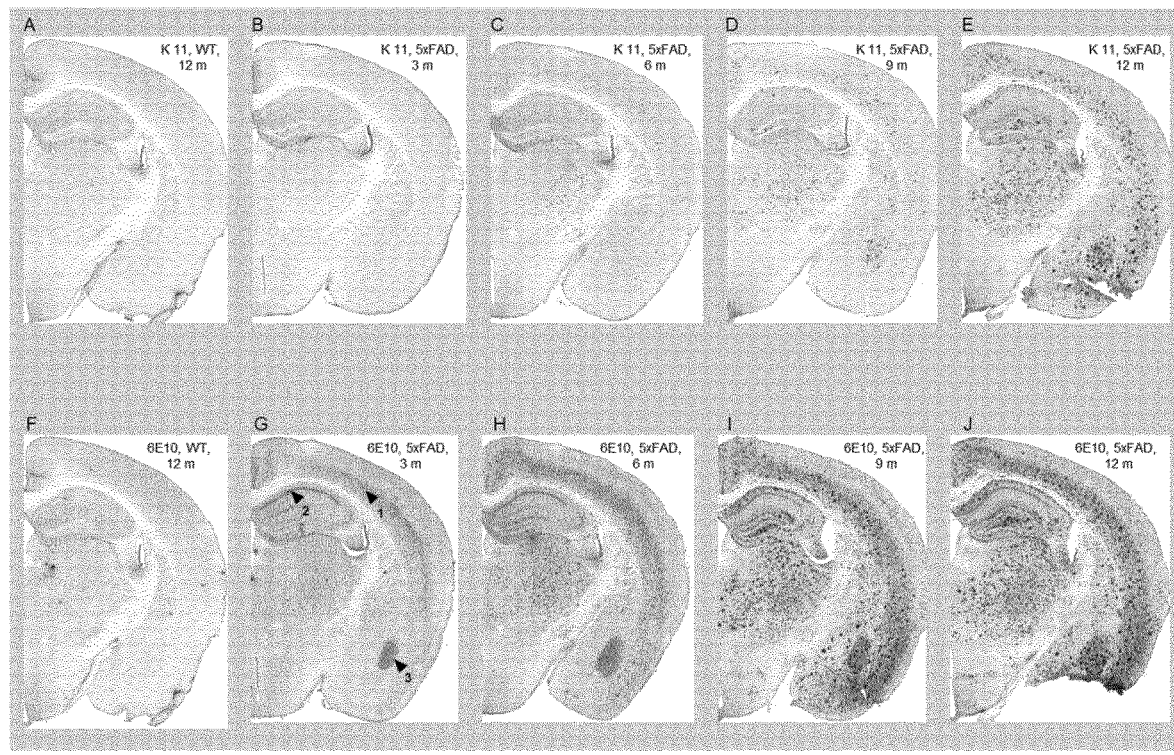

FIG. 6: Immunohistochemical analysis of AD aggregates in brain samples from 5×FAD and wildtype mice by using K11. Paraformaldehyde treated and cryoconserved brain slices from 5×FAD mice (B-E and G-J) with different ages and 12 month old wildtype mice (A and F) have been treated with anti isoAsp7-Aβ antibody K11 (A-E) and commercially available antibody 6E10, followed by application of biotinylated anti mouse IgG. Immunostaining was performed by addition of ExtrAvidin-Peroxidase (Sigma-Aldrich) and the chromogenic substrate 3,3'-Diaminobenzidin (DAB). A) Wildtype mouse, 12 month old, stained with K11. B) 5×FAD mouse, 3 month old, stained with K11. C) 5×FAD mouse, 6 month old, stained with K11. D) 5×FAD mouse, 9 month old, stained with K11. E) 5×FAD mouse, 12 month old, stained with K11. F) Wildtype mouse, 12 month old, stained with 6E10. G) 5×FAD mouse, 3 month old, stained with 6E10. H) 5×FAD mouse, 6 month old, stained with 6E10. I) 5×FAD mouse, 9 month old, stained with 6E10. J) 5×FAD mouse, 12 month old, stained with 6E10.

Figure 7:
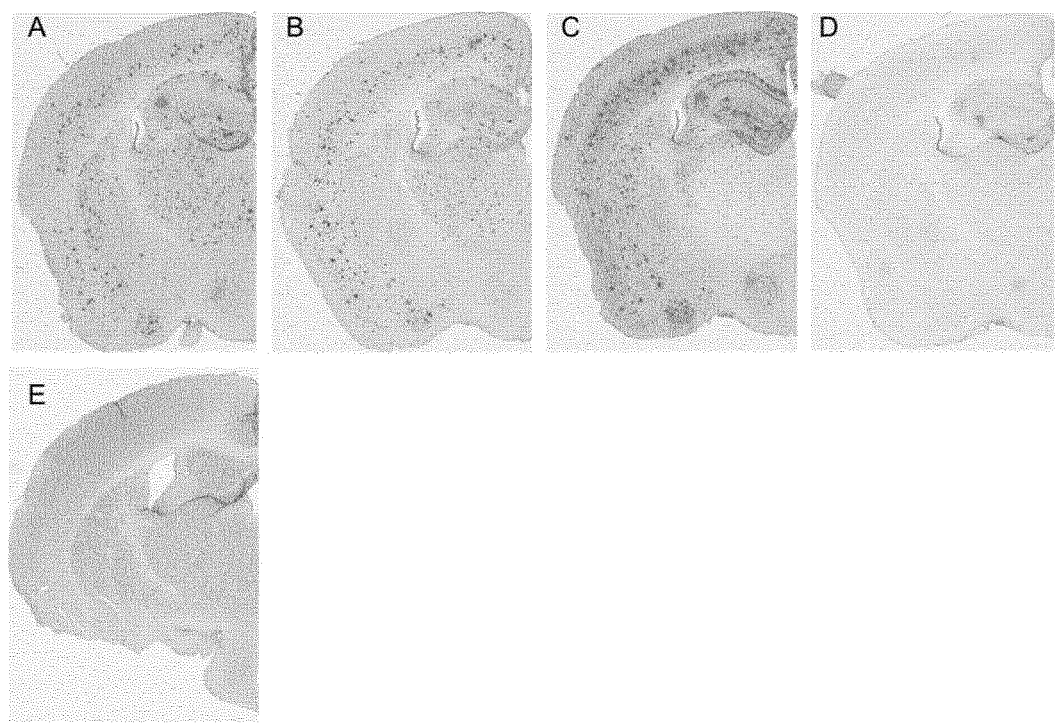

FIG. 7: Comparative staining of Aβ aggregates in brain samples from 12 month old 5×FAD mice with different antibodies. Formaldehyde treated and cryoconserved brain slices from 12 month old 5×FAD mice have been treated with anti isoAsp7-Aβ antibody K119 (A), K11 (B), 6E10 (C) and without primary antibody (D), followed by application of biotinylated anti mouse IgG. FIG. 7 (E) shows staining of a wildtype mouse brain slice with K119. Immunostaining was performed by addition of ExtrAvidin-Peroxidase (Sigma-Aldrich) and the chromogenic substrate 3,3'-Diaminobenzidin (DAB).

Figure 8:
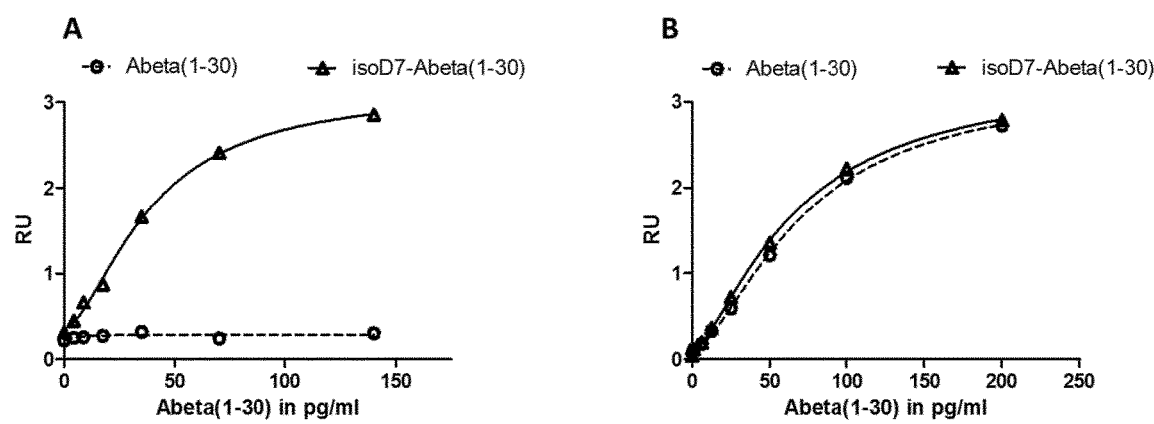

FIG. 8: Sandwich ELISA for quantification of isoAsp7-Aβ and total Aβ concentrations in biological samples. Capture antibodies K11 (A) and 3D6 (B) were diluted to 2 μg/ml and immobilized on microtiter plates overnight at 4° C. Blocking occurred for 2 hours at room temperature. isoD7-Aβ(1-30) (SEQ ID NO: 51) and Aβ(1-30) (SEQ ID NO: 52) were serially diluted and added to the wells in duplicate. After an incubation period of 2 hours at 4° C., plates were washed six times with TBS-T. HRP-conjugated anti Aβ antibody clone 4G8 was added in a final concentration of 1 μg/ml and incubated for 1 hour at 4° C. After washing with TBS-T, a color reaction with TMB was performed and stopped by the addition of 1.2 N $H_2SO_4$. The standard curve was calculated from measured absorption at 450/540 nm by a 4-Parameter-Logistic-Fit: $y=(A2+(A1-A2)/(1+(x/x_0)^p)$.

Figure 9:
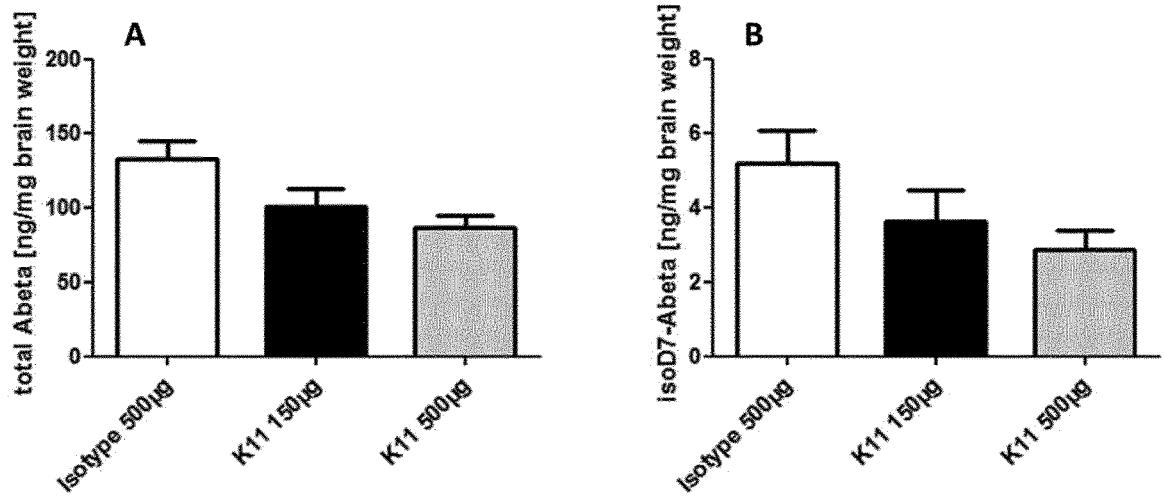

FIG. 9: Quantification of total Aβ (A) and isoAsp7-Aβ (B) peptides in 5 M GdmCl fractions from 5×FAD mice brain treated with K11 and isotype control. Three month old 5×FAD mice were treated intraperitoneally once a week with 500 μg, 150 μg K11 or 500 μg isotype control. After 12 weeks of treatment, mice were sacrificed and the left hemisphere was homogenized in T-Per buffer, followed by centrifugation. The resulting pellet was resuspended in 5 M GdmCl (150 mg/ml), again centrifuged and the supernatant applied to a total Aβ (A) or isoAsp7-Aβ (B) specific ELISA.

Figure 10:
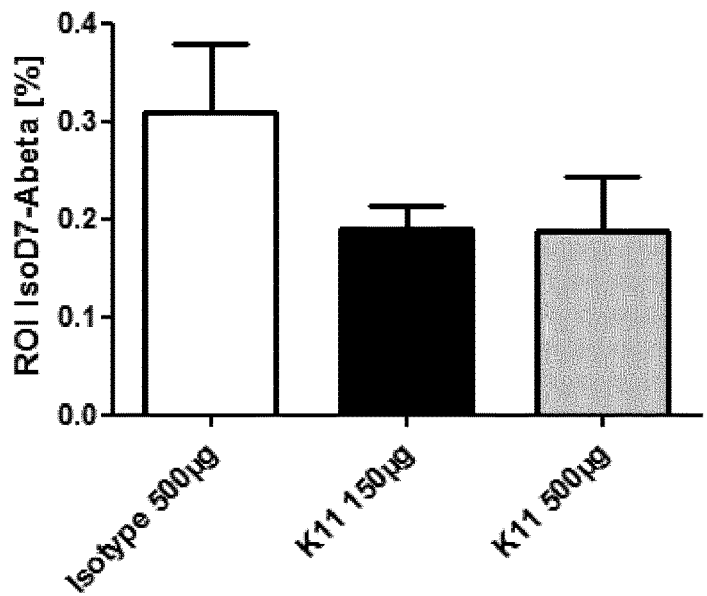

FIG. 10: Immunohistochemical analysis of isoAsp7-Aβ containing aggregates in hippocampal brain slices from 5×FAD mice treated with K11 and isotype control. Three month old 5×FAD mice were treated intraperitoneally once a week with 500 μg, 150 μg K11 or 500 μg isotype control. After 12 weeks of treatment, mice were sacrificed and the right hemisphere was treated with formaldehyde, cryoconserved and used for immunohistochemical staining. 30 μm slices were made from hippocampal sections and incubated with 2 μg/ml K11, followed by application of biotinylated anti mouse IgG. Immunostaining was performed by addition of ExtrAvidin-Peroxidase (Sigma-Aldrich) and the chromogenic substrate 3,3'-Diaminobenzidin (DAB). Regions of interest (ROI) in hippocampal brain slices were selected by staining with 2 μg/ml 6E10 (for general Aβ) and 2 μg/ml isoAsp7-Aβ specific antibody K11 (for isoAsp7-Aβ). All pictures were recorded by using the microscope Biorevo BZ-9000 (Keyence) with transmitted light modus and an exposure time of ½₀₀ s. Percentage area of isoAsp7-Aβ (ROI isoD7 in %) was quantified based on total area of ROI by using the program BZ II Analyzer.

Figure 11:
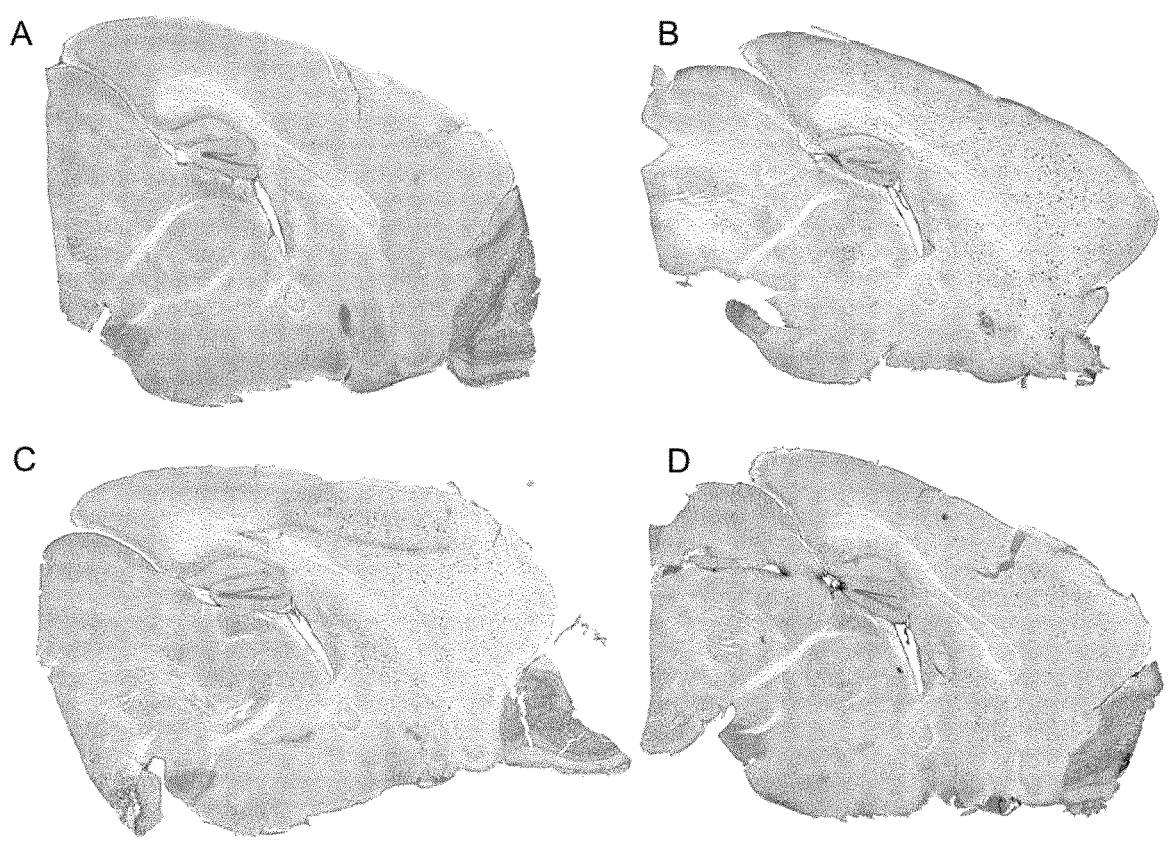

FIG. 11: Immunohistochemical staining of isoAsp7-Aβ containing aggregates in brain samples from 5×FAD mice treated with K11 and isotype control. Three month old 5×FAD mice were treated intraperitoneally once a week with 500 μg, 150 μg K11 or 500 μg isotype control. After 12 weeks of treatment, mice were sacrificed. The right hemisphere was used to prepare paraformaldehyde treated and cryoconserved brain slices. Brain slices have been treated with K11, followed by application of biotinylated anti mouse IgG. Immunostaining was performed by addition of ExtrAvidin-Peroxidase (Sigma-Aldrich) and the chromogenic substrate 3,3'-Diaminobenzidin (DAB). A) 3 month old 5×FAD mouse (baseline control), B) 6 month old 5×FAD mouse, treated with 500 μg Isotype control antibody, C) 6 month old 5×FAD mouse, treated with 150 μg K11, D) 6 month old 5×FAD mouse, treated with 500 μg K11.

Figure 12:
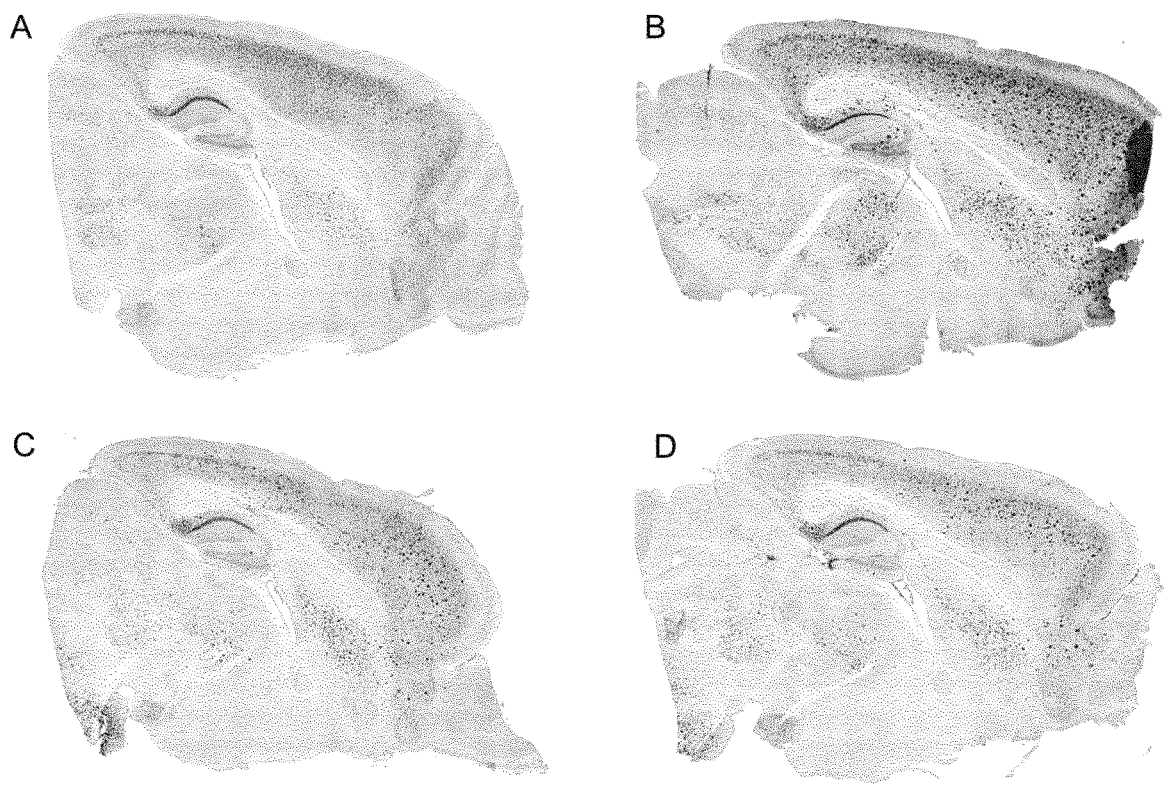

FIG. 12: Immunochemical staining of Aβ aggregates (antibody 6E10) in brain samples from 5×FAD mice treated with K11 and isotype control. Three month old 5×FAD mice were treated intraperitoneally once a week with 500 μg, 150 μg K11 or 500 μg isotype control. After 12 weeks of treatment, mice were sacrificed. The right hemisphere was used to prepare paraformaldehyde treated and cryoconserved brain slices. Brain slices have been treated with commercially available antibody 6E10, followed by application of biotinylated anti mouse IgG. Immunostaining was performed by addition of ExtrAvidin-Peroxidase (Sigma-Aldrich) and the chromogenic substrate 3,3'-Diaminobenzidin (DAB). A) 3 month old 5×FAD mouse (baseline control), B) 6 month old 5×FAD mouse, treated with 500 μg Isotype control antibody, C) 6 month old 5×FAD mouse, treated with 150 μg K11, D) 6 month old 5×FAD mouse, treated with 500 μg K11.

Figure 13:
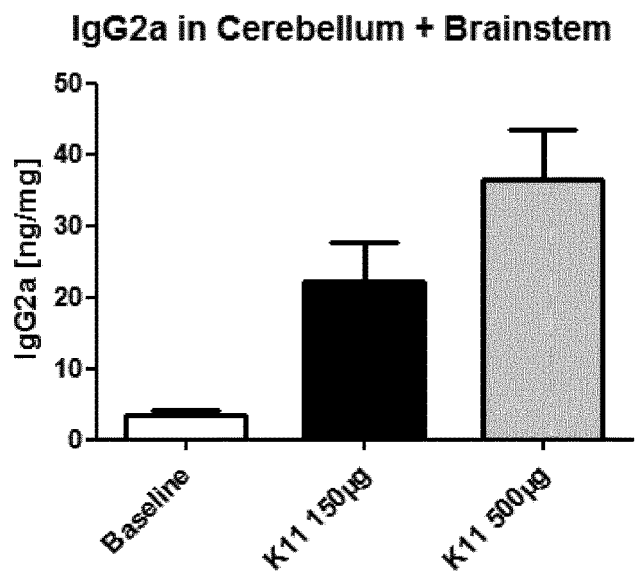

FIG. 13: Quantification of IgG2a in cerebellum and brainstem from 5×FAD mice treated with KM Three month old 5×FAD mice were treated intraperitoneally once a week with 500 μg or 150 μg K11. After 12 weeks of treatment, mice were sacrificed; cerebellum and brainstem were homogenized in ELISA Blocker+Tween, followed by centrifugation. The resulting supernatant was applied to a mouse IgG2a specific ELISA. Baseline represents 3 month old 5×FAD mice without treatment.

Figure 14:
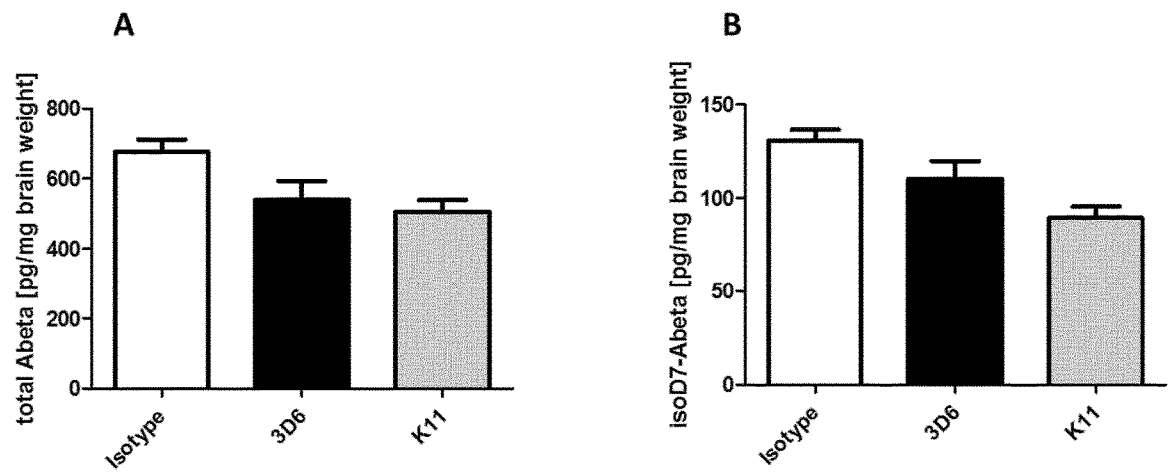

FIG. 14: Quantification of total Aβ (A) and isoD7-Aβ (B) peptides in T-Per fractions from 5×FAD mice brain treated with anti-Aβ antibodies K11, 3D6 and isotype control. Three month old 5×FAD mice were treated intraperitoneally once a week with 300 μg K11, 3D6 or isotype control. After 6 months of treatment, mice were sacrificed and the left hemisphere was homogenized in T-Per buffer (Thermofisher) to 50 mg brain weight/ml T-Per buffer. The resulting T-Per fractions were applied to a total Aβ as well as isoAsp7-Aβ specific ELISA. Sample size consisted of at least 10 animals per group (some groups contained one or two more animals). Statistical analysis was performed using Bonferroni's Multiple Comparison Test. * means p≤0.05.  means p≤0.01. * means p≤0.001.

Figure 15:
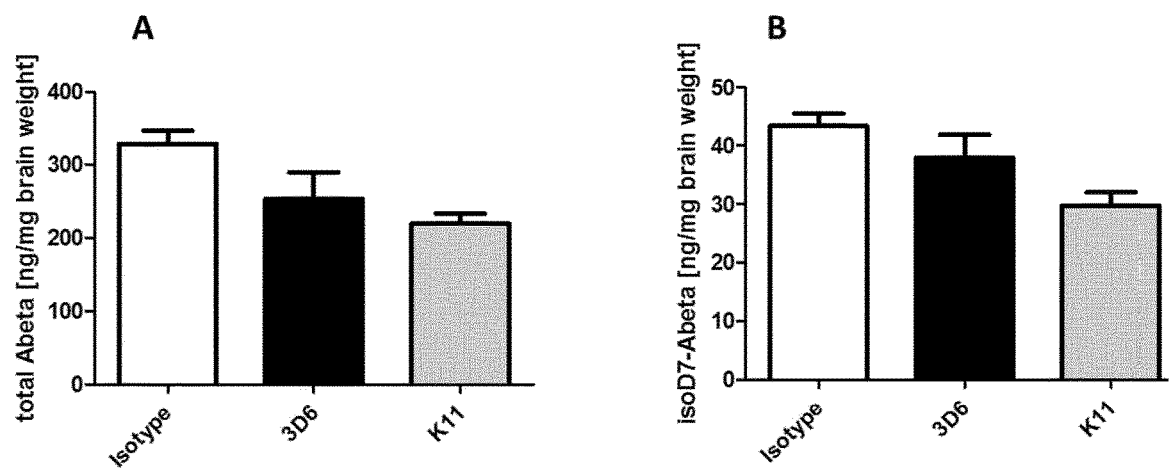

FIG. 15: Quantification of total Aβ (A) and isoD7-Aβ (B) peptides in 5 M GdmCl fractions from 5×FAD mice brain treated with anti-Aβ antibodies K11, 3D6 and isotype control. Three month old 5×FAD mice were treated intraperitoneally once a week with 300 μg K11, 3D6 and isotype control. After 6 months of treatment, mice were sacrificed and the left hemisphere was homogenized in T-Per buffer (50 mg/ml), followed by centrifugation. The resulting pellet was resuspended in 5 M GdmCl (150 mg/ml), again centrifuged and the supernatant was subjected to a total Aβ as well as isoAsp7-Aβ specific ELISA. Sample size consisted of at least 10 animals per group (some groups contained one or two more animals). Statistical analysis was performed using Bonferroni's Multiple Comparison Test. * means p≤0.05.  means p≤0.01. * means p≤0.001.

Figure 16:
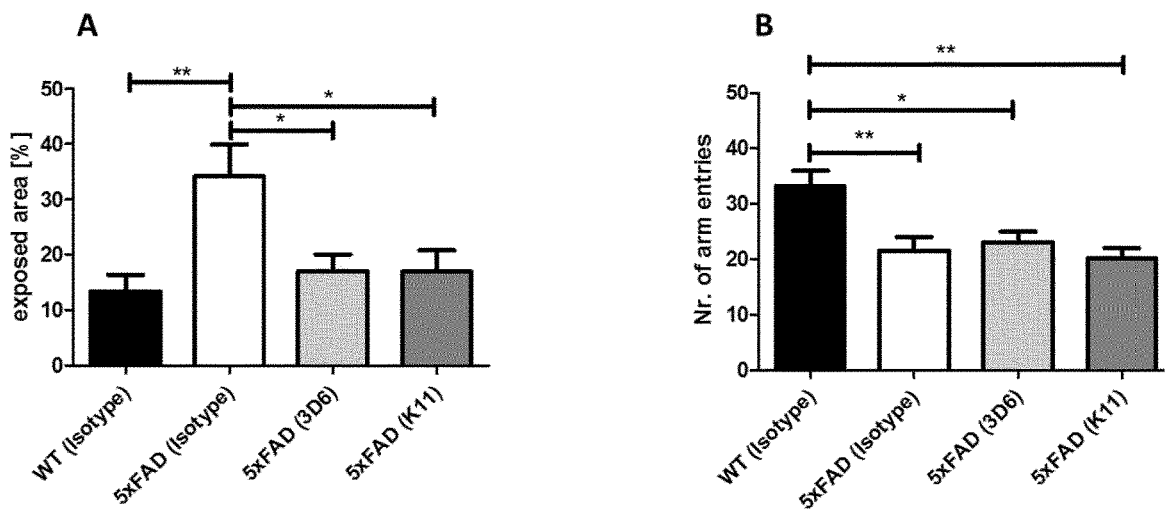

FIG. 16: Elevated Plus Maze (EPM) test of 5×FAD animals treated weekly for 38 weeks with 300 μg K11, 3D6 and isotype control. Antibody-treated 5×FAD groups were compared with wildtype animals treated with 300 μg isotype control. Test animals were placed with their head to the end of a defined closed arm of an elevated, plus-shaped (+) apparatus with two open and two enclosed arms. During the next 10 minutes, every movement of the test animals was recorded.

A—The time the animals spent in the open arms was summed up in order to calculate % in exposed area.

B—Arm entries are defined as presence of the complete animal (except tail) in the open arm.

Sample size consisted of at least 9 animals per group (some groups contained one or two more animals). Statistical analysis was performed using Bonferroni's Multiple Comparison Test. * means p≤0.05.  means p≤0.01. * means p≤0.001.

Figure 17:
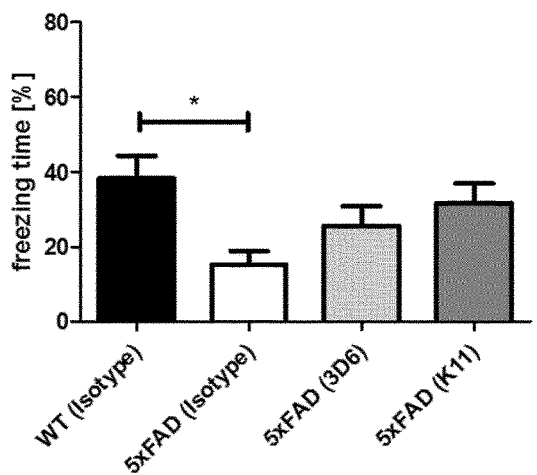

FIG. 17: Fear conditioning test of 5xFAD animals treated weekly for 38 weeks with 300 μg K11, 3D6 and isotype control. Antibody-treated 5xFAD groups were compared with wildtype animals treated with 300 μg isotype control. Test animals were placed in an automated FearConditioning System and submitted to the following procedure: pause (180 s), sound (28 s), electric stimulus (0.7 mA for 2 s). After 24 h, test animals were again placed in the FearConditioning System, left there for 210 s and then removed. One hour later, animals were placed back in the container in order to expose them to a 180 s pause, followed by 180 s of sound (neutral stimulus). A state of fear was expressed by the mice by freezing in place. Freezing time during the 180 s pause was counted and subtracted from the freezing times during the 180 s sound in order to obtain % freezing time. Sample size consisted of at least 8 animals per group (some groups contained one or two more animals). Statistical analysis was performed using Bonferroni's Multiple Comparison Test. * means p≤0.05.  means p≤0.01. * means p≤0.001.

Figure 18:
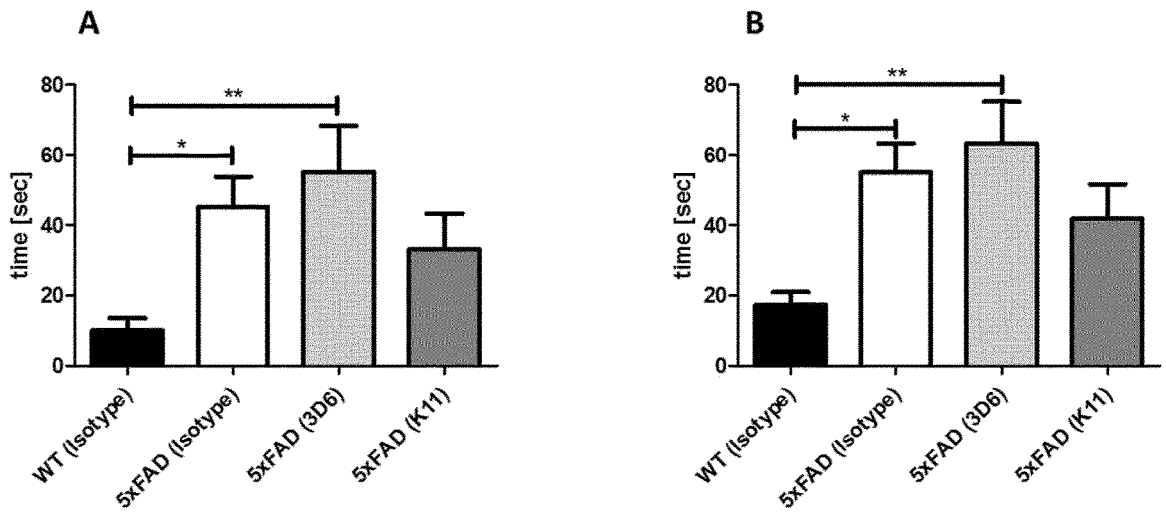

FIG. 18: Pole test of 5xFAD animals treated weekly for 38 weeks with 300 μg K11, 3D6 and isotype control. Antibody-treated 5xFAD groups are compared with wildtype animals treated with 300 μg isotype control. Animals were placed with their head directed to the top on a 50 cm high pole (diameter 1.5 cm). The animals were unhanded and time was counted until (A) animals turned around (defined as every single paw is directed to the ground) and (B) animals reached the ground with every paw. Sample size consisted of at least 10 animals per group (some groups contained one or two more animals). Statistical analysis was performed using Bonferroni's Multiple Comparison Test. * means p≤0.05.  means p≤0.01. * means p≤0.001.

Figure 19:
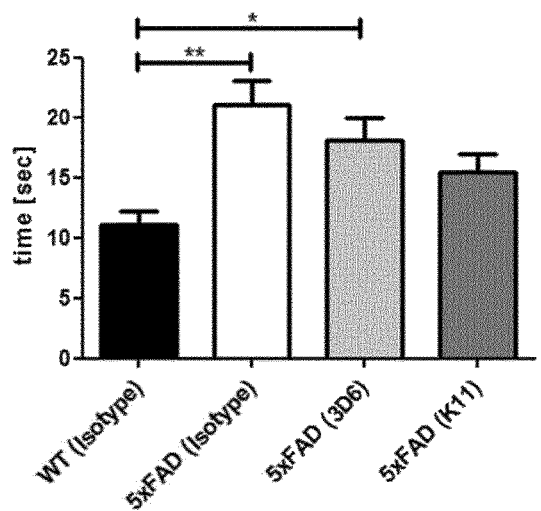

FIG. 19: Morris water maze test of 5xFAD animals treated weekly for 38 weeks with 300 μg K11, 3D6 and isotype control. Antibody-treated 5xFAD groups are compared with wildtype animals treated with 300 μg isotype control. Test animals were placed in a circular pool and are required to find an invisible platform that allows them to escape the water. The circular pool is divided into 4 equal quadrants. Test animals were placed into the first quadrant and time was counted until they reached the platform. After at least a 5 min pause, test animals were placed into the second quadrant and exposed to the same procedure. The animals were allowed to pause again, followed by putting them in quadrant 3, followed by another pause and putting them again in quadrant 2. At the end, time until the test animals reach the platform was counted and summed up for every mouse in 4 trials per day. The graph shows the average trial time until animals reached the platform on day 4. Sample size consisted of at least 10 animals per group (some groups contained one or two more animals). Statistical analysis was performed using Bonferroni's Multiple Comparison Test. * means p≤0.05.  means p≤0.01. * means p≤0.001.

Figure 20:
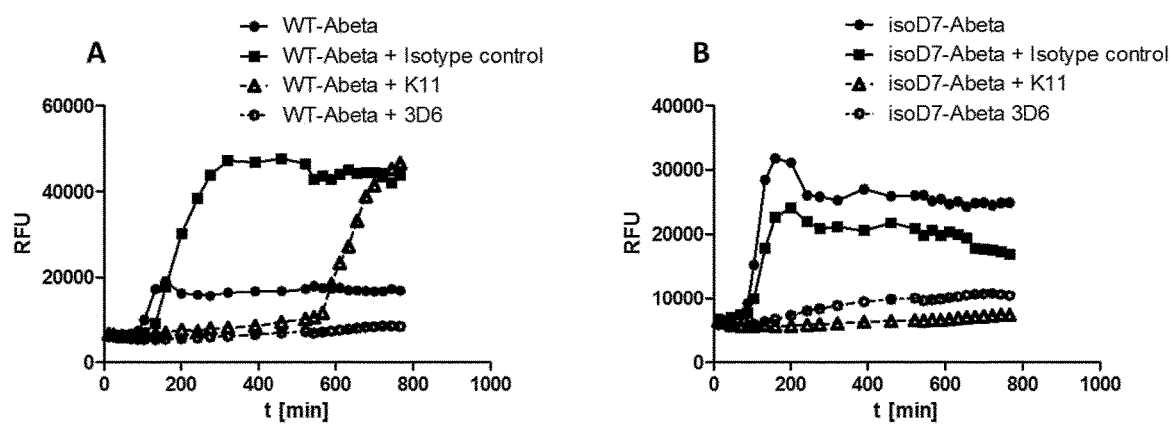

FIG. 20: Aggregation of wildtype Aβ (A) and isoD7-Aβ (B) peptides after addition of K11, 3D6 and isotype control. Synthetic wildtype Aβ(1-40) and isoD7-Aβ(1-40) peptides have been monomerized by dissolving them in hexafluoroisopropanol (HFIP). HFIP was allowed to evaporate overnight, peptides were dissolved in 1 volume 0.1 M NaOH, followed by the addition of 18 volumes PBS and 1 volume 0.1 M HCl. Antibodies K11, 3D6 and isotype control were added subsequently to a final concentration of 5 μM, leading to a concentration of 10 μM Aβ peptides. After addition of 200 μM ThT (Thioflavin T), fluorescence at 435/485 nm (ex/em) was tracked in a microplate reader (FluoStar Optima, BMG Labtech) at 37° C. under shaking conditions (600 rpm).

SUMMARY OF THE INVENTION

Targeting of isoAsp7 Aβ in AD patients is a new promising approach, because antibodies will solely bind modified and aged Aβ peptides. Consequently, freshly synthesized circulating Aβ in the periphery will be largely unaffected, thereby preventing loss of active antibodies via Aβ binding in e.g. blood or CSF. This possibly allows a reduction of antibody dosage. Furthermore, the epitope density of isoAsp7-modified species in Aβ deposits is low in comparison to native Aβ variants. This leads to a better antibody distribution within the brain tissue and a lower reactivity with amyloid deposits in the walls of blood vessels in the central nervous system (cerebral amyloid angiopathy, CAA), thereby preventing ARIA.

Here, we show that treatment of transgenic mice with Alzheimer-pathology with an isoAsp7-Aβ specific antibody results in attenuation of disease pathology. Surprisingly, we observed that application of a highly isoAsp-specific antibody does not only reduce isoAsp7-Aβ in these mice but also shows an unexpected reduction of amyloid plaques and non-isoAsp7-modified Aβ (see FIGS. 9 and 12 below). This result was obtained by using an antibody derived from clone 6E10, which, as shown here for the first time, specifically detects unmodified (i.e. containing Asp instead of isoAsp in position 7) Aβ (FIG. 1). Therefore, both antibodies were used to prove this differential activity of isoAsp-Aβ specific antibodies, enabling an application of isoAsp-Aβ for treatment of Aβ plaque-associated diseases such as Alzheimer's disease.

Moreover, we also show that the isoAsp7-modified Aβ is, compared to total Aβ, an underrepresented species, making up only 4% in mice (FIG. 9). Despite this low concentration, we observed an unexpected reduction of amyloid plaques after treatment (FIGS. 9, 11, 12, and 15). This novel finding might help to circumvent previous limitations of Aβ immunotherapy.

Surprisingly, an antibody of the present invention was able to remove more fibrillary Aβ than 3D6 (an antibody that binds to residues 1-5 of an Aβ42 peptide without an L-isoAsp 7 modification) as shown in FIG. 15A. This appears to be associated with a greater amount of monomeric, oligomeric and fibrillary isoAsp-modified Aβ removal (FIGS. 14B and 15B). Further, an antibody of the present invention improves the treatment of 5xFAD mice in comparison to 3D6 (see FIGS. 17-19).

The present invention thus provides an antibody or antigen-binding fragment thereof which specifically binds to isoAsp7 amyloid β (A(β), wherein the $K_D$ of the interaction between the antibody and SEQ ID NO: 44 is at least 10 times less than the $K_D$ of the interaction between the antibody and SEQ ID NO: 8. The present invention also provides a pharmaceutical composition comprising the antibody or antigen-binding fragment thereof of the present invention and a pharmaceutically acceptable carrier or diluent. Also, the present invention encompasses the use of the antibody or antigen-binding fragment thereof of the present invention or the pharmaceutical composition of the present invention as a medicament, specifically for the treatment and/or prevention of a neurodegenerative disease. Further, the present invention provides the use of the antibody or antigen-binding fragment thereof of the present invention for the diagnosis and/or prognosis of a neurodegenerative disease. The present invention also provides hybridoma cell-lines and a method for detecting isoAsp7 Aβ comprising a step wherein an isolated sample is put into contact with the antibody or antigen-binding fragment thereof of the present invention. Finally, the present invention provides a method of determining the percentage of peptides in an amyloid plaque which comprises an L-isoAsp at position 7 of SEQ ID NO: 1.

DETAILED DESCRIPTION OF THE INVENTION

Antibodies

In a first aspect, the present invention provides an antibody or antigen-binding fragment thereof which specifically binds to isoAsp7 amyloid β (Aβ), wherein the $K_D$ of the interaction between the antibody and SEQ ID NO: 44 is at least 10 times less than the $K_D$ of the interaction between the antibody and SEQ ID NO: 8. In a preferred embodiment, the $K_D$ of the interaction between the antibody and SEQ ID NO: 48 is at least 10 times less than the $K_D$ of the interaction between the antibody and SEQ ID NO: 8. Preferably, the $K_D$ is determined by surface plasmon resonance or isothermal titration calorimetry. More preferably, the $K_D$ is determined by surface plasmon resonance at 25° C.

In an alternative aspect, the present invention provides an antibody or antigen-binding fragment thereof which specifically binds to pE3 (contains L-pyroglutamate at position 3) isoAsp7 amyloid β (Aβ) wherein the $K_D$ of the interaction between the antibody and SEQ ID NO: 48 is at least 10 times less than the $K_D$ of the interaction between the antibody and SEQ ID NO: 8.

SEQ ID NO: 44 is isoAsp7 Aβ (1-18) and has the following sequence:

DAEFRHXSGYEVHHQKLV, wherein X is L-isoAsp.

SEQ ID NO: 8 is Aβ (1-18) and has the following sequence:

DAEFRHDSGYEVHHQKLV

SEQ ID NO: 48 is pE3-isoD7-Aβ(3-18) and has the following sequence:

ZFRHXSGYEVHHQKLV, wherein X is L-isoAsp and Z is L-pyroglutamate.

As used herein, the term "antibody" refers to a protein comprising at least one immunoglobulin variable domain sequence. The term antibody includes, for example, full-length and mature antibodies. For example, an antibody can include a heavy (H) chain variable domain sequence (abbreviated herein as VH), and a light (L) chain variable domain sequence (abbreviated herein as VL). In another example, an antibody molecule includes two heavy (H) chain variable domain sequences and two light (L) chain variable domain sequence, thereby forming two antigen binding sites, such as Fab, Fab', F(ab')2, Fc, Fd, Fd', Fv, single chain antibodies (scFv for example), single variable domain antibodies, diabodies (Dab) (bivalent and bispecific), and chimeric (e.g., humanized) antibodies, which may be produced by the modification of whole antibodies or those synthesized de novo using recombinant DNA technologies. These functional antibody fragments retain the ability to selectively bind with their respective antigen or receptor. Antibodies and antibody fragments can be from any class of antibodies including, but not limited to, IgG, IgA, IgM, IgD, and IgE, and from any subclass (e.g., IgG1, IgG2, IgG3, and IgG4) of antibodies. The antibodies of the present invention can be monoclonal or polyclonal. The antibody can also be a human, humanized, CDR-grafted, or in vitro generated antibody. The antibody can have a heavy chain constant region chosen from, e.g., IgG1, IgG2, IgG3, or IgG4. The antibody can also have a light chain chosen from, e.g., kappa or lambda.

Examples of antigen-binding fragments include: (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a diabody (dAb) fragment, which consists of a VH domain; (vi) a camelid or camelized variable domain; (vii) a single chain Fv (scFv), see e.g., Bird et al. (1988) Science 242:423-426; and Huston et al. (1988) Proc. Natl. Acad. Sci. USA 85:5879-5883); (viii) a single domain antibody. These antibody fragments are obtained using conventional techniques known to those with skill in the art, and the fragments are screened for utility in the same manner as are intact antibodies.

The term "antibody" includes intact molecules. Constant regions of the antibodies can be altered, e.g., mutated, to modify the properties of the antibody (e.g., to increase or decrease one or more of: Fc receptor binding, antibody glycosylation, the number of cysteine residues, effector cell function or complement function).

Antibody molecules can also be single domain antibodies. Single domain antibodies can include antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, fish, shark, goat, rabbit, and bovine. According to another aspect of the invention, a single domain antibody is a naturally occurring single domain antibody known as heavy chain antibody devoid of light chains. Such single domain antibodies are disclosed in WO 9404678, for example. For clarity reasons, this variable domain derived from a heavy chain antibody naturally devoid of light chain is known herein as a VHH or nanobody to distinguish it from the conventional VH of four chain immunoglobulins. Such a VHH molecule can be derived from antibodies raised in *Camelidae* species, for example in camel, llama, dromedary, alpaca and guanaco. Other species besides *Camelidae* may produce heavy chain antibodies naturally devoid of light chain; such VHHs are within the scope of the invention.

The VH and VL regions can be subdivided into regions of hypervariability, termed "complementarily determining regions" (CDR), interspersed with regions that are more conserved, termed "framework regions" (FR or FW).

The extent of the framework region and CDRs has been precisely defined by a number of methods (see, Kabat, E. A., et al. (1991) Sequences of Proteins of Immunological Interest, Fifth Edition, U.S. Department of Health and Human Services, NIH Publication No. 91-3242; Chothia, C. et al. (1987) J. Mol. Biol. 196:901-917; and the AbM definition used by Oxford Molecular's AbM antibody modeling software). See, generally, e.g., Protein Sequence and Structure Analysis of Antibody Variable Domains. In: Antibody Engineering Lab Manual (Ed.: Duebel, S. and Kontermann, R., Springer-Verlag, Heidelberg).

The terms "complementarity determining region," and "CDR," as used herein refer to the sequences of amino acids within antibody variable regions which confer antigen specificity and binding affinity. In general, there are three CDRs in each heavy chain variable region (HCDR1, HCDR2, HCDR3) and three CDRs in each light chain variable region (LCDR1, LCDR2, LCDR3).

The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273,927-948 ("Chothia" numbering scheme). As used herein, the CDRs defined according the "Chothia" number scheme are also sometimes referred to as "hypervariable loops".

The terms "monoclonal antibody" as used herein refers to a preparation of antibody molecules of single molecular composition. A monoclonal antibody composition displays a single binding specificity and affinity for a particular epitope. A monoclonal antibody can be made by hybridoma technology or by methods that do not use hybridoma technology (e.g., recombinant methods).

The antibody or antigen-binding fragment thereof can be a polyclonal or a monoclonal antibody. In other embodiments, the antibody can be recombinantly produced, e.g., produced by phage display or by combinatorial methods. Preferably, the antibody or antigen-binding fragment thereof is a monoclonal antibody or antigen-binding fragment thereof.

Phage display and combinatorial methods for generating antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) Bio/Technology 9:1370-1372; Hay et al. (1992) Hum Antibod Hybridomas 3:81-85; Huse et al. (1989) Science 246:1275-1281; Griffths et al. (1993) EMBO J 12:725-734; Hawkins et al. (1992) J Mol Biol 226:889-896; Clackson et al. (1991) Nature 352:624-628; Gram et al. (1992) PNAS 89:3576-3580; Garrad et al. (1991) Bio/Technology 9:1373-1377; Hoogenboom et al. (1991) Nuc Acid Res 19:4133-4137; and Barbas et al. (1991) PNAS 88:7978-7982, the contents of all of which are incorporated by reference herein).

In one embodiment, the antibody is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. Preferably, the non-human antibody is a rodent (mouse or rat antibody). Methods of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 Nature 368:856-859; Green, L. L. et al. 1994 Nature Genet. 7:13-21; Morrison, S. L. et al. 1994 Proc. Natl. Acad. Sci. USA 81:6851-6855; Bruggeman et al. 1993 Year Immunol 7:33-40; Tuaillon et al. 1993 PNAS 90:3720-3724; Bruggeman et al. 1991 Eur J Immunol 21:1323-1326).

An antibody can be one in which the variable region, or a portion thereof, e.g., the CDRs, are generated in a non-human organism, e.g., a rat or mouse. Chimeric, CDR-grafted, and humanized antibodies are within the invention. Antibodies generated in a non-human organism, e.g., a rat or mouse, and then modified, e.g., in the variable framework or constant region, to decrease antigenicity in a human are within the invention.

Chimeric antibodies can be produced by recombinant DNA techniques known in the art (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125,023; Better et al. (1988 Science 240:1041-1043); Liu et al. (1987) PNAS 84:3439-3443; Liu et al., 1987, J. Immunol. 139:3521-3526; Sun et al. (1987) PNAS 84:214-218; Nishimura et al., 1987, Canc. Res. 47:999-1005; Wood et al. (1985) Nature 314:446-449; and Shaw et al., 1988, J. Natl Cancer Inst. 80:1553-1559).

A humanized or CDR-grafted antibody will have at least one or two but generally all three recipient CDRs (of heavy and or light immuoglobulin chains) replaced with a donor CDR. The antibody may be replaced with at least a portion of a non-human CDR or only some of the CDRs may be replaced with non-human CDRs. It is only necessary to replace the number of CDRs required for binding of the humanized antibody to isoAsp7 Aβ. Preferably, the donor will be a rodent antibody, e.g., a rat or mouse antibody, and the recipient will be a human framework or a human consensus framework. Typically, the immunoglobulin providing the CDRs is called the "donor" and the immunoglobulin providing the framework is called the "acceptor". In one embodiment, the donor immunoglobulin is a non-human (e.g., rodent) immunoglobulin. The acceptor framework is a naturally-occurring (e.g., a human) framework or a consensus framework, or a sequence about 85% or higher, preferably 90%, 95%, 99% or higher identical thereto.

As used herein, the term "consensus sequence" refers to the sequence formed from the most frequently occurring amino acids (or nucleotides) in a family of related sequences (see e.g., Winnaker, From Genes to Clones (Verlagsgesellschaft, Weinheim, Germany 1987)). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by methods known in the art (see e.g., Morrison, S. L., 1985, Science 229:1202-1207, by Oi et al., 1986, BioTechniques 4:214, and by Queen et al. U.S. Pat. Nos. 5,585,089, 5,693,761 and 5,693,762, the contents of all of which are hereby incorporated by reference).

Humanized or CDR-grafted antibodies can be produced by CDR-grafting or CDR substitution, wherein one, two, or all CDRs of an immunoglobulin chain can be replaced. See e.g., U.S. Pat. No. 5,225,539; Jones et al. 1986 Nature 321:552-525; Verhoeyan et al. 1988 Science 239:1534; Beidler et al. 1988 J. Immunol. 141:4053-4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference.

Also within the scope of the invention are humanized antibodies in which specific amino acids have been substituted, deleted or added. Criteria for selecting amino acids from the donor are described in U.S. Pat. No. 5,585,089, e.g., columns 12-16 of U.S. Pat. No. 5,585,089, e.g., columns 12-16 of U.S. Pat. No. 5,585,089, the contents of which are hereby incorporated by reference. Other techniques for humanizing antibodies are described in Padlan et al. EP 519596 A1, published on Dec. 23, 1992.

The antibody can be a single chain antibody. A single-chain antibody (scFV) may be engineered (see, for example, Colcher, D. et al. (1999) Ann N Y Acad Sci 880:263-80; and Reiter, Y. (1996) Clin Cancer Res 2:245-52). The single chain antibody can be dimerized or multimerized to generate multivalent antibodies having specificities for different epitopes of the same target protein.

In yet other embodiments, the antibody has a heavy chain constant region chosen from, e.g., the heavy chain constant regions of IgG1, IgG2, IgG3, IgG4, IgM, IgA1,IgA2, IgD, and IgE; particularly, chosen from, e.g., the (e.g., human) heavy chain constant regions of IgG1, IgG2, IgG3, and IgG4. In another embodiment, the antibody has a light chain constant region chosen from, e.g., the (e.g., human) light chain constant regions of kappa or lambda. The constant region can be altered, e.g., mutated, to modify the properties of the antibody (e.g., to increase or decrease one or more of: Fc receptor binding, antibody glycosylation, the number of cysteine residues, effector cell function, and/or complement function). In one embodiment the antibody has effector function and can fix complement. In other embodiments the antibody does not recruit effector cells or fix complement. In another embodiment, the antibody has reduced or no ability to bind an Fc receptor. For example, it is a isotype or subtype, fragment or other mutant, which does not support binding to an Fc receptor, e.g., it has a mutagenized or deleted Fc receptor binding region.

Methods for altering an antibody constant region are known in the art. Antibodies with altered function, e.g. altered affinity for an effector ligand, such as FcR on a cell, or the C1 component of complement can be produced by replacing at least one amino acid residue in the constant portion of the antibody with a different residue (see e.g., EP 388,151 A1, U.S. Pat. Nos. 5,624,821 and 5,648,260, the contents of all of which are hereby incorporated by reference). Similar type of alterations could be described which if applied to the murine, or other species immunoglobulin would reduce or eliminate these functions.

An antibody can be derivatized or linked to another functional molecule (e.g., another peptide or protein). As used herein, a "derivatized" antibody molecule is one that has been modified. Methods of derivatization include but are not limited to the addition of a fluorescent moiety, a radionucleotide, a toxin, an enzyme or an affinity ligand such as biotin. Accordingly, the antibody molecules of the invention are intended to include derivatized and otherwise modified forms of the antibodies described herein, including immunoadhesion molecules. For example, an antibody molecule can be functionally linked (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate association of the antibody or antibody portion with another molecule (such as a streptavidin core region or a polyhistidine tag).

One type of derivatized antibody molecule is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

An antibody molecule may be conjugated to another molecular entity, typically a label or a therapeutic (e.g., a cytotoxic or cytostatic) agent or moiety. Radioactive isotopes can be used in diagnostic or therapeutic applications. Such radioactive isotopes include, but are not limited to iodine (131I or 125I), yttrium (90Y), lutetium (177Lu), actinium (225Ac), praseodymium, astatine (211At), rhenium (186Re), bismuth (212Bi or 213Bi), indium (111In), technetium (99 mTc), phosphorus (32P), rhodium (188Rh), sulfur (35S), carbon (14C), tritium (3H), chromium (51Cr), chlorine (36Cl), cobalt (57Co or 58Co), iron (59Fe), selenium (75Se), or gallium (67Ga). Radioisotopes useful as labels, e.g., for use in diagnostics, include iodine (131I or 125I), indium (111In), technetium (99mTc), phosphorus (32P), carbon (14C), and tritium (3 H), or one or more of the therapeutic isotopes listed above.

The invention provides radiolabeled antibody molecules and methods of labeling the same. In one embodiment, a method of labeling an antibody molecule is disclosed. The method includes contacting an antibody molecule, with a chelating agent, to thereby produce a conjugated antibody. The conjugated antibody is radiolabeled with a radioisotope, e.g., 111Indium, 90Yttrium and 177Lutetium, to thereby produce a labeled antibody molecule.

The antibody molecule can be conjugated to a therapeutic agent. The antibody may be labeled. For example, the antibody may be labeled with a biotin molecule, an enzyme or a fluorophore.

The terms "isoAsp7 amyloid β", "isoAsp7 Aβ", "isoD7 Aβ" and "isoD7 amyloid Aβ" refer to an amyloid β (Aβ) polypeptide wherein the Asp at position 7 has isomerized. Thus, isoAsp7 Aβ refers to an Aβ polypeptide which comprises SEQ ID NO: 44 and an antibody which is specific for isoAsp7 Aβ will preferentially bind an epitope comprising the L-isoAsp present in SEQ ID NO: 44.

The term "$K_D$" refers to the dissociation constant. In a preferred embodiment, the $K_D$ is determined by surface plasmon resonance or isothermal titration calorimetry. Preferably, the $K_D$ is determined by surface plasmon resonance at 25° C.

In a preferred embodiment, the $K_D$ of the interaction between the antibody and SEQ ID NO: 44 is at least 100 times less than the $K_D$ of the interaction between the antibody and SEQ ID NO: 8. More preferably, the $K_D$ of the interaction between the antibody and SEQ ID NO: 44 is at least 150, 200, 250, 300, 350 or 400 times less than the $K_D$ of the interaction between the antibody and SEQ ID NO: 8. Preferably, the $K_D$ is determined by surface plasmon resonance or isothermal titration calorimetry. More preferably, the $K_D$ is determined by surface plasmon resonance at 25° C.

In a preferred embodiment, the $K_D$ of the interaction of the antibody or antigen-binding fragment and SEQ ID NO: 44 at 25° C. is less than 100 nM. Preferably, the $K_D$ is less than 50, 40, 30, 20 or 10 nM. More preferably, the $K_D$ is less than 50 nM. Most preferably, the $K_D$ is less than 10 nM. Preferably, the $K_D$ is determined by surface plasmon resonance or isothermal titration calorimetry. More preferably, the $K_D$ is determined by surface plasmon resonance at 25° C.

In a preferred embodiment, the antibody or antigen-binding fragment thereof comprises a light chain variable region (VL) and a heavy chain variable region (VH), wherein said VL comprises LCDR1, LCDR2 and LCDR3 polypeptides and VH comprises HCDR1, HCDR2 and HCDR3 polypeptides which are selected from the group consisting of:
  (a) LCDR1 is KSSQSLLNSRNRKNYLA (SEQ ID NO: 9), LCDR2 is WASTRDS (SEQ ID NO: 11), LCDR3 is KQSYNLRT (SEQ ID NO: 13), HCDR1 is GFSLTSYGVH (SEQ ID NO: 14), HCDR2 is ALWASGNTDYSSTLMS (SEQ ID NO: 15), and HCDR3 is DRGILTGGYFDV (SEQ ID NO: 17);
  (b) LCDR1 is KSSQSLFNSRTRKNYVA (SEQ ID NO: 27), LCDR2 is WASTRES (SEQ ID NO: 29), LCDR3 is KQSYNLRA (SEQ ID NO: 30), HCDR1 is GFTFTDYYMS (SEQ ID NO: 32), HCDR2 is FIRNKANGYTTEYSASVKG (SEQ ID NO: 34), and HCDR3 is DIPTIMDY (SEQ ID NO: 35);
  (c) LCDR1 is KSSQSLLNX$_1$RX$_2$RKNYLA (SEQ ID NO: 10), LCDR2 is WASTRX$_3$S (SEQ ID NO: 12), LCDR3 is KQSYNLRT (SEQ ID NO: 13), HCDR1 is GFSLTSYGVH (SEQ ID NO: 14), HCDR2 is X$_4$LWASGX$_5$TDYX$_6$SX$_7$LMS (SEQ ID NO: 16), and HCDR3 is DRGIX$_8$TGGYFDV (SEQ ID NO: 18), wherein X$_1$ is S or R, X$_2$ is N or T, X$_3$ is D or E, X$_4$ is A or V, X$_5$ is N or R, X$_6$ is S or N, X$_7$ is T or A, and X$_8$ is L, T or M; and
  (d) LCDR1 is KSSQX$_1$LX$_2$NSRTRKNYX$_3$A (SEQ ID NO: 28), LCDR2 is WASTRES (SEQ ID NO: 29), LCDR3 is X$_4$QSYNLRX$_5$ (SEQ ID NO: 31), HCDR1 is GFTFX$_6$DYYMX$_7$ (SEQ ID NO: 33), HCDR2 is FIRNKANGYTTEYSASVKG (SEQ ID NO: 34), and HCDR3 is DIPTIMDY (SEQ ID NO: 35), wherein X$_1$ is S or N, X$_2$ is F or L, X$_3$ is V or L, X$_4$ is K or M, X$_5$ is A or T, X$_6$ is T or S, and X$_7$ is S or N.

In a preferred embodiment, the antibody or antigen-binding fragment thereof comprises a VL and a VH, wherein the VL and VH are polypeptides selected from the group consisting of: (a) VL of SEQ ID NO: 19 and VH of SEQ ID NO: 20; (b) VL of SEQ ID NO: 36 and VH of SEQ ID NO: 37; (c) VL of SEQ ID NO: 19 and VH of SEQ ID NO: 37; and (d) VL of SEQ ID NO: 36 and VH of SEQ ID NO: 20.

SEQ ID NO: 19 is the VL fragment present in K11 and has the following sequence:

DIVMSQSPTSLAVSAGEKVTMSCKSSQSLLNSRNRKNYLAWYQQKPGQSP

K11IYWASTRDSGVPDRFTGSGSGTDFTLTISSVQAEDLAVYYCKQSYNL

RTFGGGTKLEIK

SEQ ID NO: 20 is the VH fragment present in K11 and has the following sequence:

QVQLKESGPGLVAPSQSLSITCTVSGFSLTSYGVHWVRQPPGKGLEW

LGALWASGNTDYSSALMSRLSISKDNSKSQVFLKMNSLQTDDTAMYY

CARDRGIMTGGYFDVWGAGTTVTVSS

SEQ ID NO: 36 is the VL fragment present in K119 and has the following sequence:

DIVMSQSPSSLAVSAGEKATMSCKSSQSLFNSRTRKNYVAWLQQKPG

QSPK11ISWASTRESGVPDRFTGSGSGTDFALTITNVQAEDLAVYYC

KQSYNLRAFGGGTKLEIT

SEQ ID NO: 37 is the VH fragment present in K119 and has the following sequence:

EVKLVESGGGLVQPGGSLRLSCATSGFTFTDYYMSWVRQPPGKALEW

LGFIRNKANGYTTEYSASVKGRFTISRDNSQSILYLQMNTLRTEDSA

TYYCTRDIPTIMDYWGQGTSVTVSS

In a preferred embodiment, the antibody or antigen-binding fragment thereof comprises a light chain (LC) and a heavy chain (HC), wherein said LC and HC are polypeptides selected from the group consisting of: (a) LC of SEQ ID NO: 21 and HC of SEQ ID NO: 22; (b) LC of SEQ ID NO: 38 and HC of SEQ ID NO: 39;(c) LC of SEQ ID NO: 21 and HC of SEQ ID NO: 39; and (d) LC of SEQ ID NO: 38 and HC of SEQ ID NO: 22.

SEQ ID NO: 21 is the LC present in K11 and has the following sequence:

DIVMSQSPTSLAVSAGEKVTMSCKSSQSLLNSRNRKNYLAWYQQKPG

QSPK11IYWASTRDSGVPDRFTGSGSGTDFTLTISSVQAEDLAVYYC

KQSYNLRTFGGGTKLEIKRADAAPTVSIFPPSSEQLTSGGASVVCFL

NNFYPKDINVKWKIDGSERQNGVLNSWTDQDSKDSTYSMSSTLTLTK

DEYERHNSYTCEATHKTSTSPIVKSFNRNEC

SEQ ID NO: 22 is the HC present in K11 and has the following sequence:

QVQLKESGPGLVAPSQSLSITCTVSGFSLTSYGVHWVRQPPGKGLEW

LGALWASGNTDYSSTLMSRLSISKDNSKSQVFLKMNSLQTDDTAMYY

CARDRGILTGGYFDVWGAGTTVTVSSAKTTPPSVYPLAPGSAAQTNS

MVTLGCLVKGYFPEPVTVTWNSGSLSSGVHTFPAVLQSDLYTLSSSV

TVPSSTWPSETVTCNVAHPASSTKVDKKIVPRDCGCKPCICTVPEVS

SVFIFPPKPKDVLTITLTPKVTCVVVDISKDDPEVQFSWFVDDVEVH

TAQTQPREEQFNSTFRSVSELPIMHQDWLNGKEFKCRVNSAAFPAPI

-continued

EKTISKTKGRPKAPQVYTIPPPKEQMAKDKVSLTCMITDFFPEDITV

EWQWNGQPAENYKNTQPIMDTDGSYFVYSKLNVQKSNWEAGNTFTCS

VLHEGLHNHHTEKSLSHSPGK

SEQ ID NO: 38 is the LC present in K119 and has the following sequence:

DIVMSQSPSSLAVSAGEKATMSCKSSQSLFNSRTRKNYVAWLQQKPG

QSPK11ISWASTRESGVPDRFTGSGSGTDFALTITNVQAEDLAVYYC

KQSYNLRAFGGGTKLEITRADAAPTVSIFPPSSEQLTSGGASVVCFL

NNFYPKDINVKWKIDGSERQNGVLNSWTDQDSKDSTYSMSSTLTLTK

DEYERHNSYTCEATHKTSTSPIVKSFNRNEC

SEQ ID NO: 39 is the HC present in K119 and has the following sequence:

EVKLVESGGGLVQPGGSLRLSCATSGFTFTDYYMSWVRQPPGKALEW

LGFIRNKANGYTTEYSASVKGRFTISRDNSQSILYLQMNTLRTEDSA

TYYCTRDIPTIMDYWGQGTSVTVSSAKTTAPSVYPLAPVCGDTTGSS

VTLGCLVKGYFPEPVTLTWNSGSLSSGVHTFPAVLQSDLYTLSSSVT

VTSSTWPSQSITCNVAHPASSTKVDKKIEPRGPTIKPCPPCKCPAPN

LLGGPSVFIFPPKIKDVLMISLSPIVTCVVVDVSEDDPDVQISWFVN

NVEVHTAQTQTHREDYNSTLRVVSALPIQHQDWMSGKEFKCKVNNKD

LPAPIERTISKPKGSVRAPQVYVLPPPEEEMTKKQVTLTCMVTDFMP

EDIYVEWTNNGKTELNYKNTEPVLDSDGSYFMYSKLRVEKKNWVERN

SYSCSVVHEGLHNHHTTKSFSRTPGK

In a preferred embodiment, the antibody or antigen-binding fragment thereof comprises two LCs and two HCs, wherein each LC and each HC are polypeptides selected from the group consisting of: (a) LC of SEQ ID NO: 21 and HC of SEQ ID NO: 22; (b) LC of SEQ ID NO: 38 and HC of SEQ ID NO: 39; (c) LC of SEQ ID NO: 21 and HC of SEQ ID NO: 39; and (d) LC of SEQ ID NO: 38 and HC of SEQ ID NO: 22.

In a preferred embodiment, the antibody or antigen-binding fragment thereof is a humanized antibody or antigen-binding fragment thereof which comprises an LC and HC, wherein the LC comprises a polypeptide selected from SEQ ID NO: 53 and SEQ ID NO: 55, and the HC comprises a polypeptide selected from SEQ ID NO: 61 and SEQ ID NO: 63. Preferably, the LC comprises SEQ ID NO: 53 and the HC comprises SEQ ID NO: 61.

In a preferred embodiment, the antibody or antigen-binding fragment thereof is a humanized antibody or antigen-binding fragment thereof which comprises two LCs and two HCs, wherein each LC comprises a polypeptide selected from SEQ ID NO: 53 and SEQ ID NO: 55, and each HC comprises a polypeptide selected from SEQ ID NO: 61 and SEQ ID NO: 63. Preferably, each LC comprises SEQ ID NO: 53 and each HC comprises SEQ ID NO: 61.

SEQ ID NO: 53 has the following sequence:

DIVMTQSPDSLAVSLGERATINCKSSQSLLNSRNRKNYLAWYQQKPG

QPPKLLIYWASTRDSGVPDRFSGSGSGTDFTLTISSLQAEDVAVYYC

KQSYNLRTFGQGTKLEIK

SEQ ID NO: 55 has the following sequence:

EIVLTQSPGTLSLSPGERATLSCKSSQSLLNSRNRKNYLAWYQQKPG

QAPRLLIYWASTRDSGIPDRFSGSGSGTDYTLTISRLEPEDFAVYYC

KQSYNLRTFGGGTKVEIK

SEQ ID NO: 61 has the following sequence:

QVQLQESGPGLVKPSGTLSLTCAVSGFSLTSYGVHWVRQPPGKGLEW

LGALWASGNTDYSSTLMSRVTISVDKSKNQFSLRLSSVTAADTAVYY

CARDRGILTGGYFDVWGKGTTVTVSS

SEQ ID NO: 63 has the following sequence:

QVQLQESGPGLVKPSETLSLTCTVSGFSLTSYGVHWIRQPPGKGLEW

LGALWASGNTDYSSTLMSRVTISVDTSKNQFSLKLSSVTAADTAVYY

CARDRGILTGGYFDLWGRGTLVTVSS

In a preferred embodiment, the antibody or antigen-binding fragment thereof is a humanized antibody or antigen-binding fragment thereof which comprises an LC and an HC, wherein the LC is selected from SEQ ID NO: 57 and SEQ ID NO: 59, and the HC is selected from SEQ ID NO: 65 and SEQ ID NO: 67. Preferably, the LC is SEQ ID NO: 57 and the HC is SEQ ID NO: 65.

In a preferred embodiment, the antibody or antigen-binding fragment thereof is a humanized antibody or antigen-binding fragment thereof which comprises two LCs and two HCs, wherein each LC is selected from SEQ ID NO: 57 and SEQ ID NO: 59, and each HC is selected from SEQ ID NO: 65 and SEQ ID NO: 67. Preferably, each LC is SEQ ID NO: 57 and each HC is SEQ ID NO: 65.

SEQ ID NO: 57 has the following sequence:

DIVMTQSPDSLAVSLGERATINCKSSQSLLNSRNRKNYLAWYQQKPG

QPPKLLIYWASTRDSGVPDRFSGSGSGTDFTLTISSLQAEDVAVYYC

KQSYNLRTFGQGTKLEIKRTVAAPSVFIFPPSDEQLKSGTASVVCLL

NNFYPREAKVQWKVDNALQSGNSQESVTEQDSKDSTYSLSSTLTLSK

ADYEKHKVYACEVTHQGLSSPVTKSFNRGEC

SEQ ID NO: 59 has the following sequence:

EIVLTQSPGTLSLSPGERATLSCKSSQSLLNSRNRKNYLAWYQQKPG

QAPRLLIYWASTRDSGIPDRFSGSGSGTDYTLTISRLEPEDFAVYYC

KQSYNLRTFGGGTKVEIKRTVAAPSVFIFPPSDEQLKSGTASVVCLL

NNFYPREAKVQWKVDNALQSGNSQESVTEQDSKDSTYSLSSTLTLSK

ADYEKHKVYACEVTHQGLSSPVTKSFNRGEC

SEQ ID NO: 65 has the following sequence:

```
QVQLQESGPGLVKPSGTLSLTCAVSGFSLTSYGVHWVRQPPGKGLEW

LGALWASGNTDYSSTLMSRVTISVDKSKNQFSLRLSSVTAADTAVYY

CARDRGILTGGYFDVWGKGTTVTVSSASTKGPSVFPLAPSSKSTSGG

TAALGCLVKDYFPEPVTVSWNSGALTSGVHTFPAVLQSSGLYSLSSV

VTVPSSSLGTQTYICNVNHKPSNTKVDKKVEPKSCDKTHTCPPCPAP

ELLGGPSVFLFPPKPKDTLMISRTPEVTCVVVDVSHEDPEVKFNWYV

DGVEVHNAKTKPREEQYNSTYRVVSVLTVLHQDWLGKEYKCKVSNKA

LPAPIEKTISKAKGQPREPQVYTLPPSRDELTKNQVSLTCLVKGFYP

SDIAVEWESNGQPENNYKTTPPVLDSDGSFFLYSKLTVDKSRWQQGN

VFSCSVMHEALHNHYTQKSLSLSPGK
```

SEQ ID NO: 67 has the following sequence:

```
QVQLQESGPGLVKPSETLSLTCTVSGFSLTSYGVHWIRQPPGKGLEW

LGALWASGNTDYSSTLMSRVTISVDTSKNQFSLKLSSVTAADTAVYY

CARDRGILTGGYFDLWGRGTLVTVSSASTKGPSVFPLAPSSKSTSGG

TAALGCLVKDYFPEPVTVSWNSGALTSGVHTFPAVLQSSGLYSLSSV

VTVPSSSLGTQTYICNVNHKPSNTKVDKKVEPKSCDKTHTCPPCPAP

ELLGGPSVFLFPPKPKDTLMISRTPEVTCVVVDVSHEDPEVKFNWYV

DGVEVHNAKTKPREEQYNSTYRVVSVLTVLHQDWLNGKEYKCKVSNK

ALPAPIEKTISKAKGQPREPQVYTLPPSRDELTKNQVSLTCLVKGFY

PSDIAVEWESNGQPENNYKTTPPVLDSDGSFFLYSKLTVDKSRWQQG

NVFSCSVMHEALHNHYTQKSLSLSPGK
```

In a preferred embodiment, the antibody or antigen-binding fragment thereof is obtained or is obtainable from the hybridoma cell line
(a) MWT 11-1-3, Deposit No: DSM ACC3314, Deposit date: Dec. 1, 2016 or
(b) MWT 119-8-6, Deposit No: DSM ACC3316, Deposit date: Dec. 1, 2016,
deposited by: Fraunhofer-Institut für Zelltherapie und Immunologie IZI Perlickstr. 1; 04103 Leipzig; Germany.

The hybridoma cell lines were deposited in accordance with the Budapest Treaty and are available at the Deutsche Sammlung für Mikroorganismen und Zellkulturen (DSMZ), Inhoffenstr. 7b, 38124 Braunschweig, DE.

In a preferred embodiment, the antibody or antigen-binding fragment thereof is a monoclonal antibody or antigen-binding fragment thereof.

In another embodiment, the invention provides antibodies and functional fragments thereof that bind to isoAsp7 Aβ peptides in the circulation and tissue, in particular in the brain. The antibodies of the invention are capable of binding isoAsp7 Aβ peptide molecules in a monomeric, dimeric, trimeric, etc, or a polymeric form, in form of an aggregate, oligomer, fibers, filaments or in the condensed form of a plaque.

In a further embodiment, the invention provides antibodies and antigen binding fragments thereof, wherein the antibodies specifically bind to the isoaspartate modification of isoAsp7 Aβ.

Pharmaceutical Composition

In a second aspect, the present invention provides a pharmaceutical composition comprising the antibody or antigen-binding fragment thereof of the present invention and a pharmaceutically acceptable carrier or diluent.

As used herein, "pharmaceutically acceptable carrier" or "pharmaceutically acceptable diluent" means any and all solvents, dispersion media, coatings, antibacterial and antifungal agents, isotonic and absorption delaying agents, compatible with pharmaceutical administration. The use of such media and agents for pharmaceutically active substances is well known in the art. Acceptable carriers, excipients, or stabilizers are nontoxic to recipients at the dosages and concentrations employed and, without limiting the scope of the present invention, include: additional buffering agents; preservatives; co-solvents; antioxidants, including ascorbic acid and methionine; chelating agents such as EDTA; metal complexes (e.g., Zn-protein complexes); biodegradable polymers, such as polyesters; salt-forming counterions, such as sodium, polyhydric sugar alcohols; amino acids, such as alanine, glycine, glutamine, asparagine, histidine, arginine, lysine, ornithine, leucine, 2-phenylalanine, glutamic acid, and threonine; organic sugars or sugar alcohols, such as lactitol, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as urea, glutathione, thioctic acid, sodium thioglycolate, thioglycerol, [alpha]-monothioglycerol, and sodium thio sulfate; low molecular weight proteins, such as human serum albumin, bovine serum albumin, gelatin, or other immunoglobulins; and hydrophilic polymers, such as polyvinylpyrrolidone.

A pharmaceutical composition as described herein may also contain other substances. These substances include, but are not limited to, cryoprotectants, lyoprotectants, surfactants, bulking agents, anti-oxidants, and stabilizing agents. In some embodiments, the pharmaceutical composition may be lyophilized.

The term "cryoprotectant" as used herein, includes agents which provide stability to the antibody against freezing-induced stresses, by being preferentially excluded from the antibody's surface. Cryoprotectants may also offer protection during primary and secondary drying and long-term product storage. Non-limiting examples of cryoprotectants include sugars, such as sucrose, glucose, trehalose, mannitol, mannose, and lactose; polymers, such as dextran, hydroxyethyl starch and polyethylene glycol; surfactants, such as polysorbates (e.g., PS-20 or PS-80); and amino acids, such as glycine, arginine, leucine, and serine. A cryoprotectant exhibiting low toxicity in biological systems is generally used.

In one embodiment, a lyoprotectant is added to a pharmaceutical composition described herein. The term "lyoprotectant" as used herein, includes agents that provide stability to the antibody during the freeze-drying or dehydration process (primary and secondary freeze-drying cycles), by providing an amorphous glassy matrix and by binding with the antibody's surface through hydrogen bonding, replacing the water molecules that are removed during the drying process. This helps to minimize product degradation during the lyophilization cycle, and improve the long-term product stability. Non-limiting examples of lyoprotectants include sugars, such as sucrose or trehalose; an amino acid, such as monosodium glutamate, non-crystalline glycine or histidine; a methylamine, such as betaine; a lyotropic salt, such as magnesium sulfate; a polyol, such as trihydric or higher sugar alcohols, e.g., glycerin, erythritol, glycerol, arabitol, xylitol, sorbitol, and mannitol; propylene glycol; polyethylene glycol; pluronics; and combinations thereof. The amount of lyoprotectant added to a pharmaceutical composition is generally an amount that does not lead to an unacceptable amount of degradation of the strain when the pharmaceutical composition is lyophilized.

In some embodiments, a bulking agent is included in the pharmaceutical composition. The term "bulking agent" as used herein, includes agents that provide the structure of the freeze- dried product without interacting directly with the pharmaceutical product. In addition to providing a pharmaceutically elegant cake, bulking agents may also impart useful qualities in regard to modifying the collapse temperature, providing freeze-thaw protection, and enhancing the strain stability over long-term storage. Non-limiting examples of bulking agents include mannitol, glycine, lactose, and sucrose. Bulking agents may be crystalline (such as glycine, mannitol, or sodium chloride) or amorphous (such as dextran, hydroxyethyl starch) and are generally used in formulations in an amount from 0.5% to 10%.

Other pharmaceutically acceptable carriers, excipients, or stabilizers, such as those described in Remington's Pharmaceutical Sciences 16th edition, Osol, A. Ed. (1980) may also be included in a pharmaceutical composition described herein, provided that they do not adversely affect the desired characteristics of the pharmaceutical composition. As used herein, "pharmaceutically acceptable carrier" means any and all solvents, dispersion media, coatings, antibacterial and antifungal agents, isotonic and absorption delaying agents, compatible with pharmaceutical administration. The use of such media and agents for pharmaceutically active substances is well known in the art. Acceptable carriers, excipients, or stabilizers are nontoxic to recipients at the dosages and concentrations employed and include: additional buffering agents; preservatives; co-solvents; antioxidants, including ascorbic acid and methionine; chelating agents such as EDTA; metal complexes (e.g., Zn-protein complexes); biodegradable polymers, such as polyesters; salt-forming counterions, such as sodium, polyhydric sugar alcohols; amino acids, such as alanine, glycine, glutamine, asparagine, histidine, arginine, lysine, ornithine, leucine, 2-phenylalanine, glutamic acid, and threonine; organic sugars or sugar alcohols, such as lactitol, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as urea, glutathione, thioctic acid, sodium thioglycolate, thioglycerol, [alpha]-monothioglycerol, and sodium thio sulfate; low molecular weight proteins, such as human serum albumin, bovine serum albumin, gelatin, or other immunoglobulins; and hydrophilic polymers, such as polyvinylpyrrolidone.

The pharmaceutical composition may be prepared for oral, sublingual, buccal, intravenous, intramuscular, subcutaneous, intraperitoneal, conjunctival, rectal, transdermal, intrathecal, topical and/or inhalation-mediated administration. In a preferred embodiment, the pharmaceutical composition may be a solution which is suitable for intravenous, intramuscular, conjunctival, transdermal, intraperitoneal and/or subcutaneous administration. In an alternative embodiment, the pharmaceutical composition may be a gel or solution which is suitable for intrathecal administration.

The pharmaceutical composition may further comprise common excipients and carriers which are known in the state of the art. For solid pharmaceutical compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For solution for injection, the pharmaceutical composition may further comprise cryoprotectants, lyoprotectants, surfactants, bulking agents, anti-oxidants, stabilizing agents and pharmaceutically acceptable carriers. For aerosol administration, the pharmaceutical compositions are generally supplied in finely divided form along with a surfactant and propellant. The surfactant must, of course, be nontoxic, and is generally soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intranasal delivery. For suppositories, traditional binders and carriers may include, for example, polyalkalene glycols or triglycerides.

In a preferred embodiment, the pharmaceutical composition further comprises donepezil, gelantamine, memantine, rivastigmine, a beta sectretase inhibitor, a gamma secretase modulator, an additional antibody selected from the group of pan-Aβ specific antibodies like aducanumab, bapineuzumab, crenezumab, ganteneumab, solanezumab and/or an antibody with specificity to posttranslational phosphorylated or nitrated Aβ peptides.

Medical Uses

In a third aspect, the present invention provides the antibody or antigen-binding fragment thereof of the present invention or the pharmaceutical composition of the present invention for use as a medicament. In a fourth aspect, the present invention provides the antibody or antigen-binding fragment thereof of the present invention or the pharmaceutical composition of the present invention for use in the treatment and/or prevention of a neurodegenerative disease.

The terms "treatment" and "therapy", as used in the present application, refer to a set of hygienic, pharmacological, surgical and/or physical means used with the intent to cure and/or alleviate a disease and/or symptoms with the goal of remediating the health problem. The terms "treatment" and "therapy" include preventive and curative methods, since both are directed to the maintenance and/or reestablishment of the health of an individual or animal. Regardless of the origin of the symptoms, disease and disability, the administration of a suitable medicament to alleviate and/or cure a health problem should be interpreted as a form of treatment or therapy within the context of this application.

The term "prevention", as used in the present application, refers to a set of hygienic, pharmacological, surgical and/or physical means used to prevent the onset and/or development of a disease and/or symptoms. The term "prevention" encompasses prophylactic methods, since these are used to maintain the health of an animal or individual.

The term "therapeutically effective amount" refers to an amount of antibody or fragment thereof which has a therapeutic effect and which is able to alleviate and/or cure a neurological disease.

The terms "individual", "patient" or "subject" are used interchangeably in the present application and are not meant to be limiting in any way. The "individual", "patient" or "subject" can be of any age, sex and physical condition.

In the context of the present invention, the term "neurodegenerative disorder" or "neurodegenerative disease" is understood as any hereditary and/or sporadic condition which is characterized by a progressive nervous system dysfunction. These disorders are often associated with the atrophy of the affected central or peripheral structures of the nervous system. In a preferred embodiment, the neurodegenerative disease is Aβ-related. Preferably, the neurodegenerative disease is associated with the formation of isoAsp7 Aβ-containing plaques.

In a particular embodiment, the antibodies of the invention, which are capable of binding to and clearing or removing isoAsp7 Aβ peptides in biological fluids and tissues, are useful for the prevention and/or treatment of conditions associated with the formation of isoAsp7 Aβ-containing plaques, such as diffuse, neuritic, and cerebrovascular plaques in the brain.

The administration of the antibodies of the invention, including immunologically reactive fragments thereof, may lead to the clearance or removal of isoAsp7 Aβ from the aforementioned plaques or other biological complexes. Thus, the humanized antibody of the invention will be readily transported in the circulation, other body fluids and to sites where the aforementioned plaques and/or other biological complexes are formed or elsewhere where isoAsp7 Aβ exhibits damaging effects.

In addition, removal of isoAsp7 Aβ from plaques or other biological complexes by antibodies of the invention, including immunologically reactive fragments thereof, may lead to the solubilization of insoluble forms of plaques and thus lead to the removal of complete plaques from the affected tissue, such as brain tissue. This, in turn, may lead to improvement of cognition in patients diagnosed with a neurodegenerative disease, such as mild cognitive impairment (MCI), clinical or pre-clinical Alzheimer's disease (AD), like for instance sporadic Alzheimer's disease (SAD) or Familial Alzheimer's dementias (FAD) like Familial British Dementia (FBD) and Familial Danish Dementia (FDD) or others, neurodegeneration in Down Syndrome, and clinical or pre-clinical CAA.

In a preferred embodiment, the present invention provides a method for treating and/or preventing a neurodegenerative disorder. Preferably, the method comprises administering the antibody of the present invention or antigen-binding thereof to a patient.

In a preferred embodiment, the present invention provides a method of treating Alzheimer's disease. Preferably, the method comprises administering the antibody of the present invention or antigen-binding fragment thereof to a patient.

The binding of antibodies or antigen binding fragments of the invention to isoAsp7 Aβ in the circulation or other body fluids may further result in the removal of the circulating or soluble forms of isoAsp7 Aβ IsoAsp7 Aβ has a high affinity to other, modified or unmodified Aβ peptides, which results in the formation of oligomeric and supermolecular structures, such as amyloid plaques. It has been shown that in particular these oligomeric structures are highly neurotoxic. The formation of oligomeric structures leads to cell damage and death of neuronal cells. Thus, the removal of circulating or soluble forms of Aβ isoAsp7 or even of oligomers comprising isoAsp7 Aβ leads to the prevention of cell damage and/or neurotoxicity. Thus, the invention also provides methods of preventing neurodegenerative diseases, such as mild cognitive impairment (MCI), clinical or pre-clinical Alzheimer's disease (AD), like for instance sporadic Alzheimer's disease (SAD) or Familial Alzheimer's dementias (FAD) like Familial British Dementia (FBD) and Familial Danish Dementia (FDD) or others, neurodegeneration in Down Syndrome, and clinical or pre-clinical CAA.

The invention further provides methods of preventing and/or treating other diseases which are based on or associated with amyloid-like proteins, in particular Aβ isoAsp7, such as progressive supranuclear palsy, multiple sclerosis, Creutzfeld Jacob disease, Parkinson's disease, HIV-related dementia, ALS (amyotrophic lateral sclerosis), dementia related to Adult Onset Diabetes; senile cardiac amyloidosis, and others, including macular degeneration.

In a preferred embodiment, the neurodegenerative disease is selected from the list consisting of mild cognitive impairment, clinical or preclinical Alzheimer's disease, neurodegeneration in Down Syndrome, clinical and preclinical amyloid angiopathy, progressive supranuclear palsy, multiple sclerosis, Creutzfeld Jacob disease, Parkinson's disease, HIV-related dementia, ALS (amyotrophic lateral sclerosis), dementia related to Adult Onset Diabetes; senile cardiac amyloidosis and muscular degeneration. Preferably, the disease is clinical or preclinical Alzheimer's disease.

Hybridoma Cell Line

In a fifth aspect, the present invention provides a hybridoma cell line deposited as follows:
(a) MWT 11-1-3, Deposit No: DSM ACC3314, Deposit date: Dec. 1, 2016; and/or
(b) MWT 119-8-6, Deposit No: DSM ACC3316, Deposit date: Dec. 1, 2016.

MWT 11-1-3 secretes monoclonal antibody K11 and MWT 119-8-6 secretes monoclonal antibody K119.

In an alternative aspect, the present invention provides a hybridoma cell line that can express any one of the antibodies of the present invention or antigen-binding fragments thereof.

The present invention also provides (i) a nucleic acid encoding the antibody of the present invention or an antigen-binding fragment thereof, (ii) a vector comprising the nucleic acid, and (iii) a cell comprising the nucleic acid and/or vector. Preferably the cell is a mammalian cell.

Diagnosis

In a sixth aspect, the present invention provides the use of the antibody or antigen-binding fragment thereof of the present invention for the diagnosis and/or prognosis of a neurodegenerative disease.

In a preferred embodiment, the antibody or antigen-binding fragment is derivatized in any manner which has been previously discussed. For example, the antibody may be fused to hydrogen peroxidase and used in an ELISA to diagnose and/or prognose a neurodegenerative disease.

The invention further envisions the use of the antibody or antigen-binding fragment thereof of the present invention in a highly sensitive and concomitantly robust detection technique that allows quantitative determination of Aβ variants, in particular isoAsp7 Aβ, in biological samples, e.g. liquor (cerebrospinal fluid) or serum samples, preferably serum samples, or tissue samples. This is a tremendous challenge, taking the low abundance of these isoAsp7 Aβ peptides in blood into account. Having such a detection technique available is, however, a prerequisite for studying efficacy of small molecule inhibitors in drug screening and drug development programs.

In a seventh aspect, the present invention provides a method for detecting L-isoAsp7 Aβ comprising a step wherein an isolated sample is put into contact with the antibody or antigen-binding fragment thereof of the present invention.

The method may involve the method steps of a direct or indirect ELISA, an agglutination assay, an immunochromatography assay, a radioimmunology assay, a pull-down assay, an immunofluorescence assay or an immunostaining assay.

In a preferred embodiment, the method comprises: (a) quantifying the amount of L-isoAsp7-comprising peptide through the use of a sandwich immunoassay, wherein the immobilized capture antibody or antigen-binding fragment thereof is an antibody of the present invention or an antigen-binding fragment thereof, and the detection antibody is an antibody or antigen-binding fragment thereof that specifically binds to a polypeptide comprising SEQ ID NO: 1.

In a preferred embodiment, the isolated sample is an isolated serum, liquor/cerebrospinal or another body fluid or tissue sample. Preferably a serum sample.

In an eighth aspect, the present invention provides a method of determining the percentage of Aβ peptide comprising L-isoAsp at position 7 of SEQ ID NO: 1 in an isolated sample. In a preferred embodiment, the method comprises: (a) quantifying the amount of L-isoAsp-comprising peptide through the use of a sandwich immunoassay, wherein the immobilized capture antibody or antigen-binding fragment thereof is an antibody of the present invention or an antigen-binding fragment thereof, and the detection antibody is an antibody or antigen-binding fragment thereof that specifically binds to a polypeptide comprising SEQ ID NO: 1; (b) quantifying the total amount of Aβ through the use of a sandwich immunoassay, wherein the immobilized capture antibody or antigen-binding fragment thereof is an antibody or antigen-binding fragment thereof that specifically binds to a polypeptide comprising SEQ ID NO: 1, and the detection antibody is an antibody or antigen-binding fragment thereof that specifically binds to a polypeptide comprising SEQ ID NO: 1; and (c) determining the percentage value by using the values obtained in steps (a) and (b).

Sandwich immunoassays are common in the art. There are plenty of articles available. For example: Cox K L, Devanarayan V, Kriauciunas A, et al. Immunoassay Methods. 2012 May 1 [Updated 2014 Dec. 24]. In: Sittampalam G S, Coussens N P, Brimacombe K, et al., editors. Assay Guidance Manual [Internet]. Bethesda (Md.): Eli Lilly & Company and the National Center for Advancing Translational Sciences; 2004-. Available from "National Library of Medicine" website (search "Assay Guidance Manual" in Bookshelf section). In a preferred embodiment, the sandwich immunoassay is a direct or indirect ELISA.

The term "specifically bind" refers to a molecule (e.g., antibody or antibody fragment) that binds to a target with at least 2-fold greater affinity than non-target compounds, e.g., at least 4-fold, 5-fold, 6-fold, 7-fold, 8-fold, 9-fold, 10-fold, 20-fold, 25-fold, 50-fold, or 100-fold greater affinity.

In a preferred embodiment, the antibody or antigen-binding fragment thereof that specifically binds to a polypeptide comprising SEQ ID NO: 1 binds to an epitope found at any one of the positions encompassed by residues 1-6 and 8-42 of SEQ ID NO: 1. In other words, the epitope does not comprise the aspartate at position 7 of SEQ ID NO: 1.

The present invention also comprises the following items:

[1] An antibody or antigen-binding fragment thereof which specifically binds to isoAsp7 amyloid β (Aβ), wherein the $K_D$ of the interaction between the antibody and SEQ ID NO: 44 is at least 10 times less than the $K_D$ of the interaction between the antibody and SEQ ID NO: 8.

[2] The antibody or antigen-binding fragment thereof according to item [1], wherein the $K_D$ of the interaction between the antibody and SEQ ID NO: 44 is at least 100 times less than the $K_D$ of the interaction between the antibody and SEQ ID NO: 8.

[3] The antibody or antigen-binding fragment thereof according to any one of items [1]-[2], wherein the antibody or antigen-binding fragment thereof comprises a light chain variable region (VL) and a heavy chain variable region (VH), wherein said VL comprises LCDR1, LCDR2 and LCDR3 polypeptides and VH comprises HCDR1, HCDR2 and HCDR3 polypeptides which are selected from the group consisting of:
  (a) LCDR1 is KSSQSLLNSRNRKNYLA (SEQ ID NO: 9), LCDR2 is WASTRDS (SEQ ID NO: 11), LCDR3 is KQSYNLRT (SEQ ID NO: 13), HCDR1 is GFSLTSYGVH (SEQ ID NO: 14), HCDR2 is ALWASGNTDYSSTLMS (SEQ ID NO: 15), and HCDR3 is DRGILTGGYFDV (SEQ ID NO: 17);
  (b) LCDR1 is KSSQSLFNSRTRKNYVA (SEQ ID NO: 27), LCDR2 is WASTRES (SEQ ID NO: 29), LCDR3 is KQSYNLRA (SEQ ID NO: 30), HCDR1 is GFTFTDYYMS (SEQ ID NO: 32), HCDR2 is FIRNKANGYTTEYSASVKG (SEQ ID NO: 34), and HCDR3 is DIPTIMDY (SEQ ID NO: 35);
  (c) LCDR1 is KSSQSLLNX$_1$RX$_2$RKNYLA (SEQ ID NO: 10), LCDR2 is WASTRX$_3$S (SEQ ID NO: 12), LCDR3 is KQSYNLRT (SEQ ID NO: 13), HCDR1 is GFSLTSYGVH (SEQ ID NO: 14), HCDR2 is X$_4$LWASGX$_5$TDYX$_6$SX$_7$LMS (SEQ ID NO: 16), and HCDR3 is DRGIX$_8$TGGYFDV (SEQ ID NO: 18), wherein X$_1$ is S or R, X$_2$ is N or T, X$_3$ is D or E, X$_4$ is A or V, X$_5$ is N or R, X$_6$ is S or N, X$_7$ is T or A, and X$_8$ is L, T or M; and
  (d) LCDR1 is KSSQX$_1$LX$_2$NSRTRKNYX$_3$A (SEQ ID NO: 28), LCDR2 is WASTRES (SEQ ID NO: 29), LCDR3 is X$_4$QSYNLRX$_5$ (SEQ ID NO: 31), HCDR1 is GFTFX$_6$DYYMX$_7$ (SEQ ID NO: 33), HCDR2 is FIRNKANGYTTEYSASVKG (SEQ ID NO: 34), and HCDR3 is DIPTIMDY (SEQ ID NO: 35), wherein X$_1$ is S or N, X$_2$ is F or L, X$_3$ is V or L, X$_4$ is K or M, X$_5$ is A or T, X$_6$ is T or S, and X$_7$ is S or N.

[4] The antibody or antigen-binding fragment thereof according to any one of items [1]-[3], wherein the antibody or antigen-binding fragment thereof comprises a VL and a VH, wherein the VL and VH are polypeptides selected from the group consisting of:
  (a) VL of SEQ ID NO: 19 and VH of SEQ ID NO: 20;
  (b) VL of SEQ ID NO: 36 and VH of SEQ ID NO: 37;
  (c) VL of SEQ ID NO: 19 and VH of SEQ ID NO: 37; and
  (d) VL of SEQ ID NO: 36 and VH of SEQ ID NO: 20.

[5] The antibody or antigen-binding fragment thereof according to any one of items [1]-[4], wherein the antibody or antigen-binding fragment thereof comprises a light chain (LC) and a heavy chain (HC), wherein said LC and HC are polypeptides selected from the group consisting of:
  (a) LC of SEQ ID NO: 21 and HC of SEQ ID NO: 22;
  (b) LC of SEQ ID NO: 38 and HC of SEQ ID NO: 39;
  (c) LC of SEQ ID NO: 21 and HC of SEQ ID NO: 39; and
  (d) LC of SEQ ID NO: 38 and HC of SEQ ID NO: 22.

[6] The antibody or antigen-binding fragment thereof according to item [5], wherein the antibody or antigen-binding fragment thereof comprises two LCs and two HCs, wherein each LC and each HC are polypeptides selected from the group consisting of:
  (a) LC of SEQ ID NO: 21 and HC of SEQ ID NO: 22;
  (b) LC of SEQ ID NO: 38 and HC of SEQ ID NO: 39;
  (c) LC of SEQ ID NO: 21 and HC of SEQ ID NO: 39; and
  (d) LC of SEQ ID NO: 38 and HC of SEQ ID NO: 22.

[7] The antibody or antigen-binding fragment thereof according to any one of items [1]-[6], wherein the antibody or antigen-binding fragment thereof is obtained or is obtainable from the hybridoma cell line
  (a) MWT 11-1-3, Deposit No: DSM ACC3314, Deposit date: Dec. 1, 2016 or
  (b) MWT 119-8-6, Deposit No: DSM ACC3316, Deposit date: Dec. 1, 2016.

[8] The antibody or antigen-binding fragment thereof according to any one of items [1]-[7], wherein the antibody or antigen-binding fragment thereof is a monoclonal antibody or antigen-binding fragment thereof.

[9] A pharmaceutical composition comprising the antibody or antigen-binding fragment thereof according to any one of items [1]-[8] and a pharmaceutically acceptable carrier or diluent.

[10] The pharmaceutical composition according to item [9], wherein the composition further comprises donepezil, gelantamine, memantine, rivastigmine, a beta secretase inhibitor, a gamma secretase modulator, an additional antibody selected from the group of pan-Aβ specific antibodies like aducanumab, bapineuzumab, crenezumab, ganteneumab, solanezumab and/or an antibody with specificity to posttranslational phosphorylated or nitrated Aβ peptides.

[11] The antibody or antigen-binding fragment thereof according to any one of items [1]-[8] or the pharmaceutical composition according to any one of items [9]-[10] for use as a medicament.

[12] The antibody or antigen-binding fragment thereof according to any one of items [1]-[8] or the pharmaceutical composition according to any one of items [9]-[10] for use in the treatment and/or prevention of a neurodegenerative disease.

[13] The antibody or antigen-binding fragment thereof or the pharmaceutical composition for use according to item [12], wherein the neurodegenerative disease is selected from the list consisting of mild cognitive impairment, clinical or preclinical Alzheimer's disease, neurodegeneration in Down Syndrome, clinical and preclinical amyloid angiopathy, progressive supranuclear palsy, multiple sclerosis, Creutzfeld Jacob disease, Parkinson's disease, HIV-related dementia, ALS (amyotrophic lateral sclerosis), dementia related to Adult Onset Diabetes, senile cardiac amyloidosis and muscular degeneration.

[14] The antibody or antigen-binding fragment thereof or the pharmaceutical composition for use according to any one of items [12]-[13], wherein the neurodegenerative disease is clinical or preclinical Alzheimer's disease.

[15] A hybridoma cell line deposited as follows:
  (a) MWT 11-1-3, Deposit No: DSM ACC3314, Deposit date: Dec. 1, 2016; and/or
  (b) MWT 119-8-6, Deposit No: DSM ACC3316, Deposit date: Dec. 1, 2016.

[16] Use of the antibody or antigen-binding fragment thereof according to any one of claims 1-8 for the diagnosis and/or prognosis of a neurodegenerative disease.

[17] A method for detecting isoAsp7 Aβ comprising a step wherein an isolated sample is put into contact with the antibody or antigen-binding fragment thereof according to any one of claims 1-8.

EXAMPLES

Example 1: Preparation and Screening of Monoclonal Antibodies Directed Against IsoAsp7-Aβ

The aim was the generation of monoclonal antibodies, which react with isoAsp7-Aβ and shorter peptides thereof containing isoaspartate at position 7, but not with the same molecules possessing an aspartate at position 7.

For immunization, a mixture of the peptides isoD7-Aβ (1-12)Cys (SEQ ID NO: 3) and isoD7-Aβ (5-9)repCys (SEQ ID NO: 4) was used. The sulfhydryl groups of terminal cysteine residues were used to conjugate the peptides to Bacterial Transglutaminase (BTG) as carrier. BTG was activated by using the crosslinker SMPH (Succinimidyl-6-[(β-maleimidopropionamido)hexanoate]).

For generation of monoclonal antibodies, 8-week-old female BALB/c mice were immunized with the peptide-BTG-conjugates. Mice were immunized intraperitoneally with a water-in-oil emulsion that was prepared by emulsifying both antigens in equal volumes of Freund's complete adjuvant (priming) or incomplete adjuvant (boosting).

After mice showed sufficient antibody titer in serum, they were sacrificed by cervical dislocation. Spleens were aseptically removed, pooled, homogenized and immortalized by cell fusion using myeloma cell line SP2/0-Agl4 purchased from the German Collection of Microorganisms and Cell Culture (DSMZ GmbH, Braunschweig).

The resulting hybridoma clones were screened according their ability to bind SEQ ID NO: 3-BSA-conjugate, SEQ ID NO: 4-BSA-conjugate, isoD7-Aβ(1-18)-PEG-Biotin (SEQ ID NO: 5) but not the wildtype peptide Aβ(1-18)-PEG-Biotin (SEQ ID NO: 6). Screening of BSA conjugated antigens occurred via direct enzyme-linked immunosorbent assay (ELISA). Binding to biotinylated antigens was analysed by applying the peptides to streptavidin coated plates, followed by direct ELISA.

Stable antibody-producing hybridomas have been selected and subsequently cloned for a second time by limited dilution in order to ensure the monoclonality of the hybridomas. Hybridoma subclones were screened again by ELISA and the best clones chosen for cryopreservation, isotyping and mycoplasma testing.

Example 2: Characterization of Monoclonal Antibodies by Dot Blot Analysis

A simple Dot Blot protocol was accomplished to obtain a general idea about the specificity and cross reactivity of antibodies. 2 µl of the following peptides based on human Aβ were spotted in descending concentrations (200-0.02 µM) on a nitrocellulose membrane: 1—isoD7-Aβ(1-17) (SEQ ID NO:7); 2—isoD7-Aβ (5-9)repCys (SEQ ID NO: 4); 3—Aβ(1-18) (SEQ ID NO: 8); 4—isoD7-Aβ(1-18) (SEQ ID NO: 44). For analysis, membranes were blocked for one hour with TBST-M (TBST (Tris buffered saline+ 0.05% (v/v) Tween-20)+5% (w/v) skimmed milk) at room temperature with gentle shaking. Afterwards, membranes were incubated for 3 hours up to overnight at 4° C. with antibodies K11, K119 and 6E10 diluted to 1 µg/ml in equal volumes of TBST-M. Secondary anti-mouse antibody conjugated with alkaline phosphatase was used for signal detection, following standard procedures.

Results

As shown in FIGS. 1A and B, K11 and K119 are specific for L-isoaspartate at position 7 in the Aβ peptide (Lane 4). In contrast to our isoAsp7-Aβ antibodies, 6E10 is specific for Aβ(1-18) and does not recognize isoAsp7-modified Aβ peptides. Only a weak reactivity was observed for K11 with the highest concentration of the peptide possessing the corresponding D-isoaspartate (Lane 1). The wildtype peptide containing aspartate at position 7 (Lane 3) was not recognized IsoD7 Aβ(1-18) peptide concentrations down to 0.5 μM were clearly detected by K11, but not K119.

Example 3: Characterization of Monoclonal Antibodies by SPR Analysis

Methods

Binding affinities of K11 and K119 to different Aβ species was determined by using Biacore 3000 at a temperature of 25° C. In order to bind analyzing antibodies K11 and K119 to a CM5 sensor Chip (GE Healthcare, Product code BR100012), approximately 15,000-20,000 RU of goat anti mouse IgG (Thermo Fisher Scientific, PA1 28555) were immobilized first. To immobilize the anti-mouse IgG, the carboxymethylated dextran surface of the sensor chip was activated by mixing 0.1 M N-hydroxysuccinimide (NHS) with 0.4 M N-ethyl-N'-(dimethylaminopropyl)carbodiimide hydrochloride (EDC) 1:1. EDC/NHS was applied to the sensor chip for 10 minutes with a flow rate of 10 μl/min. Goat anti mouse IgG was diluted to 50 μg/ml in 10 mM Sodium acetate, pH 5.5 and injected for 2×3 minutes with a flow rate of 10 μl/min. After deactivation with 1 M ethanolamine, pH 8.5 for 2×7 minutes with a flow rate of 10 μl/min, 0.1 M glycine, pH 1.7 was applied to the sensor chip with a flow rate of 30 μl/min for 3 minutes, followed by a washing step with HBS-EP buffer (GE Healthcare, Product code BR100188).

Binding of about 2,000 RU anti isoAsp7-Aβ antibodies occurred with a flow rate of 10 μl/min. To achieve this, antibodies were diluted to 25 μg/ml in HBS-EP buffer and applied to the sensor chip, followed by washing with HBS-EP until the RU signal remains constant.

Kinetic constants were determined by applying Aβ peptides at different concentrations and calculated from the combined set of data by using BIAevaluation software (Biacore AB) (FIG. 2A and FIG. 3).

Results

Table 1 shows the kinetic constants obtained for binding of isoD7-Aβ(1-18) by K11 and K119. K11 binds the L-isoAsp containing antigen isoD7-Aβ (1-18) (SEQ ID NO: 44) with a $K_D$ value of 6.3 nM. K119 has a lower affinity to the antigen ($K_D$ value of 68.5 nM). Much higher $K_D$ values were obtained for binding the D-isoaspartate isomer containing peptide derivative isod7-Aβ(1-17) (SEQ ID NO:7) and the appropriate wildtype sequence Aβ(1-18) (SEQ ID NO: 8) (Table 2). Both antibodies share a strong antigen specificity to L-isoaspartate 7 modified Aβ peptides.

Table 3 shows that isoAsp7-Aβ binding by K11 is not dependent on peptide length. Additionally, a number of posttranslationally modified Aβ peptides found in amyloid plaques of AD patients were tested. Surprisingly, binding of isoD7-Aβ peptides by K11 is enhanced if the N-terminus consists of L-pyroglutamate at position 3 (SEQ ID NO: 48).

TABLE 1

Kinetic constants of isoD7-Aβ(1-18) binding by K11 and K119

| Clone | $k_{on}$ in $s^{-1}M^{-1}$ | $k_{off}$ in $s^{-1}$ | $K_D$ ($k_{off}/k_{on}$) |
|---|---|---|---|
| K11 | 4.07 × 10⁴ | 2.57 × 10⁻⁴ | 6.31 nM |
| K119 | 102 × 10⁴ | 0.07 | 68.5 nM |

TABLE 2

Kinetic constants for binding of different Aβ peptides by K11 and K119

| | | $K_D$ (nM) | |
|---|---|---|---|
| Peptide | SEQ ID NO | K11 | K119 |
| isoD7-Aβ(1-18) | 44 | 6.3 | 68.5 |
| isod7-Aβ(1-17) | 7 | 2690 | n.e.* |
| Aβ(1-18) | 8 | 2700 | 931,000 |

*Not evaluable because of too fast dissociation

TABLE 3

Kinetic constants for binding of different Aβ peptides by K11

| Peptide | SEQ ID NO | $K_D$ (nM) |
|---|---|---|
| isoD7-Aβ(1-40) | 45 | 3.5 |
| Aβ(1-40) | 2 | 1670 |
| isoD7-3NY10-Aβ(1-18) | 46 | 652 |
| pE3-Aβ(3-18) | 47 | 402 |
| pE3-isoD7-Aβ(3-18) | 48 | 1.7 |
| isoD7-PhosphoSer8-Aβ(1-18) | 49 | No binding |
| Mouse isoD7-Aβ(1-18) | 50 | 153 |

Example 4: Characterization of Monoclonal Antibodies by Isothermal Titration Calorimetry (ITC)

In order to verify $K_D$ values obtained by SPR analysis and to further analyze binding kinetics of K11 to isoD7-Aβ(1-18) (SEQ ID NO: 44), Aβ(1-18) (SEQ ID NO: 8), and isod7-Aβ(1-17) (SEQ ID NO: 7) in more detail, the association constant $K_A$, reaction enthalpy ΔH as well as reaction entropy ΔS have been determined by using a VP-ITC microcalorimeter (MicroCal).

Antibodies were dialyzed against ITC buffer (25 mM $KH_2PO_4$; 25 mM $Na_2HPO_4$; 150 mM NaCl; 1 mM EDTA, pH 7.4) overnight at 4° C. Lyophilized peptides were dissolved in ITC buffer to concentrations between 50-240 μM. Afterwards the exact concentration of antibody and peptides was calculated from absorbance at 280 nm and the respective extinction coefficient. The binding heat was recorded at 25° C. by titration of 1×2 μl and 21×14 μl of antigens into the antibody solution every 5 minutes. In order to evaluate the heat development originated by the dilution of Aβ peptides, these values were determined by titration of peptides into dialysis buffer using defined conditions and instrument setup. Plotting of data occurred by MicroCal ORIGIN software. The calculated binding heat was corrected by the heat originated by dilution of the antigen. The resulting curve was fitted by the "One Set of Sites" binding model. With this model, the stoichiometry, association constant, reaction enthalpy and reaction entropy can be calculated.

Results

The top graphs in FIGS. 4 and 5 show the titration curves resulting from titration of antigens in the calorimetric cell with antibody (see FIG. 4 for K11, FIG. 5 for K119). The bottom graphs show the integrated heat pulses, normalized per mol of injectant as a function of molar ratio. In contrast to SPR analysis, no binding of K11 to Aβ(1-18) (SEQ ID NO: 8), and isod7-Aβ(1-17) (SEQ ID NO: 7) was detected.

Table 4 gives an overview about the values calculated for stoichiometry, association constant, reaction enthalpy and reaction entropy for K11 and K119 binding to isoD7-Aβ(1-18) (SEQ ID NO: 44). In order to compare kinetic parameter received from different methods, $K_D$ values obtained by SPR analysis and ITC are shown.

TABLE 4

Thermodynamic parameters of K11 and K119 binding to isoD7-Aβ(1-18)

| Thermodynamic parameter | K11 | K119 |
|---|---|---|
| N | 2.02 | 1.88 |
| $K_A$ (mol$^{-1}$) | $1.15 \times 10^8$ | $0.205 \times 10^8$ |
| ΔH (kcal/mol) | −26.12 | −20.39 |
| ΔS (cal/mol/K) | −0.051 | 0.035 |
| TΔS (kcal/mol) | −10.99 | −9.8 |
| ΔG (kcal/mol) | −15.13 | −10.59 |
| $K_{D\ ITC}$ (nM) | 8.7 | 48.8 |
| $K_{D\ SPR}$ (nM) | 6.3 | 68.5 |

Example 5: Immunohistochemical (IHC) Staining of Mouse Brain Samples

In order to verify the usage of our antibodies for the identification of isoAsp7-Aβ modification in amyloid plaques, sections of brain tissue from animals of a 5×FAD mouse model in different ages have been prepared. 5×FAD transgenic mice overexpress mutant human APP(695) with the Swedish (K670N, M671L), Florida (I716V), and London (V717I) FAD mutations along with human PS1 harboring two FAD mutations, M146L and L286V. In consequence of these mutations, they start to develop an Alzheimer's disease phenotype. The mice have been first described by Oakley et al. (Oakley et al., (2006) J. Neurosci. 26(40): 10129-40) and used in numerous pharmacological assessments since then (Ardestani et al., (2017) Neuropharmacology 116:371-386; Ano et al., (2017) J. Biol. Chem. 292(9): 3720-3728; Cha et al., (2017) Stem Cells Transl. Med. 6(1):293-305; Torika et al., (2017) Brain Behav. Immun. 64:80-90; MacPherson et al., (2017) Neurobiol. Dis. 102: 81-95). Male and female 5×FAD mice have been narcotized with sodium pentobarbital, followed by brain withdrawal. Brains were fixed with paraformaldehyde, incubated for 3 d in 30% (w/v) sucrose in 0.1 M phosphate buffer, shock frozen in methylbutane and stored at −20° C. until further use. Frozen brains were sliced in 30 μm thick sections by using Cryostar NX70. Immunostaining occurred by the avidin biotin peroxidase complex (ABC) method described by HSU et al (HSU et al (1981) J Histochem Cytochem. 29(4):577-80). After washing 3×5 min with TBS, brain slices were incubated for 30 min in 1% (v/v) $H_2O_2$; 60% (v/v) methanol, followed by another wash step and incubation for 30 min in blocking solution (5% (v/v) goat serum; 2.3% (v/v) M.O.M.™ Blocking Reagent in TBS with 0.3% (v/v) Triton-X 100). Incubation with 2 μg/ml primary antibodies K11, K119 or 6E10 (Hiss Diagnostics) in 5% (v/v) goat serum; 0.1% (v/v) Triton-X 100 in TBS occurred overnight at 4° C. After 3×5 min washing with TBS, biotinylated goat anti mouse IgG (Thermo Fisher Scientific) was diluted 1:1000 in TBS with 2% BSA and incubated for 60 min with the samples. ExtrAvidin-Peroxidase (Sigma-Aldrich) was added 1:1000 in TBS with 2% (v/v) BSA after 3×5 min washing steps and incubated for 60 min, followed by 3×5 min washing with TBS and another 5 min washing step with 0.05 M Tris-HCl, pH 7.6. Chromogenic substrate 3,3'-Diaminobenzidin (DAB) (0.05% (w/v) DAB; 0.015% (v/v) $H_2O_2$ in 0.05 M Tris-HCl, pH 7.6) was added for 4-7 min Results Amyloid plaque formation occurs in 5×FAD mice about six months after birth (FIG. 6C and H). In 3 month old animals, Aβ N-terminal specific antibody 6E10 reacts with cells in cortex (FIG. 6G, arrow 1), Stratum pyramidale (FIG. 6G, arrow 2) and basolateral amygdala (FIG. 6G, arrow 3). This is likely due to staining of freshly synthesized Aβ, e.g. membrane bound Aβ species in form of APP. In contrast to 6E10, isoAsp7-Aβ specific antibody K11 stains exclusively extracellular plaques, presumably consisting of deposited and aged Aβ species. Quantity and proliferation of amyloid plaques further proceed during aging of 5×FAD mice, shown by 6E10 and K11 positive staining (FIG. 6C-E, H-J). While there is no isoAsp7-Aβ staining in wildtype mouse brain (FIG. 6A), antibody 6E10 reacts with single Aβ aggregates, distributed in different brain regions (FIG. 6F).

FIG. 7 shows a comparative staining of brain slices from 12 month old 5×FAD mice with K119 (A), K11 (B), 6E10 (C) and without secondary antibody (D). Furthermore, there is no isoAsp7-Aβ staining with antibody K119 in wildtype brain slices (E). K119 shows similar staining results like K11.

Example 6: Application of K11 in an IsoAsp7-Aβ Specific ELISA

Methods

In order to determine the amounts of isoD7-Aβ in biological samples, an indirect Sandwich ELISA was established. Therefore, K11 was diluted in PBS to 2μg/ml and immobilized on polystyrene 96-well microtiter plates overnight at 4° C. Blocking occurred for 2 hours at 4° C. with ELISA Blocker (Thermo Fisher Scientific). For preparation of the standard curve, synthetic isoD7-Aβ(1-30) was serially diluted with ELISA Blocker+Tween (Thermo Fisher Scientific) from 150 pg/ml down to 1.6 pg/ml and added to the wells in duplicate. Two wells filled with ELISA Blocker+Tween represent the standard curve value 0 pg/ml. After an incubation period of 2 hours at room temperature, plates were washed six times with TBS-T. For detection of bound isoD7-Aβ species, the HRP-conjugated anti Aβ antibody clone 4G8 (Biolegends) was diluted to a final concentration of 1 μg/ml in ELISA Blocker+Tween and incubated for 1 hour at 4° C. with the samples. After three washing steps with TBS-T, a color reaction with commercially available HRP substrate TMB (SureBlue Reserve TMB Microwell Peroxidase Substrate (1-component), KPL) was performed (30 minutes incubation at room temperature in the dark) and subsequently stopped by the addition of 1.2 N $H_2SO_4$. Absorption at 450/540 nm was determined by a Tecan Sunrise plate reader. The standard curve was calculated from measured absorption by a 4-Parameter-Logistic-Fit: y=(A2+(A1−A2)/(1+(x/x0)^p).

In order to determine the amount of total Aβ, a comparative ELISA was established by immobilizing the Aβ-N-terminal specific antibody 3D6 (ATCC Murine Hybridoma Cell Line RB96 3D6.32.2.4) on 96-well microtiter plates, replacing K11. 3D6 recognizes the N-terminus of Aβ(1-X) independent from an isoAsp7 modification (see FIG. 8B).

Results

By using the anti isoD7-Aβ specific antibody K11, an indirect Sandwich ELISA was developed for the quantitative detection of isoD7-Aβ down to 1.6 pg/ml. FIG. 8A shows a characteristic standard curve for the isoAsp7-Aβ specific ELISA. The graph further demonstrates that the non-modified Aβ peptide is not detected.

The development of a total Aβ ELISA, which detects Aβ independent from an isoAsp7 modification, allows on the one hand the determination of the percentage isoAsp7-content in amyloid plaques. On the other hand, the ELISA enables us to determine the influence of K11 antibody treatment (see Example 7+8) on non isoAsp7-modified Aβ peptides.

Example 7: Application of K11 in a 5×FAD Mouse Model

Methods

The ability of K11 to reduce Aβ plaque load in a 5×FAD mouse model was evaluated. To do this, K11 was expressed with an IgG2a subtype in Hek293 cells and purified by protein G affinity chromatography.

In order to determine the appropriate K11 treatment dosage, three month old 5×FAD mice were treated in a first trial intraperitoneally once a week with 500 µg, 150 µg K11 or 500 µg isotype control in PBS. In this initial trial, mice were sacrificed after 12 weeks of treatment. One hemisphere was used for immunohistological staining (for method see Example 5), the other one for ELISA analysis, and the cerebellum and brainstem were used for IgG2a quantification (see Example 8). The last antibody application occurred 7 days before brain preparation.

Regions of interest (ROI) in hippocampal brain slices were selected by staining with 2 µg/ml 6E10 (for general Aβ) and 2 µg/ml isoAsp7-Aβ specific antibody K11 (for isoAsp7-Aβ). All pictures were recorded by using the microscope Biorevo BZ-9000 (Keyence) with transmitted light modus and an exposure time of 1/200 s. Percental area of isoAsp7-Abeta (ROI isoD7 in %) was quantified based on total area of ROI by using the program BZ II Analyzer.

In order to prepare mouse brain for ELISA analysis, the left hemisphere was homogenized in T-Per buffer (Thermo Fisher Scientific) with Protease Inhibitor Cocktail Tablets (Roche) by using a Precellys Homogenizer (VWR), followed by sonification for 10 s. The homogenate was centrifuged for 1 hour at 100,000×g. The resulting pellet was dissolved to 150 mg/ml in 5 M Guanidine hydrochloride (5 M GdmCl), followed by an incubation step in an overhead shaker for 3 hours at room temperature. After a centrifugation step (1 h at 100,000×g), supernatant was collected and stored at −20° C. until use. For details on how the ELISA measurements were performed, see Example 6.

Results

By using the isoAsp7- and total Aβ specific ELISAs, a dose dependent reduction of isoAsp7- and total Aβ plaque load in comparison to the isotype control group was shown (FIG. 9).

Immunohistological evaluation after plaque staining with K11 also shows a clear reduction of Aβ plaque load in comparison to the isotype control group (FIGS. 10 and 11). As shown by Dot Blot analysis in FIG. 1, commercially available antibody 6E10 is specific for unmodified Aβ peptides and does not react with isoAsp7-Aβ. FIG. 12 shows immunohistological staining of brain slices from K11-treated 5×FAD mice by using 6E10. Despite 6E10 not recognizing isoAsp7-Aβ, we saw a clear reduction in Aβ plaque load after K11 treatment. This clearly demonstrates that targeting isoAsp7-Aβ results in a reduction of non-modified total Aβ plaque load (FIG. 12).

Example 8: Brain Penetration of K11 in 5×FAD Mice

Since cerebellum and brainstem have no or very low plaque load in 5×FAD mice, they have been used for quantification of IgG2a content. Therefore, cerebellum and brainstem were homogenized in ELISA Blocker+Tween (Thermo Fisher Scientific) by using a Precellys Homogenizer (VWR), followed by 30 minutes centrifugation at 25,000×g. Protein concentration in the resulting supernatants was determined by using BCA assay (Thermo Fisher Scientific). IgG2a concentration was quantified by a mouse IgG2a specific ELISA. Therefore, rat anti mouse IgG2a (BD Bioscience) was diluted in PBS to 1 µg/ml and immobilized on polystyrene 96-well microtiter plates overnight at 4° C. Blocking occurred for 2 hours at room temperature with ELISA Blocker (Thermo Fisher Scientific). For preparation of the standard curve, recombinant IgG2a subtype K11 was serially diluted with ELISA Blocker+Tween (Thermo Fisher Scientific) from 500 ng/ml down to 0.7 ng/ml and added to the wells in duplicate. Two wells filled with ELISA Blocker+Tween represent the standard curve value 0 pg/ml. After an incubation period of 2 hours at room temperature, plates were washed three times with TBS-T. For detection of bound IgG2a molecules, goat anti mouse HRP (KPL) was diluted 1:5000 in ELISA Blocker +Tween and incubated for 1 hour at 4° C. with the samples. For color reaction and calculation of standard curve see isoAsp7-Aβ specific ELISA (Example 6).

Results

FIG. 13 shows a dose dependent increase of brain IgG2a after application of K11 to 5×FAD mice in comparison to an untreated control group.

Example 9: Application of K11 in a 5×FAD Mouse Model—38 Weeks of Treatment

Methods

In contrast to Example 7, three month old 5×FAD mice were treated for 38 weeks with 300 µg K11, 300 µg 3D6 and 300 µg isotype control. Positive control antibody 3D6 was purified after expression in the Murine Hybridoma Cell Line RB96 3D6.32.2.4 (ATCC). Because 12 month old 5×FAD mice show significant memory deficits in comparison to wildtype animals, in addition to ELISAs (see Example 6), behavior tests were performed. To preclude any influence of our isotype control antibody, wildtype mice have also been treated with 300 µg isotype control per week.

Elevated Plus Maze (EPM)

EPM is a test for the measurement of anxiety, based on the test animal's aversion to open spaces. Test animals were placed with their head to the end of a defined closed arm of an elevated, plus-shaped (+) apparatus with two open and two enclosed arms (Bioserve GmbH, Bonn, Germany). During the following 10 minutes, every movement of test animals has been recorded. The time the animals spent in the open arms was summed up in order to calculate % in exposed area.

A movement was defined as arm entry when the complete animal (except tail) was present in the open arm.

Fear Conditioning (FC)

FC is a test for the measurement of learning in which an aversive stimulus (electrical shock) is associated with a particular neutral stimulus (a tone). Successful learning will lead to the evocation of state of fear (freezing) by the neutral stimulus alone. Test animals were placed in an automated FearConditioning System (TSE Systems, Bad Homburg, Germany) and submitted to the following procedure: pause (180 s), sound (28 s), electric stimulus (0.7 mA for 2 s). After 24 h, test animals were again placed in the FearConditioning System, left there for 210 s and have been removed. One hour later, animals came back in the container in order to expose them to 180 s pause, followed by 180 s of sound (neutral stimulus). Freezing times during 180 s pause were counted and subtracted from the freezing times during 180 s sound.

Pole Test

This is a test for the measurement of motor coordination Animals were placed with their head directed to the top of a 50 cm high pole (diameter 1.5 cm). Immediately after unhanding the animal, the amount of time required for the animals to turn around (defined as every single paw is directed to the ground) and reach the ground with every paw were recorded.

Morris Water Maze (MWM) Test

This is a test for the measurement of spatial learning and memory. Test animals were placed in a circular pool and were required to find an invisible platform that allows them to escape the water. Thereby, the animals use distal cues on the edge of the pool as points of reference to orient themselves. The circular pool is divided into 4 equal quadrants, which can be visually distinguished by the cues. Test animals were placed into the first quadrant and the time was counted until they reached the platform. If they did not reach the platform after 60 s, the mice were led to it. After at least a 5 min rest, test animals were placed into the second quadrant and exposed to the same procedure. The animals were allowed to rest again, followed by putting them in quadrant 3, followed by another rest and then putting them again in quadrant 2. At the end, the time it took the test animals reach the platform was recorded and summed up for every mouse in 4 trials per day.

Results

T-Per (Tissue Protein Extraction Reagent, Thermo Fisher Scientific) contains a mild detergent and was shown to extract target proteins from various cellular compartments, for example from plasma membrane. Mainly monomeric and oligomeric Aβ peptides are supposed to be present in the T-Per fraction. GdmCl is a strong denaturant of folded protein structures. Aβ peptides from fibrillary structures will be dissolved in the 5 M GdmCl fraction.

FIG. 14 shows the amount of isoAsp7- and total Aβ in T-Per fractions after 38 weeks of treatment with three different antibodies. The ELISA results show a significant reduction of isoD7-Aβ in animals treated with K11 (FIG. 14B). Surprisingly, total Aβ levels are also significantly reduced in comparison to the animals treated with isotype control (FIG. 14A). Similar results were obtained after the analysis of the 5 M GdmCl brain fractions (FIG. 15). Total Aβ levels as well as isoD7-Aβ levels are significantly reduced in the left hemisphere of 5×FAD mice treated with our anti isoD7-Aβ antibody K11. Treatment with the positive control antibody 3D6 also resulted in lower Aβ contents in T-Per as well as 5 M GdmCl fractions, but a statistically significant difference was only observed for the amount total Aβ found in T-Per fractions (FIG. 14A).

The EPM test shows significant differences between wildtype and 5×FAD mice treated with isotype control (FIG. 16). Treatment with K11 as well as 3D6 reduced the difference in the time animals spent in open arms (FIG. 16A). Considering the number of arm entries, treatment with K11 leads to the same results obtained with wildtype animals (FIG. 16B).

5×FAD animals treated with isotype control show significantly lower freezing times in comparison to the wildtype group in the Fear Conditioning test (FIG. 17). Treatment with K11 enhances freezing times to a level not significantly different to wildtype animals. Treatment with 3D6 has lower effects on total freezing times.

The Pole test shows significant differences between wildtype and 5×FAD mice treated with isotype control (FIG. 18). Treatment with 3D6 has no effect on behavior results in the Pole test. K11 treatment reduced the time until animals turned around (FIG. 18A) as well as the time until they reached the ground (FIG. 18B), resulting in a non-significant difference in comparison to the wildtype group.

5×FAD animals treated with isotype control needed significantly more time until they reached the platform in the MWM test in comparison to the wildtype animals (FIG. 19). The differences observed in 3D6 treated animals are still significant; whereas K11 treated animals show no significant differences to the wildtype.

Example 10: Inhibition of Aβ Aggregation

Methods

Peptides were dissolved in hexafluoroisopropanol (HFIP) in order to yield their monomeric form. HFIP was evaporated overnight, Aβ peptides were then dissolved in 1 volume 0.1 M NaOH, followed by addition of 18 volumes PBS and 1 volume 0.1 M HCl. Antibodies K11, 3D6 and isotype control were added subsequently to a final concentration of 5 μM, leading to a final concentration of 10 μM Aβ peptides. After addition of 200 μM ThT (Thioflavin T), fluorescence at 435/485 nm (excitation/emission) was measured in a microplate reader (FluoStar Optima, BMG Labtech) at 37° C. under shaking conditions (600 rpm).

Results

FIG. 20 shows the aggregation of wildtype Aβ(1-40) (FIG. 20A) and isoD7-Aβ(1-40) (FIG. 20B) with or without the addition of antibodies K11, 3D6 and isotype control. The N-terminal specific antibody 3D6 inhibits aggregation of wildtype Aβ as well as isoD7-Aβ. The isoD7-Aβ specific antibody K11 inhibits aggregation of isoD7-Aβ and induces a delay in the aggregation of wildtype Aβ. The isotype control antibody has no effect on aggregation of both Aβ peptides. However, the maximum ThT fluorescence signal is enhanced by the interaction of wildtype Aβ(1-40) with K11 (FIG. 20A).

Example 11: Humanization of Clone K11 by CDR Grafting

Methods

The definition of the CDRs in the variable domains of K11 light and heavy chain is in accordance with the "Enhanced Chothia Numbering Scheme". Available at "Antibody Information" section of website entitled "Andrew C. R. Martin's group at UCL."

For grafting, appropriate human framework sequences were identified. These were the human framework sequences with the highest similarity to the non-human antibody and they were identified by performing a Blast analysis on the IMGT germline library (http://www.imgt.org/blast/). The CDRs of the mouse antibody clone K11 were combined with the respective human antibody frameworks to create a humanized antibody. The heavy chain constant region of human IgG1 was used for the "intact" antibodies. The light chain variable domain was fused to the human kappa chain constant region (Table 5).

TABLE 5

Antibody framework subfamilies of mouse K11 and humanized K11 antibodies.

|    | mouse      | human 1    | human 2     |
|----|------------|------------|-------------|
| VL | IGKV8-21*01 | IGKV4-1*01 | IGKV3-20*01 |
| VH | IGHV2-9*02  | IGHV4-4*01 | IGHV4-59*01 |

Example 12: Characterization of Recombinantly Expressed Humanized Antibody K11 Variants

Methods

Cloning

The sequences of the light and heavy chain of the humanized antibodies were cloned separately into the mammalian expression vector pVITRO-neo. To identify the optimal combination of VL and VH frameworks, different plasmid combinations were used to perform transient expressions in HEK293F cells.

Transient Transfection and Purification

Transfection was performed in a 15 ml culture medium containing $2 \times 10^6$ HEK293 cells/ml by using 3 µg/ml of polyethylenimine (PEI) mixed with a single plasmid combination (1 µg/ml for each plasmid). At day six, the supernatant was collected and purified by Protein A chromatography.

Surface Plasmon Resonance Measurement

To prevent mass transfer and avidity effects during measurement, the following procedure was used. First a polyclonal anti-human antibody was coupled to an SPR-Chip and subsequently loaded with the humanized antibody until the RU was more than 1000.

Kinetic measurement was performed at different concentrations (of 5 to 1000 nM) of isoD7-Aβ(1-18) peptide. The results are evaluated according to a simple 1:1 interaction model (Langmuir fit), which determines the $k_{off}$ and $k_{on}$ rate constants (Table 6).

Results

TABLE 6

Antigen binding of different humanized K11 antibody variants

| Light chain | Heavy chain | $K_D$ value |
|---|---|---|
| hLC11-IGKV4-1 (SEQ ID NO: 57) | hHC11-IGHV4-4 (SEQ ID NO: 65) | 5.67 nM |
| hLC11-IGKV4-1 (SEQ ID NO: 57) | hHC11-IGHV4-59 (SEQ ID NO: 67) | 14.2 nM |
| hLC11-IGKV3-20*01 (SEQ ID NO: 59) | hHC11-IGHV4-4 (SEQ ID NO: 65) | 10.2 nM |
| hLC11-IGKV3-20*01 (SEQ ID NO: 59) | hHC11-IGHV4-59 (SEQ ID NO: 67) | 18.3 nM |

The humanization of K11 by CDR-grafting yielded antibodies that successfully conserved the binding affinity towards SEQ ID NO: 44 of the ancestral mouse antibody K11 (6.3 nM according to Table 2).

---

The invention claimed is:

1. An antibody or antigen-binding fragment thereof which specifically binds to L-isoAsp7 amyloid β (Aβ), wherein the $K_D$ of the interaction between the antibody and SEQ ID NO: 44 is at least 10 times less than the $K_D$ of the interaction between the antibody and SEQ ID NO: 8 and the $K_D$ is determined by surface plasmon resonance at 25° C.
and wherein the antibody or antigen-binding fragment thereof comprises a light chain variable region (VL) and a heavy chain variable region (VH), wherein said VL comprises LCDR1, LCDR2 and LCDR3 polypeptides and VH comprises HCDR1, HCDR2 and HCDR3 polypeptides which are selected from the group consisting of:
(a) LCDR1 is KSSQSLLNSRNRKNYLA (SEQ ID NO: 9), LCDR2 is WASTRDS (SEQ ID NO: 11), LCDR3 is KQSYNLRT (SEQ ID NO: 13), HCDR1 is GFSLTSYGVH (SEQ ID NO: 14), HCDR2 is ALWASGNTDYSSTLMS (SEQ ID NO: 15), and HCDR3 is DRGILTGGYFDV (SEQ ID NO: 17);
(b) LCDR1 is KSSQSLFNSRTRKNYVA (SEQ ID NO: 27), LCDR2 is WASTRES (SEQ ID NO: 29), LCDR3 is KQSYNLRA (SEQ ID NO: 30), HCDR1is GFTFTDYYMS (SEQ ID NO: 32), HCDR2 is FIRNKANGYTTEYSASVKG (SEQ ID NO: 34), and HCDR3 is DIPTIMDY (SEQ ID NO: 35);
(c) LCDR1 is KSSQSLLNX$_1$RX$_2$RKNYLA (SEQ ID NO: 10), LCDR2 is WASTRX$_3$S (SEQ ID NO: 12), LCDR3 is KQSYNLRT (SEQ ID NO: 13), HCDR1 is GFSLTSYGVH (SEQ ID NO: 14), HCDR2 is X$_4$LWASGX$_5$TDYX$_6$SX$_7$LMS (SEQ ID NO: 16), and HCDR3 is DRGIX$_8$TGGYFDV (SEQ ID NO: 18), wherein X$_1$ is S or R, X$_2$ is N or T, X$_3$ is D or E, X$_4$ is A or V, X$_5$ is N or R, X$_6$ is S or N, X$_7$ is T or A, and X$_8$ is L, T or M; and
(d) LCDR1 is KSSQX$_1$LX$_2$NSRTRKNYX$_3$A (SEQ ID NO: 28), LCDR2 is WASTRES (SEQ ID NO: 29), LCDR3 is X$_4$QSYNLRX$_5$ (SEQ ID NO: 31), HCDR1 is GFTFX$_6$DYYMX$_7$ (SEQ ID NO: 33), HCDR2 is FIRNKANGYTTEYSASVKG (SEQ ID NO: 34), and HCDR3 is DIPTIMDY (SEQ ID NO: 35), wherein X$_1$ is S or N, X$_2$ is F or L, X$_3$ is V or L, X$_4$ is K or M, X$_5$ is A or T, X$_6$ is T or S, and X$_7$ S or N.

2. The antibody or antigen-binding fragment thereof according to claim 1, wherein LCDR1 is KSSQSLLNX$_1$RX$_2$RKNYLA (SEQ ID NO: 10), LCDR2 is WASTRX$_3$S (SEQ ID NO: 12), LCDR3 is KQSYNLRT (SEQ ID NO: 13), HCDR1 is GFSLTSYGVH (SEQ ID NO: 14), HCDR2 is X$_4$LWASGX$_5$TDYX$_6$SX$_7$LMS (SEQ ID NO: 16), and HCDR3 is DRGIX$_8$TGGYFDV (SEQ ID NO: 18), wherein X$_1$ is S or R, X$_2$ is N or T, X$_3$ is D or E, X$_4$ is A or V, X$_5$ is N or R, X$_6$ is S or N, X$_7$ is T or A, and X$_8$ is L, T or M.

3. The antibody or antigen-binding fragment thereof according to claim 2, wherein X$_1$ is S, X$_2$ is N, X$_3$ is D, X$_4$ is A, X$_5$ is N, X$_6$ is S, X$_7$ is T, and X$_8$ is L.

4. The antibody or antigen-binding fragment thereof according to claim 1, wherein LCDR1 is KSSQSLLN-SRNRKNYLA (SEQ ID NO: 9), LCDR2 is WASTRDS (SEQ ID NO: 11), LCDR3 is KQSYNLRT (SEQ ID NO: 13), HCDR1 is GFSLTSYGVH (SEQ ID NO: 14), HCDR2 is ALWASGNTDYSSTLMS (SEQ ID NO: 15), and HCDR3 is DRGILTGGYFDV (SEQ ID NO: 17).

5. The antibody or antigen-binding fragment thereof according to claim 1, wherein LCDR1 is KSSQSLFNSRTRKNYVA (SEQ ID NO: 27), LCDR2 is WASTRES (SEQ ID NO: 29), LCDR3 is KQSYNLRA (SEQ ID NO: 30), HCDR1 is GFTFTDYYMS (SEQ ID NO: 32), HCDR2 is FIRNKANGYTTEYSASVKG (SEQ ID NO: 34), and HCDR3 is DIPTIMDY (SEQ ID NO: 35).

6. The antibody or antigen-binding fragment thereof according to claim 1, wherein LCDR1 is KSSQX$_1$LX$_2$NSRTRKNYX$_3$A (SEQ ID NO: 28), LCDR2 is WASTRES (SEQ ID NO: 29), LCDR3 is X$_4$QSYNLRX$_5$ (SEQ ID NO: 31), HCDR1 is GFTFX$_6$DYYMX$_7$ (SEQ ID NO: 33), HCDR2 is FIRNKANGYTTEYSASVKG (SEQ ID NO: 34), and HCDR3 is DIPTIMDY (SEQ ID NO: 35), wherein X$_1$ is S or N, X$_2$ is F or L, X$_3$ is V or L, X$_4$ is K or M, X$_5$ is A or T, X$_6$ is T or S, and X$_7$ is S or N.

7. The antibody or antigen-binding fragment thereof according to claim 1, wherein the antibody or antigen-binding fragment thereof is a monoclonal antibody or antigen-binding fragment thereof.

8. The antibody or antigen-binding fragment thereof according to claim 1, wherein the antibody or antigen-binding fragment thereof is a humanized antibody or antigen-binding fragment thereof.

9. A pharmaceutical composition comprising (i) the antibody or antigen-binding fragment thereof according to claim 1 and (ii) a pharmaceutically acceptable carrier or diluent.

10. An antibody or antigen-binding fragment thereof which specifically binds to L-isoAsp7 amyloid β (Aβ), wherein the K$_D$ of the interaction between the antibody and SEQ ID NO: 44 is at least 10 times less than the K$_D$ of the interaction between the antibody and SEQ ID NO: 8 and the K$_D$ is determined by surface plasmon resonance at 25° C., and wherein the antibody or antigen-binding fragment thereof comprises a light chain (LC) and a heavy chain (HC), wherein said LC and HC are polypeptides selected from the group consisting of:
(a) LC of SEQ ID NO: 21 and HC of SEQ ID NO: 22;
(b) LC of SEQ ID NO: 38 and HC of SEQ ID NO: 39;
(c) LC of SEQ ID NO: 21 and HC of SEQ ID NO: 39; and
(d) LC of SEQ ID NO: 38 and HC of SEQ ID NO: 22.

11. The antibody or antigen-binding fragment thereof according to claim 10, wherein LC is polypeptide of SEQ ID NO: 21 and HC is polypeptide of SEQ ID NO: 22.

12. The antibody or antigen-binding fragment thereof according to claim 10, wherein LC is polypeptide of SEQ ID NO: 38 and HC is polypeptide of SEQ ID NO: 39.

13. The antibody or antigen-binding fragment thereof according to claim 10, wherein LC is polypeptide of SEQ ID NO: 21 and HC is polypeptide of SEQ ID NO: 39.

14. The antibody or antigen-binding fragment thereof according to claim 10, wherein LC is polypeptide of SEQ ID NO: 38 and HC is polypeptide of SEQ ID NO: 22.

15. The antibody or antigen-binding fragment thereof according to claim 10, wherein the antibody or antigen-binding fragment thereof is a monoclonal antibody or antigen-binding fragment thereof.

16. A pharmaceutical composition comprising (i) the antibody or antigen-binding fragment thereof according to claim 10 and (ii) a pharmaceutically acceptable carrier or diluent.

* * * * *